(12) United States Patent
Dodic et al.

(10) Patent No.: US 7,241,793 B2
(45) Date of Patent: Jul. 10, 2007

(54) PHENYLOXYALKANONIC ACID DERIVATIVES AS HPPAR ACTIVATORS

(75) Inventors: Nerina Dodic, Les Ulis (FR); Bernard André Dumaître, Les Ulis (FR); Francoise Jeanne Gellibert, Les Ulis (FR); Michael Lawrence Sierra, Les Ulis (FR)

(73) Assignee: SmithKline Beecham Corporation, Philadelphia, PA (US)

( * ) Notice: Subject to any disclaimer, the term of this patent is extended or adjusted under 35 U.S.C. 154(b) by 147 days.

(21) Appl. No.: 10/518,347

(22) PCT Filed: Jun. 18, 2003

(86) PCT No.: PCT/EP03/06417
§ 371 (c)(1),
(2), (4) Date: Dec. 17, 2004

(87) PCT Pub. No.: WO04/000785
PCT Pub. Date: Dec. 31, 2003

(65) Prior Publication Data
US 2005/0222424 A1  Oct. 6, 2005

(30) Foreign Application Priority Data
Jun. 19, 2002 (GB) ................... 0214139.8

(51) Int. Cl.
*A61K 31/415* (2006.01)
*A61K 31/4155* (2006.01)
*C07D 231/38* (2006.01)
*C07D 231/12* (2006.01)

(52) U.S. Cl. .............. 514/406; 514/407; 548/365.7; 548/375.1

(58) Field of Classification Search ............. 514/406, 514/407; 548/375.1, 365.7
See application file for complete search history.

(56) References Cited

U.S. PATENT DOCUMENTS 6,723,743 B1 *  4/2004  Thurkauf et al. ........... 514/396

FOREIGN PATENT DOCUMENTS

| EP | 1067109 | 1/2001 |
|---|---|---|
| WO | WO 01/40207 | 6/2001 |
| WO | WO 02/14291 | 2/2002 |
| WO | WO 02/46174 | 6/2002 |
| WO | WO 200249993 A2 * | 6/2002 |
| WO | WO 02/059098 | 8/2002 |

* cited by examiner

*Primary Examiner*—Kamal A. Saeed
*Assistant Examiner*—Nyeemah Grazier
(74) *Attorney, Agent, or Firm*—Jennifer L. Fox

(57) ABSTRACT

A compound of formula (I) or a pharmaceutically acceptable salt, solvate, or hydrolysable ester thereof, wherein:

(I)

17 Claims, No Drawings

PHENYLOXYALKANONIC ACID DERIVATIVES AS HPPAR ACTIVATORS

This application is a 371 of PCT/EP03/06417 filed Jun. 18, 2003 and claims benefit to foreign application United Kingdom 0214139.8 filed Jun. 19, 2002.

The present invention relates to certain novel compounds. In particular, the present invention relates to compounds that activate human peroxisome proliferator activated receptors ("hPPARs"). The present invention also relates to method for preparing the compounds, their use in medicine, pharmaceutical compositions containing them and methods for the prevention or treatment of PPAR mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been totally successfully addressed by drug therapy (i.e. currently there are no drugs on the market that are useful for raising HDL-c). (Bisgaier, C. L.; Pape, M. E. *Curr. Pharm. Des.* 1998, 4, 53–70).

Syndrome X (including metabolic syndrome) is loosely defined as a collection of abnormalities including hyperinsulemia, obesity, elevated levels of triglycerides, uric acid, fibrinogen, small dense LDL particles, and plasminogen activator inhibitor 1 (PAI-1), and decreased levels of HDL-c.

NIDDM is described as insulin resistance, which in turn causes anomalous glucose output and a decrease in glucose uptake, by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example Willson T. M. and Wahli, W., *Curr. Opin. Chem. Biol.*, 1, pp235–241 (1997) and Willson T. M. et. al., *J. Med. Chem.*, 43, p527–549 (2000). The binding of agonist ligands to the receptor results in changes in the expression level of mRNA's encoded by PPAR target genes.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signalling cascade and lipid homeostasis (H. Keller and W. Wahli, *Trends Endocrinol. Metab* 291–196, 4 (1993)).

It has now been reported that the thiazolidinedione class of drugs are potent and selective activators of PPAR-gamma and bind directly to the PPAR-gamma receptor (J. M. Lehmann et. al., *J. Biol. Chem.* 12953–12956, 270 (1995)), providing evidence that PPAR-gamma is a possible target for the therapeutic actions of the thiazolidinediones.

Activators of the nuclear receptor PPARγ, for example rosiglitazone, have been shown in the clinic to enhance insulin-action, reduce serum glucose and have small but significant effects on reducing serum triglyceride levels in patients with Type 2 diabetes. See, for example, D. E. Kelly et al., *Curr. Opin. Endocrinol. Diabetes*, 90–96, 5 (2), (1998); M. D. Johnson et al., *Ann. Pharmacother.*, 337–348, 32 (3), (1997); and M. Leutenegger et al., *Curr. Ther. Res.*, 403–416, 58 (7), (1997).

The mechanism for this triglyceride lowering effect appears to be predominantly increased clearance of very low density lipoproteins (VLDL) through induction of lipoprotein lipase (LPL) gene expression. See, for example, B. Staels et al., *Arterioscler. Thromb., Vasc. Biol.*, 1756–1764, 17 (9), (1997).

Fibrates are a class of drugs which may lower serum triglycerides 20–50%, lower LDLc 10–15%, shift the LDL particle size from the more atherogenic small dense to normal dense LDL, and increase HDLc 10–15%. Experimental evidence indicates that the effects of fibrates on serum lipids are mediated through activation of PPARα. See, for example, B. Staels et al., *Curr. Pharm. Des.*, 1–14, 3 (1), (1997). Activation of PPARα results in transcription of enzymes that increase fatty acid catabolism and decrease de-novo fatty acid synthesis in the liver resulting in decreased triglyceride synthesis and VLDL production/secretion. In addition, PPARα activation decreases production of apoC-III. Reduction in apoC-III, an inhibitor of LPL activity, increases clearance of VLDL. See, for example, J. Auwerx et al., *Atherosclerosis*, (Shannon, Irel.), S29–S37, 124 (Suppl), (1996).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.) WO99/04815 (Shimokawa et al.) and WO 01/00603 (Glaxo). In a recent report (Berger et al., *J. Biol. Chem.* 1999), vol. 274, pp. 6718–6725) it was stated that PPARdelta activation does not appear to modulate glucose or triglyceride levels.

Accordingly the invention provides a compound of formula 1 and pharmaceutically acceptable salts and solvates and hydrolysable esters thereof.

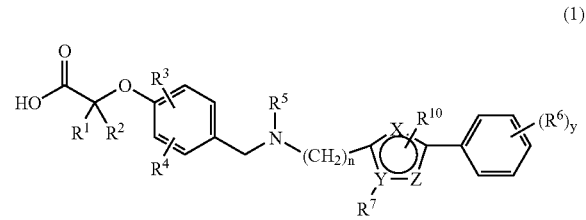

(1)

Wherein:

$R^1$ and $R^2$ are independently H or $C_{1-3}$ alkyl;

$R^3$ and $R^4$ are independently H, $C_{1-3}$ alkyl, $OCH_3$, $CF_3$, allyl, or halogen;

n is 0 or 1

At least one of X, Z and Y represents a heteroatom selected from O, S or N;

Each $R^6$ is independently $C_{1-3}$ alkyl, $CF_3$, $OCH_3$, $OCF_3$, or halogen;

y is 0, 1, 2, 3, 4, or 5;

$R^7$ is H, $CF_3$, $C_{1-6}$ alkyl (optionally substituted by phenyl wherein the phenyl is optionally substituted by —O—$C_{1-3}$ alkyl) or $C_{1-6}$ alkenyl with the proviso that when Z is S or O, $R^7$ is H;

$R^{10}$ is H or $C_{1-6}$ alkyl;

$R^5$ represents H, $C_{1-6}$ alkyl, $C_{1-3}$ alkyl —O—$C_{1-3}$ alkyl, $C_{1-6}$ alkenyl, $C_{1-6}$alkoxy, (each of which may be optionally substituted by one or more halogens), or a group —CH$_2$-D wherein D is

wherein P represents O, N or S (note that when P is N, the depicted bond can be attached to the nitrogen in the ring as well as any of the carbons in the ring).

or

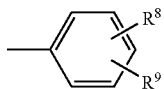

wherein $R^8$ and $R^9$ independently represent H, halogen, $C_{1-6}$ alkyl or —O$C_{1-6}$ alkyl.

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa, cancer, Alzheimers disease or other cognitive disorders. In particular, the compounds of this invention are useful in the treatment and prevention of diabetes and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

As used herein, "a compound of the invention" means a compound of formula (I) or a pharmaceutically acceptable salt, or solvate, or hydrolysable ester thereof.

While hydrolyzable esters are included in the scope of this invention, the acids are preferred because the data suggests that while the esters are useful compounds, it may actually be the acids to which they hydrolyse that are the active compounds. Esters that hydrolyse readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably each $R^1$ and $R^2$ are independently H or methyl. More preferably $R^1$ and $R^2$ are both H or both methyl. Most preferably $R^1$ and $R^2$ are both methyl.

Preferably $R^3$ and $R^4$ are independently H, CH$_3$, Cl. When $R^3$ and $R^4$ are CH$_3$ or Cl, preferably the substituents are positioned ortho to the depicted oxygen. More preferably $R^3$ and $R^4$ are both methyl. Alternatively preferably $R^3$ is methyl or Cl and $R^4$ is H.

Preferably the heterocyclic group comprising X Y and Z atoms in formula (I) above is an 1,2,4 oxadiazole, oxazole, thiazole or pyrazole group. More preferably Z represents N and one of Y and X represents CH. Most preferably when Z represents N, Y represents N and X represents CH or alternatively when Z represents N, X represents S and Y represents CH.

More preferably the heterocycle is selected from the group consisting of:

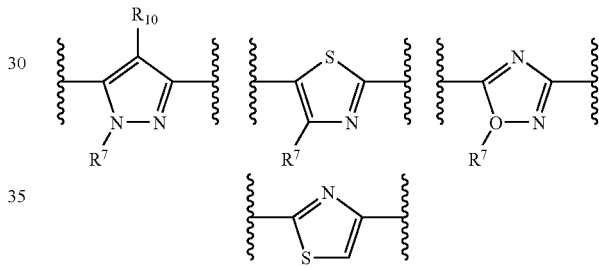

Preferably y represents 1 and $R^6$ is halogen or —OCF$_3$ or —CF$_3$. Most preferably $R^6$ is —CF$_3$. Preferably the substituent $R^6$ is in the para position on the phenyl ring.

Preferably $R^{10}$ represents H or CH$_3$. More preferably $R^{10}$ represents H.

Preferably $R^7$ represents H, $C_{1-6}$ alkyl, $C_{1-3}$ alkenyl, —CH$_2$-phenyl (wherein the phenyl is optionally substituted by —OCH$_3$). Most preferably $R^7$ represents H, $C_{1-3}$ alkyl or —CH$_2$-phenyl (wherein the phenyl is optionally substituted by —OCH$_3$). Most preferably $R^7$ represents H or methyl.

Preferably $R^5$ represents H, $C_{1-3}$ alkyl, CH$_2$D wherein D is defined as above, CH$_2$CF$_3$, $C_{1-3}$ alkyl-O—CH$_3$.

Preferably $R^8$ is H and $R^9$ is H, halogen or OCH$_3$.

In a particular embodiment, the invention provides a compound of formula I(a) and pharmaceutically acceptable salts and solvates and hydrolysable esters thereof.

(1a)

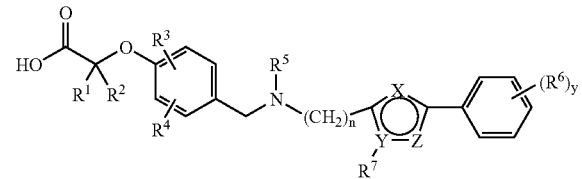

Wherein:

$R^1$ and $R^2$ are independently H or $C_{1-3}$ alkyl;

$R^3$ and $R^4$ are independently H, $C_{1-3}$ alkyl, $OCH_3$, $CF_3$, allyl, or halogen;

n is 0 or 1

At least one of X, Z and Y represents a heteroatom selected from O, S or N;

Each $R^6$ is independently $C_{1-3}$ alkyl, $CF_3$, $OCH_3$, $OCF_3$, or halogen;

y is 0, 1, 2, 3, 4, or 5;

$R^7$ is H, $CF_3$, $C_{1-6}$ alkyl or $C_{1-6}$ alkenyl with the proviso that when Z is S or O, $R^7$ is H;

$R^5$ represents H, $C_{1-6}$ alkyl, $C_{1-6}$ alkenyl, $C_{1-6}$ alkoxy, (each of which may be optionally substituted by one or more halogens), or a group —$CH_2$-D wherein D is

wherein P represents O, N or S (note that when P is N, the depicted bond can be attached to the nitrogen in the ring as well as any of the carbons in the ring).

or

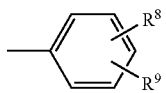

wherein $R^8$ and $R^9$ independently represent H, halogen, $C_{1-6}$ alkyl or —$OC_{1-6}$ alkyl.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

Preferred compounds of the invention include:

2-[2,6-Dimethyl-4-({[4-methyl-2-(4-trifluoromethyl-phenyl)-thiazol-5-yl]-thiophen-3-ylmethyl-amino}-methyl)-phenoxy]-2-methyl-propionic acid ethyl ester 2-[2,6-Dimethyl-4-({[4-methyl-2-(4-trifluoromethyl-phenyl)-thiazol-5-yl]-thiophen-3-ylmethyl-amino}-methyl)-phenoxy]-2-methyl-propionic acid 2-[4-({[5-(4-Chloro-phenyl)-2-methyl-2H-pyrazol-3-yl]-thiophen-3-ylmethyl -amino}-methyl)-2,6-dimethyl-phenoxy]-2-methyl-propionic acid ethyl ester 2-[4-({[5-(4-Chloro-phenyl)-2-methyl-2H-pyrazol-3-yl]-thiophen-3-ylmethyl -amino}-methyl)-2,6-dimethyl-phenoxy]-2-methyl-propionic acid 2-[4-({[5-(4-Chloro-phenyl)-2-methyl-2H-pyrazol-3-yl]-methyl-amino}-methyl)-2,6-dimethyl-phenoxy]-2-methyl-propionic acid ethyl ester 2-[4-({[5-(4-Chloro-phenyl)-2-methyl-2H-pyrazol-3-yl]-methyl-amino}-methyl)-2,6-dimethyl-phenoxy]-2-methyl-propionic acid 2-[4-({(2-Chloro-benzyl)-[5-(4-chloro-phenyl)-2-methyl-2H-pyrazol-3-yl]-amino}-methyl)-2,6-dimethyl-phenoxy]-2-methyl-propionic acid ethyl ester 2-[4-({(2-Chloro-benzyl)-[5-(4-chloro-phenyl)-2-methyl-2H-pyrazol-3-yl]-amino}-methyl)-2,6-dimethyl-phenoxy]-2-methyl-propionic acid 2-[4-({(4-Methoxy-benzyl)-[2-methyl-5-(4-trifluoromethyl-phenyl)-2H-pyrazol-3-yl]-amino}-methyl)-2,6-dimethyl-phenoxy]-2-methyl-propionic acid ethyl ester 2-[4-({(4-Methoxy-benzyl)-[2-methyl-5-(4-trifluoromethyl-phenyl)-2H-pyrazol-3-yl]-amino}-methyl)-2,6-dimethyl-phenoxy]-2-methyl-propionic acid 2-[2,6-Dimethyl-4-({[2-methyl-5-(4-trifluoromethyl-phenyl)-2H-pyrazol-3-yl]-thiophen-3-ylmethyl-amino}-methyl)-phenoxy]-2-methyl-propionic acid ethyl ester 2-[2,6-Dimethyl-4-({[2-methyl-5-(4-trifluoromethyl-phenyl)-2H-pyrazol-3-yl]-thiophen-3-ylmethyl-amino}-methyl)-phenoxy]-2-methyl-propionic acid 2-[4-({(4-Fluoro-benzyl)-[2-methyl-5-(4-trifluoromethyl-phenyl)-2H-pyrazol-3-yl]-amino}-methyl)-2,6-dimethyl-phenoxy]-2-methyl-propionic acid ethyl ester 2-[4-({(4-Fluoro-benzyl)-[2-methyl-5-(4-trifluoromethyl-phenyl)-2H-pyrazol-3-yl]-amino}-methyl)-2,6-dimethyl-phenoxy]-2-methyl-propionic acid 2-(4-{[5-(4-Chloro-phenyl)-2-methyl-2H-pyrazol-3-yl-amino]-methyl}-2-methyl-phenoxy)-2-methyl-propionic acid ethyl ester 2-[4-({[5-(4-Chloro-phenyl)-2-methyl-2H-pyrazol-3-yl]-ethyl-amino}-methyl)-2-methyl-phenoxy]-2-methyl-propionic acid ethyl ester 2-[4-({[5-(4-Chloro-phenyl)-2-methyl-2H-pyrazol-3-yl]-ethyl-amino}-methyl)-2-methyl-phenoxy]-2-methyl-propionic acid 2-[4({(4-Methoxy-phenyl)-[4-methyl-2-(4-trifluoromethyl-phenyl)-thiazol-5-yl]-amino}-methyl)-2,6-dimethyl-phenoxy]-2-methyl-propionic acid ethyl ester 2-[4-({(4-Methoxy-phenyl)-[4-methyl-2-(4-trifluoromethyl-phenyl)-thiazol-5-yl]-amino}-methyl)-2,6-dimethyl-phenoxy]-2-methyl-propionic acid 2-[4-({(2-Chloro-benzyl)-[4-methyl-2-(4-trifluoromethyl-phenyl)-thiazol-5-yl]-amino}-methyl)-2,6-dimethyl-phenoxy]-2-methyl-propionic acid ethyl ester 2-[4-({(2-Chloro-benzyl)-[4-methyl-2-(4-trifluoromethyl-phenyl)-thiazol-5-yl]-amino}-methyl)-2,6-dimethyl-phenoxy]-2-methyl-propionic acid 2-[4-({(4-Fluoro-benzyl)-[4-methyl-2-(4-trifluoromethyl-phenyl)-thiazol-5-yl]-amino}-methyl)-2,6-dimethyl-phenoxy]-2-methyl-propionic acid ethyl ester 2-[4-({(4-Fluoro-benzyl)-[4-methyl-2-(4-trifluoromethyl-phenyl)-thiazol-5-yl]-amino}-methyl)-2,6-dimethyl-phenoxy]-2-methyl-propionic acid 2-methyl-2-[4-(((1 -methyl-3-(4-trifluoromethylphenyl))-pyrazol-5-yl)methyl-N-methyl -aminomethyl)phenoxy]propionic acid ethyl ester 2-methyl-2-[2-methyl-4-(((1-methyl-3-(4-trifluoromethylphenyl))-pyrazol-5-yl)methyl-N-methyl-aminomethyl) phenoxy]propionic acid ethyl ester 2-methyl-2-[2-chloro-4-(((1-methyl-3-(4-trifluoromethylphenyl))-pyrazol-5-yl)methyl-N-methyl-aminomethyl) phenoxy]propionic acid ethyl ester 2-methyl-2-[2-methyl-4-((1,4-dimethyl-3-(4-trifluoromethylphenyl)-pyrazol-5-yl)methyl-N-methyl-aminomethyl) phenoxy]propionic acid ethyl ester 2-methyl-2-[2-chloro-4-((1-methyl-3-(4-trifluoromethoxyphenyl)-pyrazol-5-yl)methyl-N-methyl-aminomethyl)phenoxy]propionic acid ethyl ester 2-methyl-2-[2-methyl-4-((1-methyl-3-(4-trifluoromethylphenyl)-pyrazol-5-yl)methyl-N-propyl-aminomethyl)phenoxy]propionic acid ethyl ester 2-methyl-2-[2-chloro-4-((1-methyl-3-(4-trifluoromethylphenyl)-pyrazol-5-yl)methyl-N-(propen-2-yl)-aminomethyl)phenoxy]propionic acid ethyl ester 2-methyl-2-[4-((1-propyl-3-(4-trifluoromethylphenyl)-pyrazol-5-yl)methyl-N-methyl-aminomethyl)phenoxy]propionic acid ethyl ester 2-methyl-2-[2-chloro-4-((1-propyl-3-(4-trifluoromethylphenyl)-pyrazol-5-yl)methyl-N-methyl-aminomethyl)phenoxy]propionic acid ethyl ester 2-methyl-2-[2-chloro-4-((1-(propen-2-yl)-3-(4-trifluoromethoxyphenyl)-pyrazol-5-yl)methyl-N-methyl-aminomethyl)phenoxy]propionic acid ethyl ester 2-methyl-2-[2-chloro-4-((1-(3-methyl-butyl)-3-(4-trifluoromethoxyphenyl)-pyrazol-5-yl)methyl-N-methyl-aminomethyl)phenoxy]propionic acid ethyl ester 2-methyl-2-[4-((1-benzyl-3-(4-trifluoromethylphenyl)-pyrazol-5-yl)methyl-N-methyl-aminomethyl)phenoxy]propionic acid ethyl ester 2-methyl-2-[2-chloro-4-((1-benzyl-3-(4-trifluoromethylphenyl)-pyrazol-5-yl)methyl-N-methyl-aminomethyl)phenoxy]propionic acid ethyl ester 2-methyl-2-[2-chloro-4-((1-benzyl-3-(4-trifluoromethoxyphenyl)-pyrazol-5-yl)methyl-N-(propen-2-yl)aminomethyl)phenoxy]propionic acid ethyl ester 2-methyl-2-[2-methyl-4-((1-(4-methoxybenzyl)-3-(4-trifluoromethylphenyl)-pyrazol-5-yl)methyl-N-methyl-aminomethyl)phenoxy]propionic acid ethyl ester 2-methyl-2-[4-{[(4-methyl-2-[4-trifluoromethylphenyl]-thiazol-5-ylmethyl)-N-methyl-amino]methyl}phenoxy]propionic acid ethyl ester 2-methyl-2-[2-methyl-4-{[(4-methyl-2-[4-trifluoromethylphenyl]-thiazol-5-ylmethyl)-N-methyl-amino]methyl}phenoxy]propionic acid ethyl ester 2-methyl-2-[2-chloro-4-{[(4-methyl-2-[4-trifluoromethylphenyl]-thiazol-5-ylmethyl)-N-methyl-amino]methyl}phenoxy]propionic acid ethyl ester 2-methyl-2-[4-{[(4-methyl-2-[4-trifluoromethylphenyl]-thiazol-5-ylmethyl)-N-(2,2,2-trifluoromethyl)amino]methyl}phenoxy]propionic acid ethyl ester 2-methyl-2-[2-chloro-4-{[(4-methyl-2-[4-trifluoromethylphenyl]-thiazol-5-ylmethyl)-N-(2,2,2-trifluoromethyl)amino]methyl}phenoxy]propionic acid ethyl ester 2-methyl-2-[4{[(4-methyl-2-[4-trifluoromethylphenyl]-thiazol-5-ylmethyl)-N-(propen-2-yl)amino]methyl}phenoxy]propionic acid ethyl ester 2-methyl-2-[2-methyl-4-{[(4-methyl-2-[4-trifluoromethylphenyl]-thiazol-5-ylmethyl)-N-(propen-2-yl)amino]methyl}phenoxy]propionic acid ethyl ester 2-methyl-2-[4-{[(4-methyl-2-[4-trifluoromethylphenyl]-thiazol-5-ylmethyl)-N-(propen-2-yl)amino]methyl}phenoxy]propionic acid ethyl ester 2-methyl-2-[4-{[(4-methyl-2-[4-trifluoromethylphenyl]-thiazol-5-ylmethyl)-N-(2-methoxyethyl)amino]methyl}phenoxy]propionic acid ethyl ester 2-methyl-2-[2-methyl-4-{([(4-methyl-2-[4-trifluoromethylphenyl]-thiazol-5-ylmethyl)-N-(3-methoxypropyl)amino]methyl}phenoxy]propionic acid ethyl ester 2-methyl-2-[4-{[(4-methyl-2-[4-trifluoromethylphenyl]-thiazol-5-ylmethyl)-N-(benzyl)-amino]methyl}phenoxy]propionic acid ethyl ester 2-methyl-2-[2-methyl-4-{[(4-methyl-2-[4-trifluoromethylphenyl]-thiazol-5-ylmethyl)-N-(benzyl)-amino]methyl}phenoxy]propionic acid ethyl ester 2-methyl-2-[2-chloro-4-{[(4-methyl-2-[4-trifluoromethylphenyl]-thiazol-5-ylmethyl)-N-(benzyl)-amino]methyl}phenoxy]propionic acid ethyl ester 2-methyl-2-[2-methyl-4-{[(4-methyl-2-[4-trifluoromethylphenyl]-thiazol-5-ylmethyl)-N-(furan-2-ylmethyl)-amino]methyl}phenoxy]propionic acid ethyl ester 2-methyl-2-[2-methyl-4-((3-(4-trifluoromethyl-phenyl)-[1,2,4]-oxadiazol-5-yl)methyl-N-methyl-aminomethyl)phenoxy]propionic acid ethyl ester 2-methyl-2-[2-chloro-4-((3-(4-trifluoromethyl-phenyl)-[1,2,4]-oxadiazol-5-yl)methyl-N-methyl-aminomethyl)phenoxy]propionic acid ethyl ester 2-methyl-2-[2-chloro-4-((4-(4-trifluoromethyl-phenyl)-thiazol-2-yl)methyl-N-methyl-aminomethyl)phenoxy]propionic acid ethyl ester 2-methyl-2-[4-(((1-methyl-3-(4-trifluoromethylphenyl))-pyrazol-5-yl)methyl-N-methyl-aminomethyl)phenoxy]propionic acid 2-methyl-2-[2-methyl-4-(((1-methyl-3-(4-trifluoromethylphenyl))-pyrazol-5-yl)methyl-N-methyl-aminomethyl)phenoxy]propionic acid 2-methyl-2-[2-chloro-4-(((1-methyl-3-(4-trifluoromethylphenyl))-pyrazol-5-yl)methyl-N-methyl-aminomethyl)phenoxy]propionic acid 2-methyl-2-[2-methyl-4-(((1,4-dimethyl-3-(4-trifluoromethylphenyl))-pyrazol-5-yl)methyl-N-methyl-aminomethyl)phenoxy]propionic acid 2-methyl-2-[2-chloro-4-(((1-methyl-3-(4-trifluoromethoxyphenyl))-pyrazol-5-yl)methyl-N-methyl-aminomethyl)phenoxy]propionic acid 2-methyl-2-[2-methyl-4-(((1-methyl-3-(4-trifluoromethylphenyl))-pyrazol-5-yl)methyl-N-propyl-aminomethyl)phenoxy]propionic acid 2-methyl-2-[2-chloro-4-(((1-methyl-3-(4-trifluoromethylphenyl))-pyrazol-5-yl)methyl-N-(propen-2-yl)-aminomethyl)phenoxy]propionic acid 2-methyl-2-[4-(((1-propyl-3-(4-trifluoromethylphenyl))-pyrazol-5-yl)methyl-N-methyl-aminomethyl)phenoxy]propionic acid 2-methyl-2-[2-chloro-4-(((1-propyl-3-(4-trifluoromethylphenyl))-pyrazol-5-yl)methyl-N-methyl-aminomethyl)phenoxy]propionic acid 2-methyl-2-[2-chloro-4-(((1-(propen-2-yl)-3-(4-trifluoromethoxyphenyl))-pyrazol-5-yl)methyl-N-methyl-aminomethyl)phenoxy]propionic acid 2-methyl-2-[2-chloro-4-(((1-(methyl-3-butyl)-3-(4-trifluoromethoxyphenyl))-pyrazol-5-yl)methyl-N-methyl-aminomethyl)phenoxy]propionic acid 2-methyl-2-[4-(((1-benzyl-3-(4-trifluoromethylphenyl))-pyrazol-5-yl)methyl-N-methyl-aminomethyl)phenoxy]propionic acid 2-methyl-2-[2-chloro-4-(((1-benzyl-3-(4-trifluoromethylphenyl))-pyrazol-5-yl)methyl-N-methyl-aminomethyl)phenoxy]propionic acid 2-methyl-2-[2-chloro-4-(((1-benzyl-3-(4-trifluoromethylphenyl))-pyrazol-5-yl)methyl-N-(propen-2-yl)-aminomethyl)phenoxy]propionic acid 2-methyl-2-[2-methyl-4-(((1-(4-methoxybenzyl)-3-(4-trifluoromethylphenyl))-pyrazol-5-yl)methyl-N-methyl-aminomethyl)phenoxy]propionic acid 2-methyl-2-[4-{[(4-methyl-2-[4-trifluoromethylphenyl]-thiazol-5-ylmethyl)-N-methyl-amino]methyl}phenoxy]propionic acid 2-methyl-2-[2-methyl-4-{[(4-methyl-2-[4-trifluoromethylphenyl]-thiazol-5-ylmethyl)-N-methyl-amino]methyl}phenoxy]propionic acid 2-methyl-2-[2-chloro-4-{[(4-methyl-2-[4-trifluoromethylphenyl]-thiazol-5-ylmethyl)-N-methyl-amino]methyl}phenoxy]propionic acid 2-methyl-2-[4-{[(4-methyl-2-[4-trifluoromethylphenyl]-thiazol-5-ylmethyl)-N-(2,2,2-trifluoroethyl)-amino]methyl}phenoxy]propionic acid 2-methyl-2-[2-methyl-4-{[(4-methyl-2-[4-trifluoromethylphenyl]-thiazol-5-ylmethyl)-N-(2,2,2-trifluoroethyl)-amino]methyl}phenoxy]propionic acid 2-methyl-2-[4-{[(4-methyl-2-[4-trifluoromethylphenyl]-thiazol-5-ylmethyl)-N-(propen-2-yl)-amino]methyl}phenoxy]propionic acid 2-methyl-2-[2-methyl-4-{[(4-methyl-2-[4-trifluoromethylphenyl]-thiazol-5-ylmethyl)-N-(propen-2-yl)-amino]methyl}phenoxy]propionic acid 2-methyl-2-[4-{[(4-methyl-2-[4-trifluoromethylphenyl]-thiazol-5-ylmethyl)-N-(propyl)-amino]methyl}phenoxy]propionic acid 2-methyl-2-[4-{[(4-methyl-2-[4-trifluoromethylphenyl]-thiazol-5-ylmethyl-N-(2-methoxyethyl)-amino]methyl}phenoxy]propionic acid 2-methyl-2-[2-methyl-4-{[(4-methyl-2-[4-trifluoromethylphenyl]-thiazol-5-ylmethyl)-N-(3-methoxypropyl)-amino]methyl}phenoxy]propionic acid 2-methyl-2-[4-{[(4-methyl-2-[4-trifluoromethylphenyl]-thiazol-5-ylmethyl)-N-(benzyl)-amino]methyl}phenoxy]propionic acid 2-methyl-2-[2-methyl-4-{[(4-methyl-2-[4-trifluoromethylphenyl]-thiazol-5-ylmethyl)-N-(benzyl)-amino]methyl}phenoxy]propionic acid 2-methyl-2-[2-chloro-4-{[(4methyl2-[4-trifluoromethylphenyl]-thiazol-5-ylmethyl)-N-(benzyl)-amino]methyl}phenoxy]propionic acid 2-methyl-2-[2-methyl-4-{[(4-methyl-2-[4-trifluoromethylphenyl]-thiazol-5-ylmethyl)-N-(furan-2-ylmethyl)-amino]methyl}phenoxy]propionic acid 2-methyl-2-[2-methyl-4-((3-(4-trifluoromethyl-phenyl)-[1,2,4]-oxadiazol-5-yl)methyl-N-methyl-aminomethyl)phenoxy]propionic acid 2-methyl-2-[2-chloro-4-((3-(4-trifluoromethyl-phenyl)-[1,2,4]-oxadiazol-5-yl)methyl-N-methyl-aminomethyl)phenoxy]propionic acid 2-methyl-2-[2-chloro-4-((4-(4-trifluoromethyl-phenyl)-thiazol-2-yl)methyl-N-methyl-aminomethyl)phenoxy]propionic acid 2-Methyl-2-(4-{([4-methoxybenzyl]-[4-methyl-2-(4-trifluoromethylphenyl)thiazol-5-ylamino)methyl}-2-methylphenoxy)propionic acid ethyl ester 2-Methyl-2-(4-{([4-methoxybenzyl-[4-methyl-2-(4-trifluoromethylphenyl)thiazol-5-yl]amino)methyl}2-methylphenoxy)propionic acid 2-Methyl-2-(2-methyl-4-{([4-methyl-2-(4-trifluoromethylphenyl)thiazol-5-yl]thiophen-2-ylmethylamino)methyl}phenoxy)propionic acid ethyl ester 2-Methyl-2-(2-methyl-4-{([4-methyl-2-(4-trifluoromethylphenyl)thiazol-5-yl]thiophen-2-ylmethylamino)methyl}phenoxy)propionic acid 2-Methyl-2-(2-methyl-4-{([4-methyl-2-(4-trifluoromethylphenyl)thiazol-5-yl]furan-2-ylmethylamino)methyl}phenoxy)propionic acid ethyl ester 2-Methyl-2-(2-methyl-4-{([4-methyl-2-(4-trifluoromethylphenyl)thiazol-5-y]furan-2-ylmethylamino)methyl}phenoxy)propionic acid 2-Methyl-2-(2-methyl-4-{([4-methyl-2-(4-trifluoromethylphenyl)thiazol-5-yl][2-methoxybenzyl]amino)methyl}phenoxy)propionic acid ethyl ester 2-Methyl-2-(2-methyl-4-{([4-methyl-2-(4-trifluoromethylphenyl)thiazol-5-yl][2-methoxybenzyl]amino)methyl}phenoxy)propionic acid 2-Methyl-2-(2-methyl-4-{([4-methyl-2-(4-trifluoromethylphenyl)thiazol-5-yl][3-methoxybenzyl]amino)methyl}phenoxy)propionic acid ethyl ester 2-Methyl-2-(2-methyl-4-{([4-methyl-2-(4-trifluoromethylphenyl)thiazol-5-yl][3-methoxybenzyl]amino)methyl}phenoxy)propionic acid 2-Methyl-2-(2-methyl-4-{(]4-methyl-2-(4-trifluoromethylphenyl)thiazol-5-yl][2-fluorobenzyl]amino)methyl}phenoxy)propionic acid ethyl ester 2-Methyl-2-(2-methyl-4-{([4-methyl-2-(4-trifluoromethylphenyl)thiazol-5-yl][2-fluorobenzyl]amino)methyl}phenoxy)propionic acid 2-Methyl-2-(2-methyl-4-{([4-methyl-2-(4-trifluoromethylphenyl)thiazol-5-yl][2-chlorobenzyl]amino)methyl}phenoxy)propionic acid ethyl ester 2-Methyl-2-(2-methyl-4-{([4-methyl-2-(4-trifluoromethylphenyl)thiazol-5-yl][2-chlorobenzyl]amino)methyl}phenoxy)propionic acid 2-Methyl-2-(2-methyl-4-{([4-methyl-2-(4-trifluoromethylphenyl)thiazol-5-yl][methyl]amino)methyl}phenoxy)propionic acid ethyl ester 2-Methyl-2-(2-methyl-4-{([4-methyl-2-(4-trifluoromethylphenyl)thiazol-5-yl][methyl]amino)methyl}phenoxy)propionic acid 2-Methyl-2-(2-methyl-4-{([2-methyl-5-(4-trifluoromethylphenyl)-2H-pyrazol-3-yl][2-fluorobenzyl]amino)methyl}phenoxy)propionic acid ethyl ester 2-Methyl-2-(2-methyl-4-(([2-methyl-5-(4-trifluoromethylphenyl)-2H-pyrazol-3-yl][2-fluorobenzyl]amino)methyl}phenoxy)propionic acid 2-Methyl-2-(2-methyl-4-{([2-methyl-5-(4-trifluoromethylphenyl)-2H-pyrazol-3-yl][2-methoxybenzyl]amino)methyl}phenoxy)propionic acid ethyl ester 2-Methyl-2-(2-methyl-4-{([2-methyl-5-(4-trifluoromethylphenyl)-2H-pyrazol-3-yl][2-methoxybenzyl]amino)methyl}phenoxy)propionic acid Those skilled in the art will recognize that stereocenters exist in compounds of formula (I). Accordingly, the present invention includes all possible stereoisomers and geometric isomers of formula (I) and includes not only racemic compounds but this invention is also intended to cover each of these isomers in their racemic, enriched, or purified forms. When a compound of formula (I) is desired as a single enantiomer, it may be obtained either by resolution of the final product or by stereospecific synthesis using an optically active catalyst or a catalytic system with optically active ligands or isomerically pure starting material or any convenient intermediate. Resolution of the final product, an intermediate or a starting material may be effected by any suitable method known in the art. See, for example, Stereochemistry of Carbon Compounds by E. L. Eliel (Mcgraw Hill, 1962) and Tables of Resolving Agents by S. H. Wilen. Additionally, in situations where tautomers of the compounds of formula (I) are possible, the present invention is intended to include all tautomeric forms of the compounds. In some of these chiral compounds the activities at the various PPAR receptors varies between the S and R isomers. Which of these isomers is preferred depends on the particular desired utility of the compound. In other words, even with the same compound, it is possible that the S isomer will be preferred for some uses, while the R isomer will be preferred for others.

The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPARalpha in the binding assay described below, and which achieve at least 50% activation of the relevant PPAR relative to the appropriate indicated positive control in the transfection assay described below at concentrations of $10^{-5}$ M or less. More preferably, the agonists of this invention achieve 50% activation of at least one human PPAR in the relevant transfection assay at concentrations of $10^{-6}$ M or less. Preferably, the compounds of formula (I) are hPPAR agonists. More preferably the compounds are hPPARδ agonists. Most preferably they are selective agonists or PPARδ, dual agonists of hPPARδ and hPPARα, or pan agonists.

It will also be appreciated by those skilled in the art that the compounds of the present invention may also be utilised in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvents". For example, a complex with water is known as a "hydrate". Solvates of the compound of formula (I) are within the scope of the invention. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier, which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma, PPAR alpha or PPAR alpha/gamma agonists (for example thiazolidinediones such as e.g. Pioglitazone and Rosiglitazone). The compounds may also be used in combination with antihypertensive agents such as angistensin antagonists e.g. telmisartan, calcium channel antagonists e.g. lacidipine and ACE inhibitors e.g. enalapril. The invention thus provides in a further aspect the use of a combination comprising a compound of formula (I) with a further therapeutic agent in the treatment of a hPPAR mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

There is further provided processes for the preparation of compounds of formula (1). Unless otherwise indicated all definitions are as above. Compounds of this invention may conveniently be prepared as illustrated below using intermediates described below variety of commercially or chemise known ingredients.

Compounds of formula (I) may be prepared according to the following scheme 1 below:

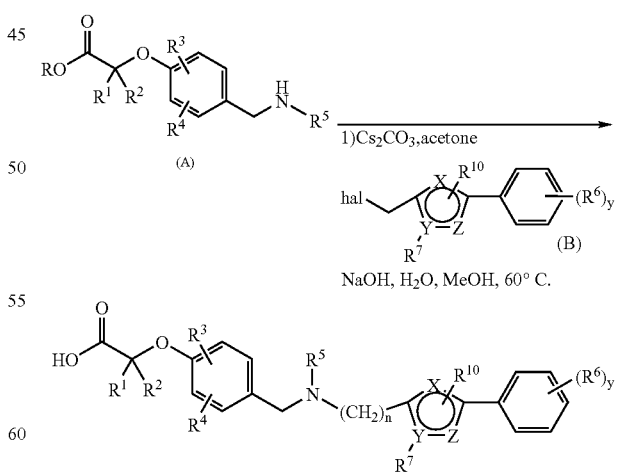

In Scheme 1 above, R in moiety (A) may represent H or a suitable protecting group, e.g. $C_{1-6}$ alkyl, more preferably chlorine or bromine. "hal" in moiety (B) represents a halogen more preferably Cl or Br.

Compounds at moiety (A) may be prepared by Scheme 2 depicted below:
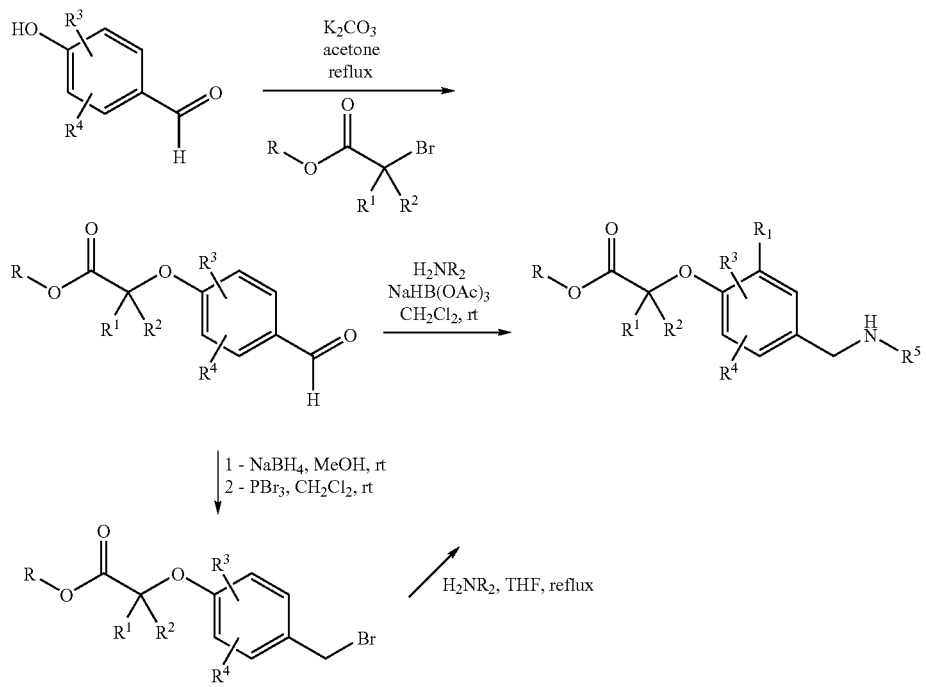
Compounds of moiety (B) when the heterocyclic group is a thiazole ring may be prepared, e.g., as shown in Scheme 3 below:
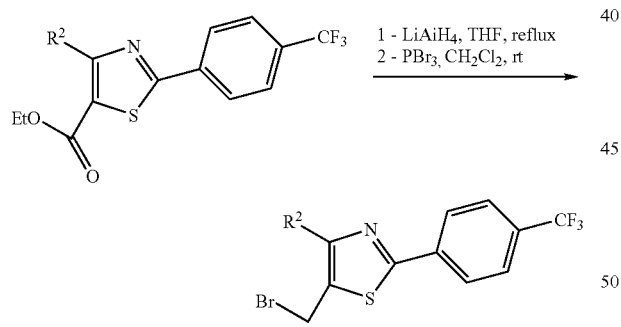
Compounds of moiety (B) wherein heterocyclic moiety is a pyrazole group may be synthesised according to Scheme 4 below:
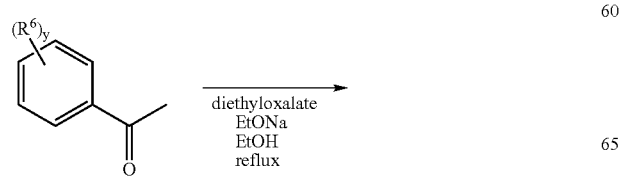
-continued
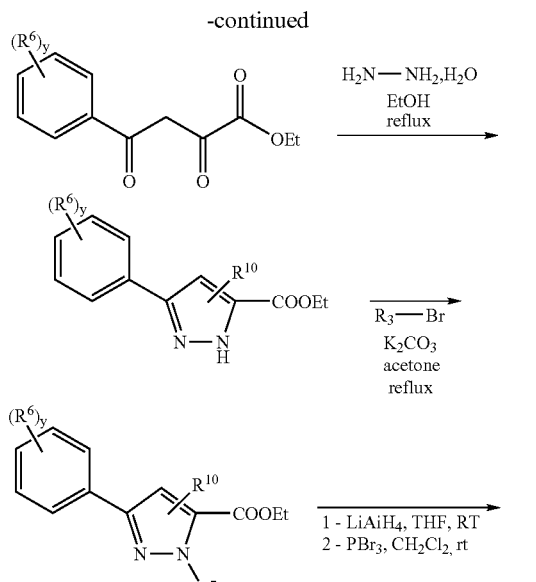

The following illustrates Intermediates and Examples of Formula 1 which should not be construed as constituting a limitation thereto.

The structures of the compounds were confirmed either by nuclear magnetic resonance (NMR) or mass spectrometry (MS). 1H NMR spectra were recorded on a Brucker 300 MHz spectrometer at ambient temperature. NMR shifts (δ) are given in parts per million (ppm), "mp" is melting point and is given in ° C. Column chromatography was carried out using the technique described by W. C. Still et al., J. Org. Chem. 1978, 43, 2923–2925 on Merck silica gel 60 (40–63 µM).

Compounds used as starting materials are either commercially available compounds or known compounds.

Abbreviations:
tlc: thin layer chromatography
e.e.: enantiomeric excess
DMSO-$d_6$: deutorated dimethylsulfoxide
$CDCl_3$: deutorated chloroform
$CD_3OD$: deutorated methanol
$C_6H_{12}$: cyclohexane
DCC: dicycohexylcarbodiimide
DMAP: 4-dimethylaminopyridine
DMF: N,N-dimethylformamide
$Et_2O$: diethylether
EtOAc: Ethylacetate
MeOH: Methanol
PBu3: Tributylphosphine
PCC: Pyridinium chlorochromate
Rf: retention fraction
Rt: retention time
TMAD: Azodicarboxylic acid bis[dimethylamide]
THF: tetrahydrofuran
min: minutes
br: broad
s: singlet
d: doublet
dd: doublet of doublet
t: triplet
q: quartet
m: multiplet

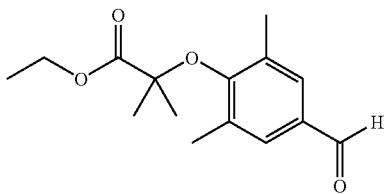

INTERMEDIATE 1

2-(4-Formyl-2,6-dimethyl-phenoxy)2-methyl-propionic acid ethyl ester

A solution of 3,5-Dimethyl-4-hydroxybenzaldehyde (20 g, 0.133 mol) in 3-Methyl-2-butanone (400 mL) was treated with $Cs_2CO_3$ (86.9 g, 2 eq.) and Ethyl-2-bromoisobutyrate (39.2 L, 2 eq.). The resulting mixture was stirred at reflux for 36 hours. After cooling to rt the reaction mixture was filtered off. The cake was washed with ethyl acetate. The filtrate was evaporated off and the residue was diluted with ethyl acetate (1 L), washed with water (500 mL) and then with NaOH 1N (500 mL). The organic layer was drying over $Na_2SO_4$ and filtration evaporation gave the title compound (31.8 g, 0.12 mol) as a brown oil in a 90% yield.

$^1$H NMR (300 MHz, $CDCl_3$) δ: 9.8 (s, 1H), 7.4 (s, 2H), 4.2 (q, 2H), 2.2 (s, 6H), 1.35 (s, 6H), 1.2 (t, 3H). non enregistré

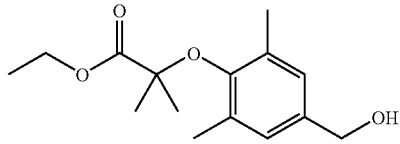

INTERMEDIATE 2

2-(4-Hydroxy-2,6-dimethyl-phenoxy)-2-methyl-propionic acid ethyl ester

A solution of intermediate 1 (26 g, 0.1 mol) in ethanol (150 mL) was treated at rt with $NaBH_4$ (3.6 g, 0.95 eq.). The resulting mixture was stirred at 50° C. for 15 min. and water was added. After evaporation, the residue was diluted in ethyl acetate, washed with water, drying over $Na_2SO_4$. Filtration and evaporation gave the title compound (25 g, 0.093 mol) as a brown oil in a 94% yield which was directly used in the next step without purification.

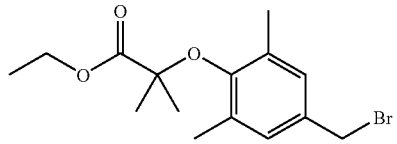

INTERMEDIATE 3

2-(4-Bromomethyl-2.6-dimethyl-phenoxy)-2-methyl-propionic acid ethyl ester

A solution of intermediate 2 (24 g, 73 mmol) in DCM (1 L) was treated with $PBr_3$ (excess). The resulting mixture was stirred at rt for one hour and water was added. After extraction with DCM, the organic layer was drying over $Na_2SO_4$, filtered off and evaporated. The residue was purified by flash chromatography using DCM to give the title compound (25 g, 0.053 mol) as a yellow oil in a 72% yield.

$^1$H NMR (300 MHz, $CDCl_3$) δ: 7.00 (s, 2H), 4.39 (s, 2H), 4.27 (q, 2H), 2.18 (s, 6H), 1.46 (s, 6H), 1.34 (t, 3H).

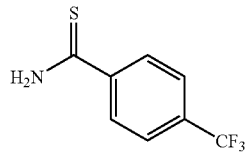

INTERMEDIATE 4

4-Trifluoromethyl-thiobenzamide

A solution of α,α,α-trifluoro-p-tolunitrile (603.5 g, 3.53 mol) in dry DMF (2 L) under $N_2$ was heated at 70° C. and the Thioacetamide (505 g, 1.9 eq.) was added. The reaction mixture was treated with HCl gas before 15 minutes and was stirred at 95° C. for 6 hours. This treatment was operated 3 times and the mixture was stirred at rt for 24 hours. After cooling at 0° C., water was added and the residue was extracted with diethyl ether (4*1 L). The organic layer was washed with water (3*1 L), dried over Na₂SO₄ and then evaporated off. The brownish powder was washed with pentane (3 L) to give the title compound (530.3 g, 2.59 mol) as brown solid in a 73% yield.

GC/MS: M⁺ C₈H₆F₃NS 205

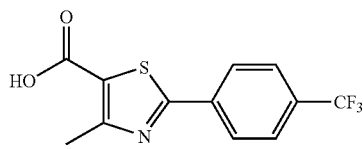

INTERMEDIATE 5

4-Methyl-2-(4trifluoromethyl-phenyl)thiazole-5-carboxylic acid

To a solution of intermediate 4 (20 g, 0.1 mol) in EtOH (300 mL) was added the 2-Chloro-3-oxo-butyric acid ethyl ester (14 mL, 1 eq.).The mixture was stirred to reflux overnight to give the 4-Methyl-2-(4-trifluoromethyl-phenyl)-thiazole-5-carboxylic acid ethyl ester and a 1N NaOH solution (120 mL, 1.2 eq) was added and heating for 3 hours. After evaporation the residue was diluted with water (50 mL) and 1N HCl solution (120 mL). The precipitate was filtered off to give the title compound (26 g, 0.099 mol) as powder in a quantitative yield.

¹H NMR (300 MHz, CDCl₃) δ: 8.29 (d, 2H), 7.97 (d, 2H), 2.80 (s, 3H).

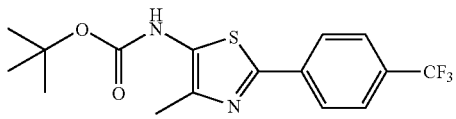

INTERMEDIATE 6

[4Methyl-2-(4-trifluoromethyl-phenyl)thiazol-5-yl]-carbamic acid tert-butyl ester To a solution of intermediate 5 (10 g, 38.3 mmol) in t-BuOH (100 mL) was added Phosphorazidic acid diphenyl ester (20 mL) and triethyl amine (20 mL). The reaction mixture was stirred to reflux for 2 hours, the precipitate was filtered off and washed with EtOH to give the title compound (8.5 g, 23.7 mmol) as white crystals in a 62% yield.

¹H NMR (300 MHz, DMSO) 10.22 (s, 1H), 8.17 (d, 2H), 7.93 (d, 2H), 2.65 (s, 3H), 1.65 (s, 9H).

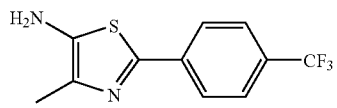

INTERMEDIATE 7

4-Methyl-2-(4-trifluoromethyl-phenyl)thiazol-5-ylamine

To a suspension of intermediate 6 (14 g, 39 mmoL) in DCM (200 mL) was added trifluoroacetic acid (100 mL) and the reaction mixture was stirred at rt for 1 hour. After evaporation, the residue was diluted with water (150 mL) and concentrated NaOH and refluxed for 1 hour. After cooling, filtration give the title compound (7.5 g, 0.029 mol) as ochre powder in a 75% yield.

MP: 146–148° C. GC/MS: m/z 258

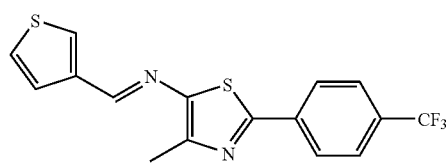

INTERMEDIATE 8

[4-Methyl-2-(4-trifluoromethyl-phenyl)-thiazol-5-yl]-thiophen-3-ylmethylene-amine A solution of intermediate 7 (2.58 g, 10 mmol) and Thiophene-3-carbaldehyde (1.12 g, 1 eq) in EtOH (10 mL) was stirred to reflux overnight. After cooling the precipitate was filtered off, to give the title compound (3.25 g, 8.3 mmol) as yellow crystals in a 92% yield.

¹H NMR (300 MHz, CDCl₃) δ: 8.60 (s, 1H), 8.30 (d, 1H), 8.16 (d, 2H), 7.91 (d, 2H), 7.74 (m, 1H), 7.71 (d, 1H), 2.60 (s, 3H).

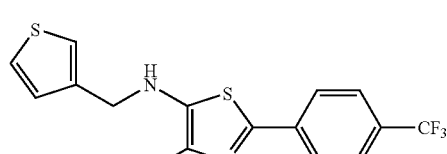

INTERMEDIATE 9

[4Methyl-2-(4-trifluoromethyl-phenyl)-thiazol-5-yl]-thiophen-3-ylmethyl-amine

To a solution of intermediate 8 (3.2 g, 9.09 mmol) in ethanol (20 mL) was added sodium borohydride (350 mg, 1 eq.) and the reaction was stirred to reflux for 15 min. After cooling, the reaction was taken up in water and extracted with DCM. The organic layer was drying over Na₂SO₄ and filtrated off to give the title compound (3.18 g, 9.0 mmol) in a 97% yield.

¹H NMR (300 MHz, CDCl₃) δ: 7.86 (d, 2H), 7.59 (d, 2H), 7.34 (m, 1H), 7.24 (s, 1H), 7.09 (d, 1H), 4.34 (s, 2H), 2.30 (s, 3H).

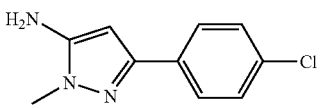

INTERMEDIATE 10

5-(4-Chloro-phenyl)2-methyl-2H-pyrazol-3-ylamine

A solution of 3-(4-Chloro-phenyl)-3-oxo-propionitrile (1.8 g, 10 mmol) and N-Methylhydrazine (1 mL, excess) in EtOH (30 mL) was stirred to reflux 3 hours. After cooling the precipitate was filtered off, to give the title compound (950 mg, 4.6 mmol) as white crystals in a 46% yield.
MP: 150° C.

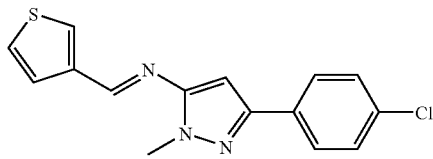

INTERMEDIATE 11

[5-(4-Chloro-phenyl)-2-methyl-2H-pyrazol-3-yl]1-thiophen-3-ylmethylene-amine

The same method was employed as in the preparation of intermediate 8 but starting from intermediate 10 (2.1 g, 10 mmol) to give the title compound as crystals (1.95 g, 6.5 mmol) in a 65% yield.
MP: 130° C.

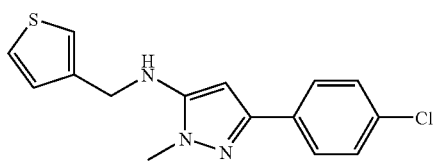

INTERMEDIATE 12

[5-(4Chloro-Phenyl)2-methyl-2pyrazol-3-yl]-thiophen-3-ylmethyl-amine

The same method was employed as in the preparation of intermediate 9 but starting from intermediate 11 (1.9 g, 6.3 mmol) to give the title compound as white crystals (1.9 g, 6.2 mmol) in a 98% yield.
MP: 95° C.

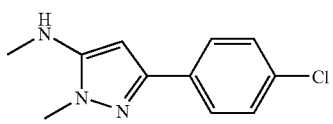

INTERMEDIATE 13

[5-(4-Chloro-phenyl)-2-methyl-2H-pyrazol-3-yl]-methyl-amine

A solution of intermediate 10 (3.5 g, 16.9 mmol) in formic acid (40 mL) was stirred to reflux 2 hours. After cooling, the reaction mixture was taken up into water and the precipitate was filtered off, to give N-[5-(4-Chloro-phenyl)-2H-pyrazol-3-yl]-formamide (3 g, 12.7 mmol) as white crystals in a 75% yield.
MP: 151° C.

This product was treated with LAH (1M/THF, 40 mL) in THF (30 mL) and the reaction mixture was stirred at rt for 3 hours. After cooling, water was added and filtered over a bed of celite to give after evaporation the title compound (2.3 g, 10.3 mmol) as pink crystals in a 81% yield.
MP: 112° C. GC/MS: m/z 221

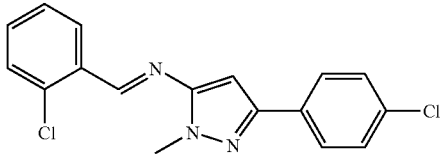

INTERMEDIATE 14

(2-Chloro-phenyl)-[5-(4chloro-phenyl)-2-methyl-2H-pyrazol-3-yl]-methyleneamine

The same method was employed as in the preparation of intermediate 8 but starting from intermediate 10 (4.15 g, 20 mmol) and 2-chlorobenzaldehyde to give the title compound as clear green crystals (2.22 g, 6.73 mmol) in a 34% yield.
$^1$ H NMR (300 MHz, DMSO) δ: 8.90 (s, 1H), 8.05 (m, 2H), 7.55 (d, 2H), 7.20 (m, 3H), 7.15 (d, 2H), 6.35 (s, 1H), 3.80 (s, 3H).

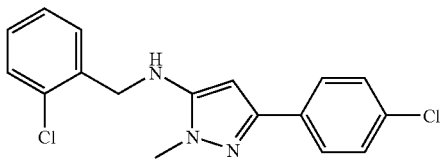

INTERMEDIATE 15

(2-Chloro-benzyl)-[5(4chloro-phenyl)2-methyl-2H-pyrazol-3-yl]-methylamine

The same method was employed as in the preparation of intermediate 9 but starting from intermediate 14 (2.20 g, 6.67 mmol) to give the title compound as white crystals (2.0 g, 6.02 mmol) in a 90% yield.
$^1$H NMR (300 MHz, DMSO) δ: 7.65 (d, 2H), 7.50 (m, 2H), 7.35 (d, 2H), 7.30 (m, 2H), 6.25 (t, 1H), 5.75 (s, 1H), 4.35 (d, 2H), 3.65 (s, 3H).

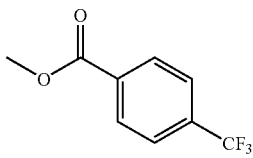

INTERMEDIATE 16

4-Trifluoromethyl-benzoic acid methyl ester

To a solution of 4-Trifluoromethyl-benzoic acid (20 g, 0.112 mol) in toluene (200 mL) was added thionyl chloride (40 mL, 0.562 mol) and stirred to reflux for 3 hours. The reaction mixture was evaporated off and the residue was dissolved in toluene (100 mL) and triethylamine (30 mL) was added. The mixture was stirred at 60° C. for 3 hours and at 30° C. overnight. After evaporation, the product was diluted with DCM, washed with water, drying over $Na_2SO_4$, filtered and evaporated off. The title compound (13.89 g, 68 mmol) was obtained in a 60% yield.
G/MS: m/z 204

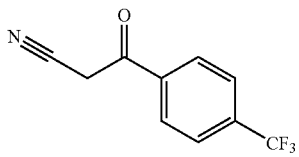

INTERMEDIATE 17

3-Oxo-3-(4trifluoromethyl-phenyl)propionitrile

To a solution of intermediate 16 (5 g, 24.5 mmol) in chlorobenzene (150 mL) was added acetonitrile (30.6 mmol, 1.25 eq) and the mixture was stirred at rt for 30 min under Ar. Then sodium methylate (1.32 g, 1 eq) was added and the reaction was stirred at 110° C. overnight. After cooling, water was added and extracted with ether (30 mL). The aqueous layer was acidified with 1N solution of HCl until pH=6 and the product was extracted with ether. Drying over $Na_2SO_4$, filtration and evaporation gave the title compound (800 mg, 3.76 mmol) in a 15% yield.
$^1$H NMR (300 MHz, DMSO) δ: 8.04 (d, 2H), 7.80 (d, 2H), 4.10 (s, 2H).

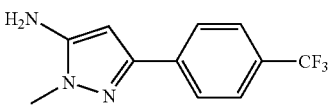

INTERMEDIATE 18

2-Methyl-5-(4-trifluoromethyl-phenyl)-2H-pyrazol-3-ylamine

The same method was employed as in the preparation of intermediate 10 but starting from intermediate 17 (30 g, 0.141 mol) to give the title compound as white crystals (18.25 g, 0.79 mol) in a 56% yield after crystallisation from $iPr_2O$.

$^1$H NMR (300 MHz, DMSO) δ: 7.94 (d, 2H), 7.78 (d, 2H), 5.88 (s, 2H), 3.68 (s, 3H).

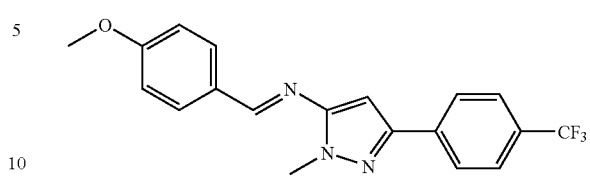

INTERMEDIATE 19

(4Methoxy-benzylidene)-[2-methyl-5-(4-trifluoromethyl-phenyl)-2H-pyrazol-3-yl]-amine The same method was employed as in the preparation of intermediate 8 but starting from intermediate 18 (2.3 g, 10 mmol) and 4-Methoxy-benzaldehyde (1.36 g, 1 eq) to give the title compound as powder (2.6 g, 7.2 mmol) in a 72% yield.
$^1$H NMR (300 MHz, CDCl$_3$) δ: 8.58 (s, 1H), 7.92 (m, 4H), 7.63 (d, 2H), 6.99 (d, 2H), 6.53 (s, 1H), 4.01 (s, 3H), 3.88 (s, 3H).

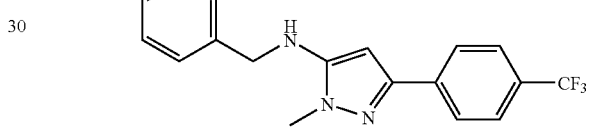

INTERMEDIATE 20

(4-Methoxy-benzyl)-[2-methyl-5-(4trifluoromethyl-phenyl)-2H-pyrazol-3-yl]-amine

The same method was employed as in the preparation of intermediate 9 but starting from intermediate 19 (2.6 g, 7.2 mmol) to give the title compound as white crystals (2.6 g, 7.2 mmol) in a 65% yield.
$^1$H NMR (300 MHz, CDCl$_3$) δ: 7.83 (d, 2H), 7.59 (d, 2H), 7.32 (d, 2H), 6.91 (d, 2H), 5.85 (s, 1H), 4.24 (s, 2H), 3.81 (s, 3H), 3.68 (s, 3H).

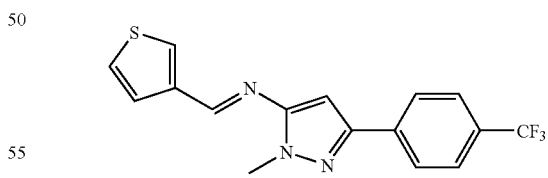

INTERMEDIATE 21

[2-Methyl-5-(4trifluoromethyl-phenyl)-2H-pyrazol-3-yl]-thiphen-3-ylmethylene-amine The same method was employed as in the preparation of intermediate 8 but starting from intermediate 18 (2.3 g, 10 mmol) and to give the title compound as powder (1.2 g, 3.6 mmol) in a 36% yield.

$^1$H NMR (300 MHz, CDCl$_3$) δ: 8.65 (s, 1H), 7.90 (d, 2H), 7.85 (d, 1H), 7.69 (d, 1H), 7.62 (d, 2H), 7.42 (m, 1H), 6.53 (s, 1H), 3.99 (s, 3H).

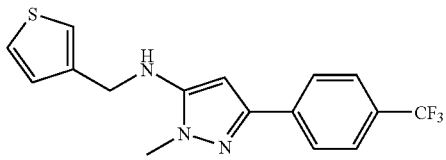

INTERMEDIATE 22

[2-Methyl-5-(4-trifluoromethyl-phenyl)-2H-pyrazol-3-yl]-thiphen-3-ylmethyl-amine The same method was employed as in the preparation of intermediate 9 but starting from intermediate 21 (1.2 g, 3.6 mmol), to give the title compound as white crystals (1.2 g, 3.5 mmol) in a quantitative yield.
$^1$H NMR (300 MHz, CDCl$_3$) δ: 7.83 (d, 2H), 7.61 (d, 2H), 7.34 (m, 1H), 7.24 (m, 1H), 7.12 (d, 1H), 5.86 (s, 1H), 4.33 (s, 2H), 3.69 (s, 3H).

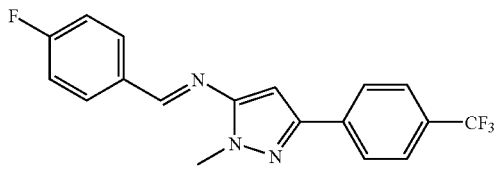

INTERMEDIATE 23

(4-Fluoro-benzylidene)-[2-methyl-5-(4-trifluoromethyl-phenyl)-2H-pyrazol-3-yl]-amine The same method was employed as in the preparation of intermediate 8 but starting from intermediate 18 (2.3 g, 10 mmol), to give the title compound as white powder.
$^1$H NMR (300 MHz, DMSO) δ: 8.92 (s, 1H), 8.08–8.00 (m, 4H), 7.79 (d, 2H), 7.40 (t, 2H), 7.06 (s, 1H), 3.96 (s, 3H).

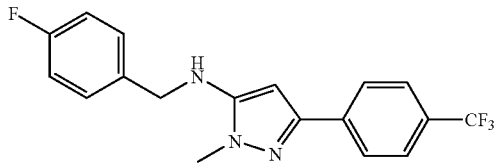

INTERMEDIATE 24

(4-Fluoro-benzyl)-[2-methyl-5-(4-trifluoromethyl-phenyl)-2H-pyrazol-3-yl]-amine

The same method was employed as in the preparation of intermediate 9 but starting from intermediate 23, to give the title compound as crystals (2.4 g, 6.9 mmol) in a 68% yield.
$^1$H NMR (300 MHz, CDCl$_3$) δ: 7.82 (d, 2H), 7.59 (d, 2H), 7.36 (m, 2H), 7.05 (t, 2H), 5.82 (s, 1H), 4.28 (s, 2H), 3.71 (s, 3H).

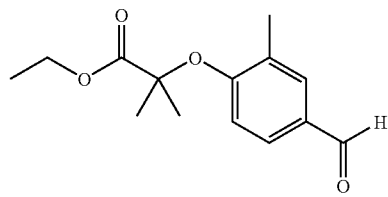

INTERMEDIATE 25

2-(4-Formyl-2-methyl-phenoxy)-2-methyl-propionic acid ethyl ester

The same method was employed as in the preparation of intermediate 1 but starting from 3-Methyl-4-hydroxybenzaldehyde and gave the title compound in a 86% yield after purification by flash chromatography using DCM as eluent.
GC/MS: m/z 250

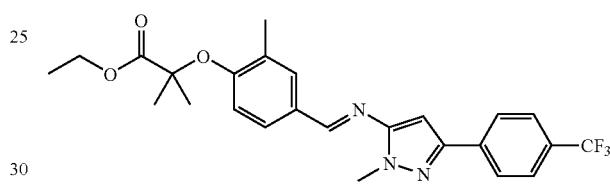

INTERMEDIATE 26

2-(4-{[5-(4-Chloro-phenyl)-2-methyl-2H-pyrazol-3-ylimino]-methyl}-2-methyl-phenoxy)-2-methyl-propionic acid ethyl ester To a solution of intermediate 25 (2.5 g, 10 mmol) in ethanol (50 mL) was added intermediate 10 (2.1 g, 1 eq) and the solution was stirred to reflux overnight. After evaporation the residue was precipitated in diisopropyl ether and after filtration the solid was crystallised from ethanol. The title compound was obtained as white crystals (2.5 g, 5.7 mmol) in a 57% yield.
MP: 130° C. $^1$H NMR (300 MHz, CDCl$_3$) δ: 8.51 (s, 1H), 7.75 (m, 3H), 7.57 (d, 1H), 7.36 (d, 2H), 6.67 (d, 1H), 6.43 (s, 1H), 4.24 (q, 4H), 3.98 (s, 3H), 2.30 (s, 3H), 1.66 (s, 6H), 1.23 (t, 3H).

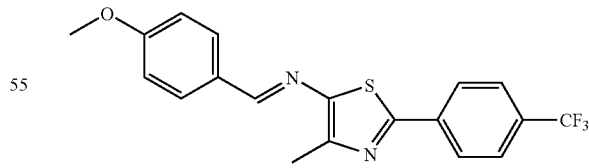

INTERMEDIATE 27

(4-Methoxy-benzylidene)-[4-methyl-2-(4-trifluoromethyl-phenyl)-thiazol-5-yl]-amine The same method was employed as in the preparation of intermediate 8 but starting from intermediate 7 (2.6 g, 10 mmol) and 4-Methoxy-benzaldehyde (1.36 g, 1 eq) to give the title compound which was directly used in the next step without analysis.

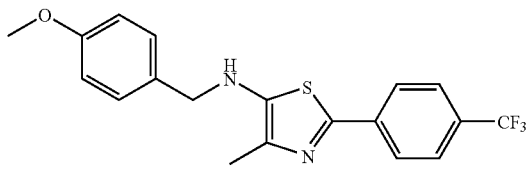

INTERMEDIATE 28

(4-Methoxy-benzyl)-[4-methyl-2-(4-trifluoromethyl-phenyl)-thiazol-5-yl]-amine

The same method was employed as in the preparation of intermediate 9 but starting from intermediate 27 to give the title compound (3.10 g, 8.2 mmol) as a yellow powder in a 82% yield.

$^1$H NMR (300 MHz, DMSO) δ: 7.93 (d, 2H), 7.83 (d, 2H), 7.43 (d, 2H), 7.06 (d, 2H), 6.82 (t, 1H), 4.39 (d, 2H), 3.86 (s, 3H), 2.41 (s, 3H).

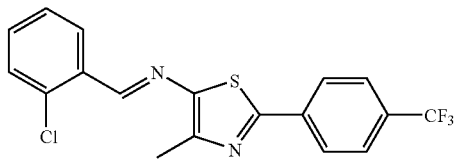

INTERMEDIATE 29

(2-Chloro-benzylidene)-[4-methyl-2-(4trifluorom-ethyl-phenyl)-thiazol-5-yl]-amine The same method was employed as in the preparation of intermediate 8 but starting from intermediate 7 (2.6 g, 10 mmol) and 2-Chloro-benzaldehyde (1.4 g, 1 eq) to give the title compound which was directly used in the next step without analysis.

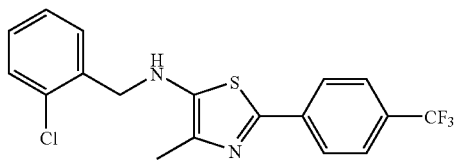

INTERMEDIATE 30

(2-Chloro-benzyl)-[4methyl-2-(4-trifluoromethyl-phenyl)-thiazol-5-yl]-amine

The same method was employed as in the preparation of intermediate 9 but starting from intermediate 29 to give the title compound (3.24 g, 8.5 mmol) in a 84% yield for 2 steps which was directly used in the next step without analysis.

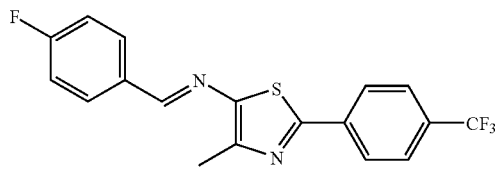

INTERMEDIATE 31

(4-Fluoro-benzylidene)[4-methyl-2-(4trifluorom-ethyl-phenyl)-thiazol-5-yl]-amine The same method was employed as in the preparation of intermediate 8 but starting from intermediate 7 (2.58 g, 10 mmol) and 4-fluoro-benzaldehyde (1.24 g, 1 eq) to give the title compound as yellow crystals.

$^1$H NMR (300 MHz, DMSO) δ: 8.45 (s, 1H), 8.03 (d, 2H), 7.93 (m, 2H), 7.77 (d, 2H), 7.26 (t, 2H), 2.48 (s, 3H).

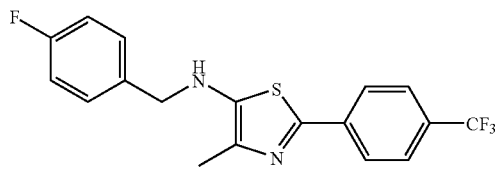

INTERMEDIATE 32

(4-Fluoro-benzyl)-[4-methyl-2-(4-trifluoromethyl-phenyl)thiazol-5yl]-amine

The same method was employed as in the preparation of intermediate 9 but starting from intermediate 31 to give the title compound (2.93 g, 8.5 mmol) as a yellow oil in a 84% yield for 2 steps.

$^1$H NMR (300 MHz, CDCl$_3$) δ: 7.84 (d, 2H), 7.60 (d, 2H), 7.60 (m, 2H), 7.05 (t, 2H), 4.30 (s, 2H), 2.31 (s, 3H).

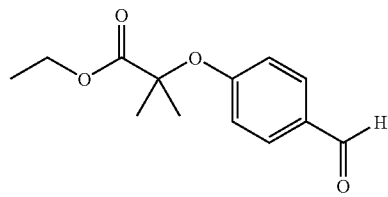

INTERMEDIATE 33

Ethyl-2-methyl-2-(4-formylphenoxy)propanoate

To 4-hydroxybenzaldehyde (20 g, 0.164 mol) in acetone (300 mL) was added K$_2$CO$_3$ (34 g, 1.5 equiv.) and the reaction was stirred at room temperature during 30 minutes. Ethyl 2-bromo-2-methylpropionate (36.2 mL, 1.5 equiv.) was added dropwise and the mixture was heated under reflux during 3 hours. K$_2$CO$_3$ (34 g, 1.5 equiv.) and ethyl 2-bromo-2-methylpropionate (36.2 mL, 1.5 equiv.) were added and the mixture was heated under reflux during 16 hours and then pourred into water and extracted with CH$_2$Cl$_2$ (3×300 mL). The combined organic layers were dried over Na₂SO₄, filtered and the solvent evaporated to afford crude intermediate. After chromatography on silicagel, eluting with cyclohexane/CH₂Cl₂ (6/4, then 8/2) and then with CH₂Cl₂, the titled compound was obtained as an oil (27 g, 69.85%)

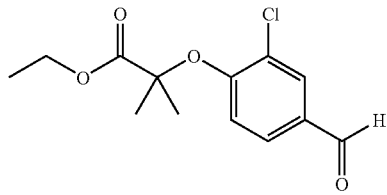

INTERMEDIATE 34

Ethyl-2-methyl-2-((2-chloro4formyl)phenoxy)propanoate

The same method was employed as in the preparation of intermediate 33 but starting from 3-chloro-4-hydroxybenzaldehyde (15 g, 95.80 mmol). The titled compound was obtained as a yellow oil (7 g, 25.91%)

¹H NMR (300 MHz, CDCl₃): δ 9.85 (s, 1H), 7.95 (sd, 1H), 6.85 (d, 1H), 4.25 (q, 2H), 1.7 (s, 6H), 1.25 (t, 3H).

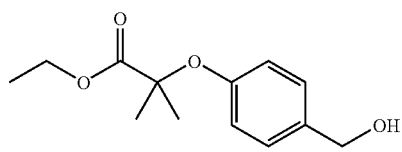

INTERMEDIATE 35

Ethyl-2-methyl-2-((4-hydroxymethyl)phenoxy)propanoate

To a solution of intermediate 33 (2 g, 8.47 mmol) in MeOH (60 mL) was added portionwise NaBH₄ (0.48 g, 1.5 equiv.) and the mixture was stirred at room temperature during 30 minutes and then pourred into water. After extraction with CH₂Cl₂, the organic layer was dried over Na₂SO₄ and then concentrated to dryness to afford the titled compound as a colorless oil (1.92 g, 95.19%)

¹H NMR (300 MHz, CDCl₃): δ 7.2 (d, 2H), 6.85 (d, 2H), 4.6 (s, 2H), 4.25 (q, 2H), 1.6 (s, 6H), 1.25 (t, 3H).

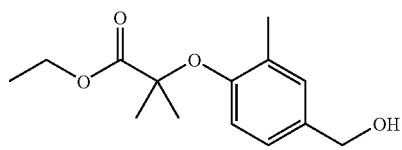

INTERMEDIATE 36

Ethyl-2-methyl-2-((4-hydroxymethyl-2-methyl)phenoxy)propanoate

The same method was employed as in the preparation of intermediate 35 but starting from intermediate 25 (3 g, 12 mmol). The title compound was obtained as an oil (2.93 g, 96.89%).

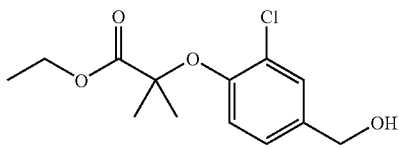

INTERMEDIATE 37

Ethyl-2-methyl-2-((2-chloro-4-hydroxymethyl)phenoxy)propanoate

The same method was employed as in the preparation of intermediate 35 but starting from intermediate 34 (7 g, 25.88 mmol). The title compound was obtained as an oil (5.87 g, 83.24%).

¹H NMR (300 MHz, CDCl₃): δ 7.35 (sd, 1H), 7.1 (dd, 1H), 6.9 (d, 1H), 4.6 (s, 2H), 4.2 (q, 2H), 1.6 (s, 6H), 1.25 (t, 3H).

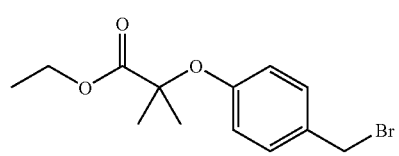

INTERMEDIATE 38

Ethyl-2-methyl-2-((4-bromomethyl)phenoxy)propanoate

To a solution of intermediate 35 (1.9 g, 79.83 mmol) in CH₂Cl₂ (60 mL) was added dropwise phosphorus tribromide (0.25 mL, 0.33 equiv.) and the mixture was stirred at room temperature during 1 hour and then pourred into a saturated solution of Na₂CO₃. After extraction with CH₂Cl₂, the organic layer was dried over Na₂SO₄ and then concentrated to dryness to afford the titled compound as a colorless oil (2.36 g, 98.21%).

¹H NMR (300 MHz, CDCl₃): δ 7.2 (d, 2H), 6.8 (d, 2H), 4.45 (s, 2H), 4.2 (q, 2H), 1.55 (s, 6H); 1.25 (t, 3H).

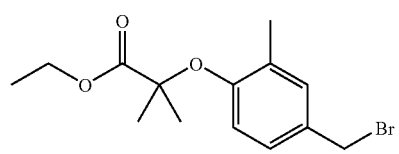

INTERMEDIATE 39

Ethyl-2-methyl-2-((4-bromomethyl-2-methyl)phenoxy)propanoate

The same method was employed as in the preparation of intermediate 38 but starting from intermediate 36 (2.93 g, 11.63 mmol). The title compound was obtained as an oil (3.08 g, 84.1%).

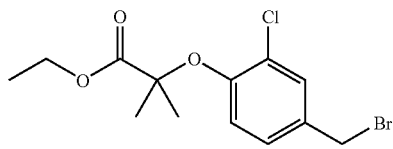

INTERMEDIATE 40

Ethyl-2-methyl-2-((4-bromomethyl-2-chloro)phenoxy)propanoate

The same method was employed as in the preparation of intermediate 38 but starting from intermediate 37 (5.87 g, 21.54 mmol). The title compound was obtained as an oil (6.2 g, 85.79%).

$^1$H NMR (300 MHz, CDCl$_3$): δ 7.4 (sd, 1H), 7.15 (dd, 1H), 6.85 (d, 1H), 4.45 (s, 2H), 4.25 (2H), 1.6 (s, 6H), 1.25 (t, 3H).

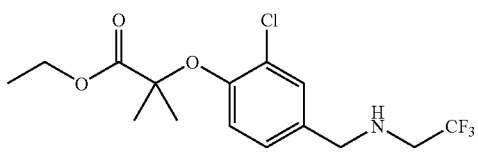

INTERMEDIATE 41

Ethyl-2-methyl-2-[(4-(N-(2,2,2-trifluoroethyl)aminomethyl)phenoxy]-propanoate

To a solution of intermediate 33 (1 g, 4.24 mmol) in CH$_2$Cl$_2$ (50 mL) was added 2,2,2-trifluoroethylamine (0.34 mL, 1 equiv.) and sodium triacetoxy borohydride (1.08 g, 1.2 equiv.) and the mixture was stirred at room temperature overnight and then poured into a saturated solution of NaHCO$_3$. After extraction with CH$_2$Cl$_2$, the organic layer was dried over Na$_2$SO$_4$ and then concentrated to dryness. The residue was purified by chromatography on silicagel eluting with CH$_2$Cl$_2$/MeOH (99/1) to afford the titled compound as a colorless oil (0.62 g, 45.9%).

$^1$H NMR (300 MHz, CDCl$_3$): δ

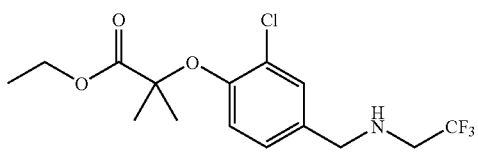

INTERMEDIATE 42

Ethyl-2-methyl-2-[(2-chloro-4-(N-(2,2,2-trifluoroethyl)aminomethyl)-phenoxy]propanoate The same method was employed as in the preparation of intermediate 41 but starting from intermediate 34 (2 g, 7.39 mmol). The title compound was obtained as a colorless oil (1.97 g, 75.37%).

$^1$H NMR (300 MHz, CDCl$_3$): δ 7.35 (sd, 1H), 7.1 (dd, 1H), 6.85 (d, 1H), 4.2 (q, 2H), 3.8 (s, 2H), 3.15 (q, 2H), 1.55 (s, 6H), 1.25 (t, 3H).

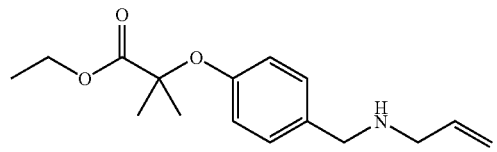

INTERMEDIATE 43

Ethyl-2-methyl-2-[4-(N-(propen-2-yl)aminomethyl)phenoxy]propanoate

The same method was employed as in the preparation of intermediate 41 but starting from intermediate 33 (1 g, 4.24 mmol). The title compound was obtained as a pale yellow oil (0.65 g, 55.38%).

$^1$H NMR (300 MHz, CDCl$_3$): δ 7.2 (d, 2H), 6.8 (d, 2H), 5.9 (m, 1H), 5.1 (m, 2H), 4.2 (q, 2H), 3.7 (s, 2H), 3.25 (d, 2H), 1.6 (s, 6H), 1.25 (t, 3H).

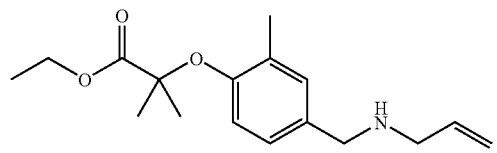

INTERMEDIATE 44

Ethyl-2-methyl-2-[2-methyl-4-(N-(propen-2-yl)aminomethyl)phenoxy]-propanoate

The same method was employed as in the preparation of intermediate 41 but starting from intermediate 25 (2.4 g, 9.6 mmol). The title compound was obtained as a yellow oil (1.8 g, 64.43%).

$^1$H NMR (300 MHz, CDCl$_3$): δ 7.1 (sd, 1H), 6.9 (dd, 1H), 6.6 (d, 1H), 5.9 (m, 1H), 5.1 (m, 2H), 4.25 (q, 2H), 3.7 (s, 2H), 3.25 (d, 2H), 2.2 (s, 3H), 1.55 (s, 6H), 1.25 (t, 3H).

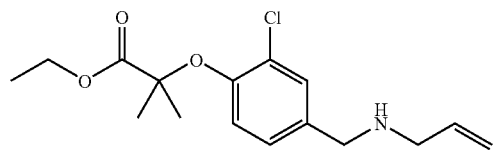

INTERMEDIATE 45

Ethyl-2-methyl-2-[2-chloro-4-(N-(propen-2-yl)aminomethyl)phenoxy]-propanoate

The same method was employed as in the preparation of intermediate 41 but starting from intermediate 34 (3 g, 11.09 mmol). The title compound was obtained as an oil (3 g, 86.84%).

¹H NMR (300 MHz, CDCl₃): δ 7.4 (sd, 1H), 7.1 (dd, 1H), 6.85 (d, 1H), 5.95 (m, 1H), 5.15 (m, 2H), 4.25 (q, 2H), 3.7 (s, 2H), 3.25 (d, 2H), 1.6 (s, 6H), 1.25 (t, 3H).

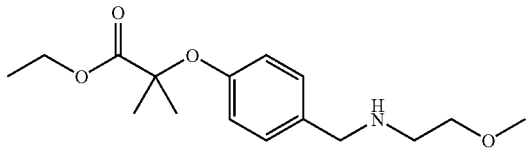

INTERMEDIATE 46

Ethyl-2-methyl-2-[4-(N-(2-methoxyethyll)aminomethyl)phenoxy]propanoate

The same method was employed as in the preparation of intermediate 41 but starting from intermediate 33 (1.36 g, 5.76 mmol). The title compound was obtained as an oil (1.25 g, 73.53%).

¹H NMR (300 MHz, CDCl₃): δ 7.2 (d, 2H), 6.75 (d, 2H), 4.15 (q, 2H), 3.7 (s, 2H), 3.45 (t, 2H), 3.3 (s, 3H), 2.75 (t, 2H), 1.55 (s, 6H), 1.2 (t, 3H).

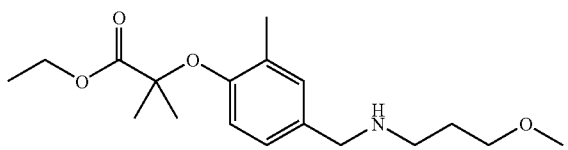

INTERMEDIATE 47

Ethyl-2-methyl-2-[2-methyl-4-(N-(3-methoxypropyl)aminomethyl)phenoxy]-propanoate The same method was employed as in the preparation of intermediate 41 but starting from intermediate 25 (2 g, 8 mmol). The title compound was obtained as a pale yellow oil (1.27 g, 49.15%).

¹ H NMR (300 MHz, CDCl₃): δ 7.1 (sd, 1H), 6.95 (dd, 1H), 6.6 (d, 1H), 4.2 (q, 2H), 3.7 (s, 2H), 3.4 (t, 2H), 3.3 (s, 3H), 2.7 (t, 2H), 2.2 (s, 3H), 1.75 (m, 2H), 1.55 (s, 6H), 1.25 (t, 3H).

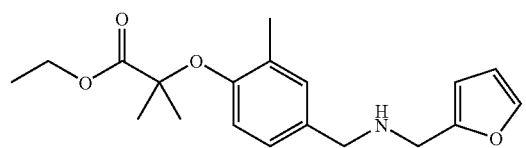

INTERMEDIATE 48

Ethyl-2-methyl-2-[2-methyl-4-N-(furan-2-ylmethyl)aminomethyl)phenoxy]-propanoate The same method was employed as in the preparation of intermediate 41 but starting from intermediate 25 (2 g, 8 mmol). The title compound was obtained as a yellow oil (1.24 g, 46.83%).

¹H NMR (300 MHz, CDCl₃): δ 7.35 (dd, 1H), 7.1 (dd, 1H), 6.95 (dd, 1H), 6.55 (d, 1H), 6.3 (dd, 1H), 6.15 (dd, 1H), 4.2 (q, 2H), 3.75 (s, 2H), 3.65 (s, 2H), 2.2 (s, 3H), 1.55 (s, 6H), 1.2 (t, 3H).

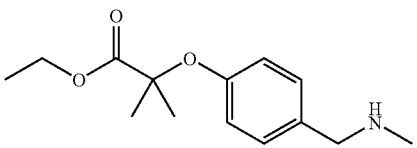

INTERMEDIATE 49

Ethyl-2-methyl-2-[4-(N-(methyl)aminomethyl)phenoxy]propanoate

To a solution of intermediate 38 (2.36 g, 7.84 mmol) in THF (50 mL) was added methylamine 40% in water (10 mL) and the mixture was heated at 50° C. during 30 minutes and then poured into water. After extraction with CH₂Cl₂, the organic layer was dried over Na₂SO₄ and then concentrated to dryness to afford the titled compound as an oil (1.86 g, 94.51%).

¹H NMR (300 MHz, CDCl₃): δ 7.15 (d, 2H), 6.8 (d, 2H), 4.25 (q, 2H), 3.7 (s, 2H), 2.45 (s, 3H), 1.6 (s, 6H), 1.25 (t, 3H).

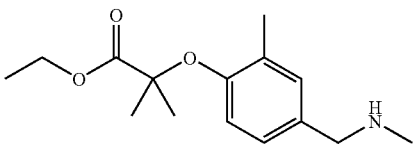

INTERMEDIATE 50

Ethyl-2-methyl-2-[2-methyl4-(N-(methyl)aminomethyl)phenoxy]propanoate

The same method was employed as in the preparation of intermediate 49 but starting from intermediate 39. The title compound was obtained as a yellow oil.

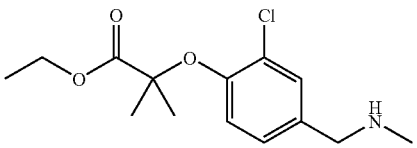

INTERMEDIATE 51

Ethyl-2-methyl-2-[2-chloro4-(N-(methyl)aminomethyl)phenoxy]propanoate

The same method was employed as in the preparation of intermediate 49 but starting from intermediate 40 (2 g, 5.96 mmol). The title compound was obtained as a light yellow oil (0.81 g, 47.6%).

¹H NMR (300 MHz, CDCl₃): δ 7.35 (sd, 1H), 7.1 (dd, 1H), 6.85 (d, 1H), 4.25 (q, 2H), 3.7 (s, 2H), 2.45 (s, 3H), 1.6 (s, 6H), 1.25 (t, 3H).

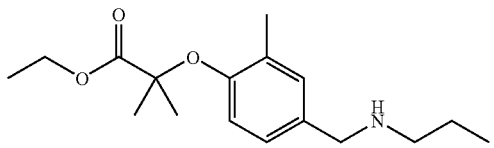

INTERMEDIATE 52

Ethyl-2-methyl-2-[2-methyl-4-(N-propyl)aminomethyl)phenoxy]propanoate

The same method was employed as in the preparation of intermediate 49 but starting from intermediate 39 (1.5 g, 4.76 mmol). The title compound was obtained as an oil (0.9 g, 64.50%).

$^1$H NMR (300 MHz, CDCl$_3$): δ 7.2 (sd, 1H), 7.05 (dd, 1H), 6.6 (d, 1H), 4.25 (q, 2H), 3.65 (s, 2H), 2.55 (t, 2H), 2.25 (s, 3H), 1.6 (s, 6H), 1.6 (m, 2H), 1.3 (t, 3H), 0.95 (t, 3H).

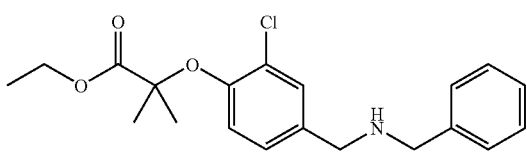

INTERMEDIATE 53

Ethyl-2-methyl-2-[2-chloro-4-(N-(benzyl)aminomethyl)phenoxy]propanoate

The same method was employed as in the preparation of intermediate 49 but starting from intermediate 40 (2 g, 5.96 mmol). The title compound was obtained as an oil (1.6 g, 74.25%).

$^1$H NMR (300 MHz, CDCl$_3$): δ 7.3 (m, 5H), 7.25 (sd, 1H), 7.1 (dd, 1H), 6.85 (d, 1H), 4.25 (q, 23H), 3.8 (s, 2H), 3.7 (s, 2H), 1.6 (s, 6H), 1.25 (t, 3H).

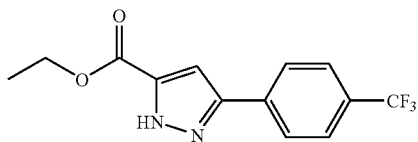

INTERMEDIATE 54

Ethyl-3-(4trifluoromethylphenyl)pyrazole-5-carboxylate

To a solution of 4-trifluoromethylacetophenone (10 g, 53.15 mmol) in EtOH (100 mL) was added portionwise sodium ethoxyde (5.43 g, 79.72 mmol) and the mixture was stirred at room temperature during 20 minutes. Dimethyloxalate (8.16 g, 69.09 mmol) was added and the mixture was heated under reflux during 1 hour and then poured into a solution of HCl 1N. After extraction with CH$_2$Cl$_2$, the organic layer was dried over Na$_2$SO$_4$, and concentrated to dryness. The residue was dissolved in EtOH (100 mL), and hydrazine hydrate (3.1 mL, 63.78 mmol) was added dropwise. The mixture was heated under reflux overnight, then poured into water. After extraction with CH$_2$Cl$_2$, the organic layer was dried over Na$_2$SO$_4$, and concentrated to dryness. The solid residue was crystallised from diisopropyloxyde to afford the titled compound as cream crystals (8.42 g, 55.78%).

Mp: 162° C.

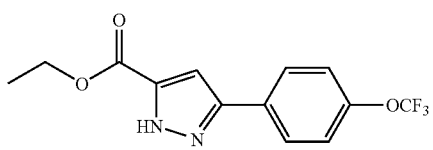

INTERMEDIATE 55

Ethyl-3-(4-trifluoromethoxyphenyl)pyrazole-5-carboxylate

The same method was employed as in the preparation of intermediate 54 but starting from 4-trifluoromethoxy-acetophenone (5 g, 24.51 mmol). The title compound was obtained as yellow solid (5.45 g, 74.12%).

Mp: 155° C.

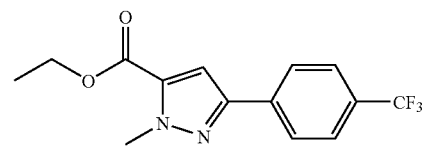

INTERMEDIATE 56

Ethyl-1-methyl-3-(4-trifluoromethylphenyl)pyrazole-5-carboxylate

To a solution of intermediate 54 in acetone was added portionwise K$_2$CO$_3$ and the mixture was stirred at room temperature during 20 minutes. Methyl iodide as then added and the mixture was heated under reflux during hours and then poured into water. After extraction with CH$_2$Cl$_2$, the organic layer was dried over Na$_2$SO$_4$, and concentrated to dryness.

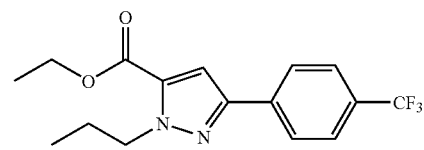

INTERMEDIATE 57

Ethyl-1-propyl-3-(4-trifluoromethylphenyl)pyrazole-5-carboxylate

The same method was employed as in the preparation of intermediate 56 starting from intermediate 54. The title compound was obtained as an oil

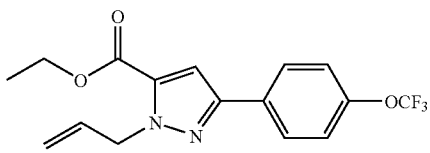

INTERMEDIATE 58

Ethyl-1-(propen-2-yl)-3-(4-trifluoromethoxyphenyl)pyrazole-5-carboxylate

The same method was employed as in the preparation of intermediate 56 but starting from intermediate 55 (1 g, 3.33 mmol). The title compound was obtained as an oil (1 g, 88.24%).

$^1$H NMR (300 MHz, CDCl$_3$): δ 7.85 (d, 2H), 7.25 (d, 2H), 7.15 (s, 1H), 6.1 (m, 1H), 5.25 (d, 2H), 5.2 (m, 2H), 4.35 (q, 2H), 1.3 (t, 3H).

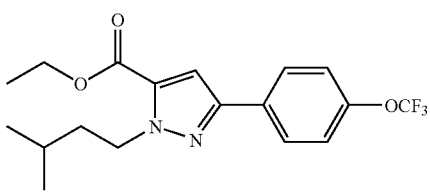

INTERMEDIATE 59

Ethyl-1-(3-methyl-butyl)-3-(4-trifluoromethoxyphenyl)pyrazole-5-carboxylate

The same method was employed as in the preparation of intermediate 56 but starting from intermediate 55 (1.39 g, 4.63 mmol). The title compound was obtained as an orange oil (1.51 g, 88.08%)

$^1$H NMR (300 MHz, CDCl$_3$): δ 7.85 (d, 2H), 7.25 (d, 2H), 7.1 (s, 1H), 4.55 (t, 2H), 4.35 (q, 2H), 1.65 (m, 3H), 1.35 (t, 3H), 0.95 (d, 6H).

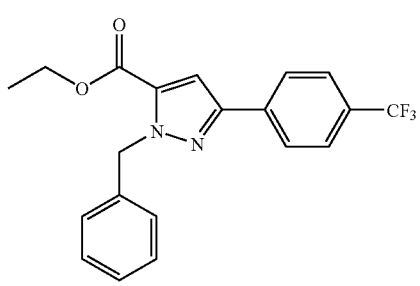

INTERMEDIATE 60

Ethyl-1-benzyl-3-(4-trifluoromethylphenyl)pyrazole-5-carboxylate

The same method was employed as in the preparation of intermediate 56 starting from intermediate 54. The title compound was obtained as an oil

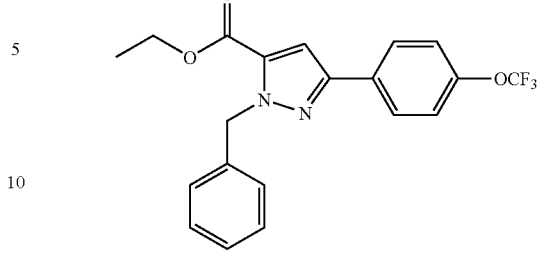

INTERMEDIATE 61

Ethyl-1-benzyl-3-(4-trifluoromethoxyphenyl)pyrazole-5-carboxylate

The same method was employed as in the preparation of intermediate 56 but starting from intermediate 55 (1 g, 3.33 mmol). The title compound was obtained as an oil (1.2 g, 92.31%).

$^1$H NMR (300 MHz, CDCl$_3$): δ 7.85 (d, 2H), 7.25 (m, 7H), 7.1 (s, 1H), 5.75 (s, 2H), 4.25 (q, 2H), 1.25 (t, 3H).

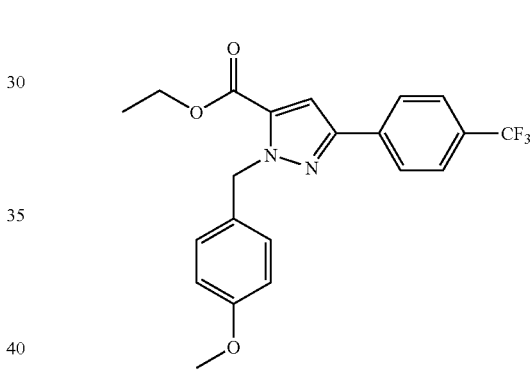

INTERMEDIATE 62

Ethyl-1-(4-methoxybenzyl)-3-(4-trifluoromethylphenyl)pyrazole-5-carboxylate

The same method was employed as in the preparation of intermediate 56 starting from intermediate 54. The title compound was obtained as an oil

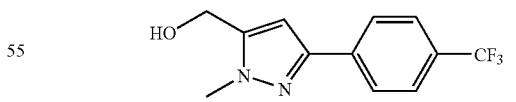

INTERMEDIATE 63

1-methyl-3-(4-trifluoromethylphenyl)-5-hydroxymethyl-pyrazole

To a solution of intermediate 56 (1 g, 3.35 mmol) in anhydrous THF (60 mL) was added dropwise a solution of LiAlH$_4$ 1M in THF (3.36 mL, 1 equiv.) and the mixture was stirred at room temperature during 30 minutes. Water (50 mL) was slowly added and the insoluble material was filtered off on a celite pad. The filtrate was extracted with CH$_2$Cl$_2$, the organic layer was dried over Na$_2$SO$_4$ and concentrated to dryness. The titled compound was obtained as an ecru solid (0.81 g, 94.29%)

Mp: 161° C.

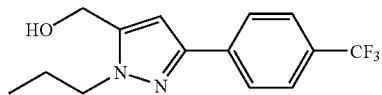

INTERMEDIATE 64

1-propyl-3-(4-trifluoromethylphenyl)-5-hydroxymethyl-pyrazole

The same method was employed as in the preparation of intermediate 63 but starting from intermediate 57. The title compound was obtained as an oil

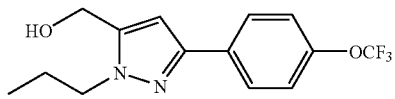

INTERMEDIATE 65

1-(propen-2-yl)-3-(4-trifluoromethoxyphenyl)-5-hydroxymethyl-pyrazole

The same method was employed as in the preparation of intermediate 63 starting from intermediate 58 (1 g, 2.94 mmol). The title compound was obtained as a pale yellow solid (0.85 g, 97%).

Mp: 92° C.

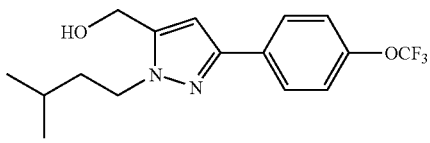

INTERMEDIATE 66

1-(3-methyl-butyl)-3-(4-trifluoromethoxyphenyl)-5-hydroxymethyl-pyrazole

The same method was employed as in the preparation of intermediate 63 starting from intermediate 59 (1.5 g, 4.05 mmol). The title compound was obtained as a yellow solid (1.3 g, 97.76%).

Mp: 75° C.

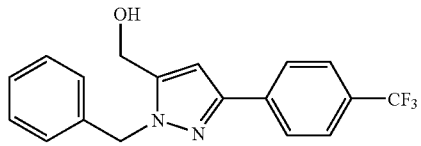

INTERMEDIATE 67

1-benzyl-3-(4-trifluoromethylphenyl)-5-hydroxymethyl-pyrazole

The same method was employed as in the preparation of intermediate 63 starting from intermediate 6. The title compound was obtained as a solid

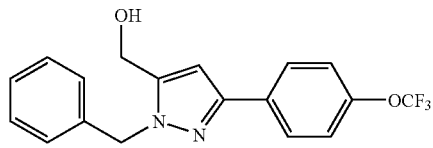

INTERMEDIATE 68

1-benzyl-3-(4-trifluoromethoxyphenyl)-5-hydroxymethyl-pyrazole

The same method was employed as in the preparation of intermediate 63 starting from intermediate 61 (1.2 g, 3.08 mmol). The title compound was obtained as white solid (1.05 g, 98%).

Mp: 118° C.

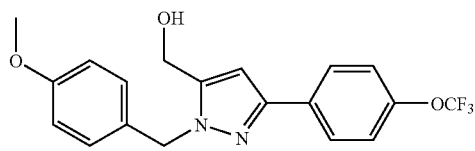

INTERMEDIATE 69

1-(4-methoxybenzyl)-3-(4-trifluoromethylphenyl)-5-hydroxymethyl-pyrazole

The same method was employed as in the preparation of intermediate 63 starting from intermediate 62. The title compound was obtained as a solid

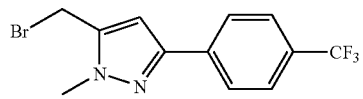

INTERMEDIATE 70

1-methyl-3-(4-trifluoromethylphenyl)-5-bromomethyl-pyrazole

To a solution of intermediate 63 (0.56 g, 2.19 mmol) in CH$_2$Cl$_2$ (20 mL) was added dropwise phosphorus tribromide (0.068 mL, 0.33 equiv.) and the mixture was stirred at room temperature during 1 hour and then poured into a saturated solution of Na$_2$CO$_3$. After extraction with CH$_2$Cl$_2$, the organic layer was dried over Na$_2$SO$_4$ and then concentrated to dryness to afford the titled compound as a colorless oil which crystallised (0.65 g, 93.15%).

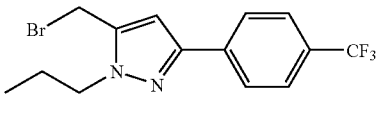

INTERMEDIATE 71

1-propyl-3-(4-trifluoromethylphenyl)-5-bromomethyl-pyrazole

The same method was employed as in the preparation of intermediate 70 starting from intermediate 64. The title compound was obtained as a solid.

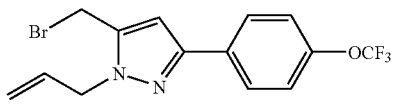

INTERMEDIATE 72

1-(propen-2-yl)-3-(4-trifluoromethoxyphenyl)-5-bromomethyl-pyrazole

The same method was employed as in the preparation of intermediate 70 starting from intermediate 65 (0.85 g, 2.85 mmol). The title compound was obtained as an oil (0.84 g, 81.58%).

$^1$H NMR (300 MHz, CDCl$_3$): δ 7.85 (d, 2H), 7.25 (d, 2H), 6.65 (s, 1H), 6.1 (m, 1H), 5.25 (m, 2H), 4.95 (d, 2H), 4.55 (s, 2H).

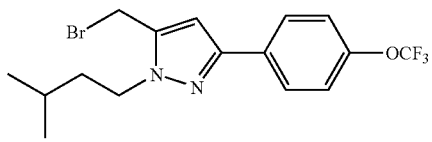

INTERMEDIATE 73

1-(3-methyl-butyl)-3-(4-trifluoromethoxyphenyl)-5-bromomethyl-pyrazole

The same method was employed as in the preparation of intermediate 70 starting from intermediate 66 (1.3 g, 3.96 mmol). The title compound was obtained as an orange oil (1.34 g, 86.47%).

$^1$H NMR (300 MHz, CDCl$_3$): δ 7.8 (d, 2H), 7.2 (d, 2H), 6.45 (s, 1H), 4.5 (s, 2H), 4.2 (t, 2H), 1.8 (m, 3H), 1 (d, 6H).

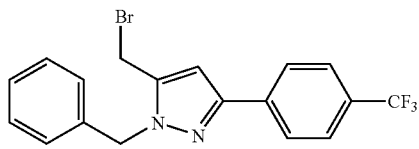

INTERMEDIATE 74

1-benzyl-3-(4-trifluoromethylphenyl)-5-bromomethyl-pyrazole

The same method was employed as in the preparation of intermediate 70 starting from intermediate 67. The title compound was obtained as a solid

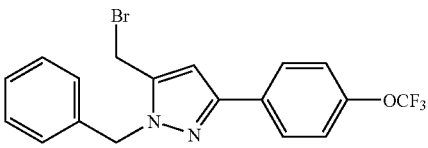

INTERMEDIATE 75

1-benzyl-3-(4-trifluoromethoxyphenyl)-5-bromomethyl-pyrazole

The same method was employed as in the preparation of intermediate 70 starting from intermediate 68 (1 g, 2.87 mmol). The title compound was obtained as an oil which crystallised (1.08 g, 91.45%).

$^1$H NMR (300 MHz, CDCl$_3$): δ 7.85 (d, 2H), 7.25 (m, 7H), 6.65 (s, 1H), 5.55 (s, 2H), 4.35 (s, 2H).

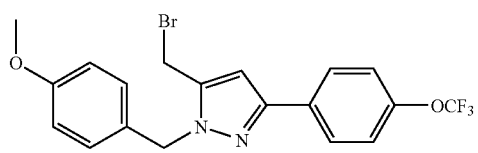

INTERMEDIATE 76

1-(4methoxybenzyl)-3-(4-trifluoromethylphenyl)-5-bromomethyl-pyrazole

The same method was employed as in the preparation of intermediate 70 starting from intermediate 69. The title compound was obtained as a solid

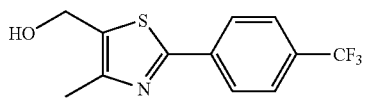

INTERMEDIATE 77

To a well stirred solution of LiAlH$_4$ (1.52 g, 40 mmol) in dry THF (50 mL) at 0° C., was slowly added a solution of ethyl 4-methyl-2-[4-(trifluoromethyl)phenyl]-thiazole-5-carboxylate (12.6 g, 40 mmol) in dry THF (50 mL). The mixture was stirred at room temperature for 2 hs. The reaction was quenched by slow addition at 0° C. of water (2 mL), 5N NaOH (2 mL) and water (6 mL). The precipitate was filtered, washed with EtOAc, MeOH, CH$_2$Cl$_2$ and THF. After evaporation, a yellow solid was obtained, that was crystallyzed from MeOH-water to afford the title compound (9.90 g, 36 mmol, 90%) as a yellow solid mp 120–122° C.

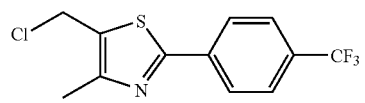

INTERMEDIATE 78

To a cold (0° C.) stirred solution of intermediate 1 (8.2 g, 30 mmol) and Et$_3$N (6.07 g, 8.36 mL, 60 mmol), in dry CH$_2$Cl$_2$ (120 mL) was slowly added MeSO$_2$Cl (5.49 g, 3.71 mL, 48 mmol). After 2 hs at 0° C. more Et$_3$N (6 mmol) and MeSO$_2$Cl (4.8 mmol) were added. After 2 h more, a tlc (hexane/EtOAc, 1:1) showed complete reaction. The reaction mixture was diluted with CH$_2$Cl$_2$ (120 mL) and washed with NaHCO$_3$ (sat.) (2×240 mL) and water (2×240 mL), dried, filtered and evaporated to afford the title compound (8.0 g, 27 mmol, 90%) as a yellow solid.

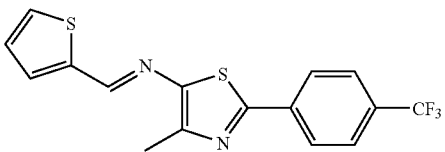

INTERMEDIATE 79

[4-methyl-2-(4-trifluoromethylphenyl)thiazol-5-yl] thiophen-2-ylmethylene amine

A solution of intermediate 7 (1.5 g, 5.8 mmol) and thiophen-2-ylcarboxaldehyde (0.54 mL, 1 eq.) in EtOH (10 mL) was stirred to reflux overnight. After cooling, the reaction was evaporated to dryness and the residue chromatographed with CH$_2$Cl$_2$ to give the title compound as a white solid (1.73 g, 84.5%).

[APCI MS] m/z: 353 (MH+)

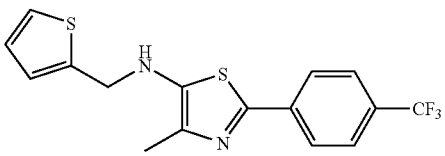

INTERMEDIATE 80

[4-methyl-2-(4-trifluoromethylphenyl)thiazol-5-yl] thiophen-2-ylmethyl amine

To a solution of intermediate 79 (1.73 g, 4.9 mmol) in ethanol (20 mL) was added sodium borohydride (204 mg, 1.1 eq.) and the reaction was stirred to reflux for 30 min. After cooling, the reaction was evaporated to dryness, then hydrolyzed with ammonium chloride and extracted with CH$_2$Cl$_2$. The organic phase was washed with water, dried over Na$_2$SO$_4$, filtered and the solvent evaporated off to afford the title compound which was not further purified (1.74 g, quantitative).

$^1$H NMR (300 MHz, CDCl$_3$) δ: 7.85 (d, 2H), 7.55 (d, 2H), 7.20 (m, 1H), 6.95 (m, 1H), 6.92 (m, 1H), 4.45 (s, 2H), 2.25 (s, 3H).

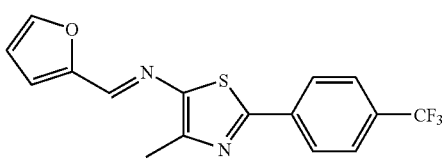

INTERMEDIATE 81

[4-methyl-2-(4-trifluoromethylphenyl)thiazol-5-yl] furan-2-ylmethylene amine

A solution of intermediate 7 (1 g, 3.87 mmol) and furan-2-ylcarboxaldehyde (0.35 mL, 1.1 eq.) in CH$_2$Cl$_2$ (10 mL) was added the NaBH(OAc)$_3$ (1.23 g, 1.5 eq.) and the reaction stirred overnight at room temperature. After cooling, the reaction was hydrolyzed with water, extracted with CH$_2$Cl$_2$, dried over Na$_2$SO$_4$, filtered and the solvent removed in vacuo. The residue was then chromatographed eluting with CH$_2$Cl$_2$ to afford the title compound as a yellow solid (820 mg, 63%).

[APCI MS] m/z: 337 (MH+)

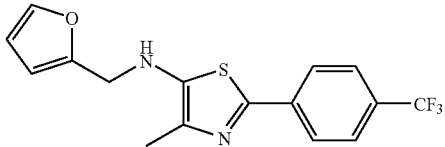

INTERMEDIATE 82

[4-methyl-2-(4-trifluoromethylphenyl)thiazol-5-yl]furan-2-ylmethyl amine

To a solution of intermediate 81 (820 mg, 2.44 mmol) in ethanol (20 mL) was added sodium borohydride (184 mg, 2 eq.) and the reaction was stirred to reflux for 20 min. After cooling, the reaction was hydrolyzed with ammonium chloride and then evaporated to dryness. The residue was taken up in EtOAc, washed with water, dried over Na$_2$SO$_4$, filtered and the solvent in vacuo. The residue was chromatographed eluting with cyclohexane/EtOAc (80/20) to afford the title compound as an orange oil (540 mg, 65%).

$^1$H NMR (300 MHz, CDCl$_3$) δ: 7.80 (d, 2H), 7.50 (d, 2H), 7.30 (m, 1H), 6.25 (m, 1H), 6.20 (m, 1H), 4.25 (s, 2H), 2.25 (s, 3H).

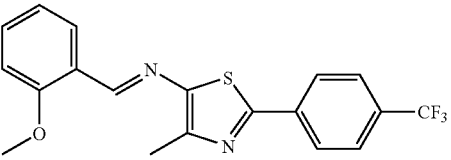

INTERMEDIATE 83

(2-Methoxybenzylidene)-[4-methyl-2-(4-trifluoromethylphenyl)thiazol-5-yl]amine

A solution of intermediate 7 (990 mg, 3.49 mmol) and 2-methoxybenzaldehyde (475 mg, 1 eq.) in EtOH (10 mL) stirred overnight at room temperature. After cooling, the reaction was evaporated to dryness and the residue was then chromatographed eluting with petroleum ether/EtOAc (95/5) to afford the title compound as a yellow solid (780 mg, 59.4%).

$^1$H NMR (300 MHz, CDCl$_3$) δ: 8.90 (s, 1H), 8.35 (d, 1H), 8.20 (d, 2H), 7.85 (d, 2H), 7.60 (m, 1H), 7.20 (t, 1H), 7.1 (d, 1H), 4.10 (s, 3H), 2.80 (s, 3H).

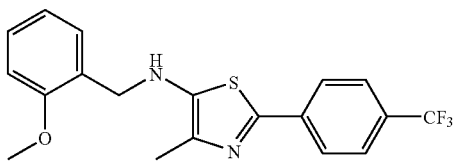

INTERMEDIATE 84

(2-Methoxybenzyl)-[4-methyl-2-(4-trifluoromethylphenyl)thiazol-5-yl]amine

To a solution of intermediate 83 (780 mg, 2.14 mmol) in EtOH (20 mL) was added sodium borohydride (86 mg, 1.1 eq.) and the reaction was stirred at reflux for 2 h. After cooling, the reaction was evaporated to dryness, the residue taken up in 1N HCl and extracted with $CH_2Cl_2$. The organic phase was washed with water, dried over $Na_2SO_4$, filtered and the solvent in vacuo to afford the title compound which was used directly without further purification (784 mg, quantitative).
$^1$H NMR (300 MHz, $CDCl_3$) δ: 7.85 (d, 2H), 7.55 (d, 2H), 7.25 (m, 2H), 6.25 (m, 1H), 6.85 (m, 2H), 4.25 (s, 2H), 3.82 (s, 3H), 2.20 (s, 3H).

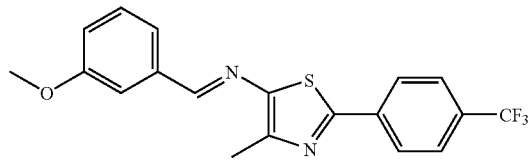

INTERMEDIATE 85

(3-Methoxybenzylidene)-[4-methyl-2-(4-trifluoromethylphenyl)thiazol-yl]amine

A solution of intermediate 7 (990 mg, 3.49 mmol) and 3-methoxybenzaldehyde (475 mg, 1 eq.) in EtOH (10 mL) stirred overnight at reflux. After cooling, the reaction was evaporated to dryness and the residue was then chromatographed eluting with $CH_2Cl_2$/cyclohexane (70/305) to afford the title compound as a yellow solid (1.07 g, 81%).
$^1$H NMR (300 MHz, $CDCl_3$) δ: 8.55 (s, 1H), 8.30 (d, 1H), 7.95 (d, 2H), 7.70 (m, 1H), 7.65 (m, 2H), 7.25 (m, 1H), 4.15 (s, 3H), 2.90 (s, 3H).

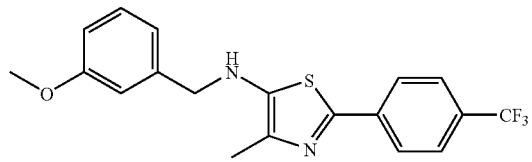

INTERMEDIATE 86

(3-Methoxybenzyl)-[4-methyl-2-(4-trifluoromethylphenyl)thiazol-5-yl]amine

To a solution of intermediate 85 (1.07 g, 2.84 mmol) in EtOH (20 mL) was added sodium borohydride (130 mg, 1.2 eq.) and the reaction was stirred at reflux for 1 h. After cooling, the reaction was evaporated to dryness, the residue taken up in 1N HCl, neutralized with 1N NaOH and extracted with $CH_2Cl_2$. The organic phase was washed with water, dried over $Na_2SO_4$, filtered and the solvent in vacuo to afford the title compound which was used directly without further purification (1.08 g, quantitative).
$^1$H NMR (300 MHz, $CDCl_3$) δ: 7.75 (d, 2H), 7.45 (d, 2H), 7.15 (t, 1H), 6.85 (d, 1H), 6.80 (dd, 1H), 6.70 (dd, 1H), 4.15 (s, 2H), 3.65 (s, 3H), 2.20 (s, 3H).

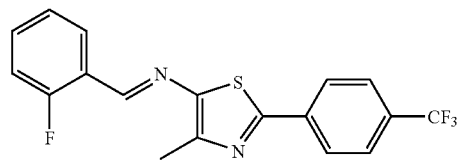

INTERMEDIATE 87

(2-Fluorobenzylidene)-[4-methyl-2-(4-trifluoromethylphenyl)thiazol-5-yl]amine

A solution of intermediate 7 (1 g, 3.5 mmol) and 2-fluorobenzaldehyde (0.42 mL, 1 eq.) in EtOH (10 mL) stirred at 70° C. for 4 h. The reaction was then cooled to room temperature and allowed to sit for 18 h upon which a solid precipitated. The solid was recovered, washed with EtOH and dried under vacuum to afford the title compound as a yellow solid (1 g, 78%).
$^1$H NMR (300 MHz, $CDCl_3$) δ: 8.80 (s, 1H), 8.35 (m, 1H), 8.25 (d, 2H), 7.85 (d, 2H), 7.60 (m, 1H), 7.45 (m, 1H), 7.30 (t, 1H), 2.85 (s, 3H).

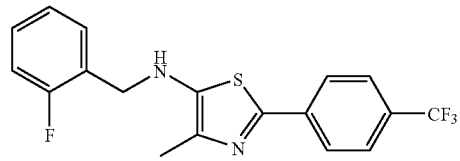

INTERMEDIATE 88

(2-Fluorobenzyl)-[4-methyl-2-(4-trifluoromethylphenyl)thiazol-5-yl]amine

To a solution of intermediate 87 (1 g, 2.74 mmol) in THF/EtOH (20 mL) was added sodium borohydride (150 mg, 1.5 eq.) and the reaction was stirred at room temperature for 20 min. After cooling, the reaction was evaporated to dryness, the residue taken up in 1N HCl, neutralized with 1N NaOH and extracted with $CH_2Cl_2$. The organic phase was dried over $Na_2SO_4$, filtered and the solvent in vacuo to afford the title compound which was used directly without further purification (1 g, quantitative).
$^1$H NMR (300 MHz, $CDCl_3$) δ: 7.70 (d, 2H), 7.45 (d, 2H), 7.25–7.10 (m, 2H), 6.95 (m, 2H), 4.20 (bs, 2H), 3.80 (bs, 1H), 2.15 (s, 3H).

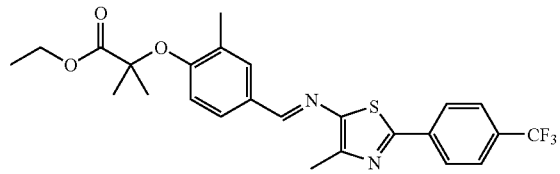

INTERMEDIATE 89

2-Methyl-2-(2-methyl-4-{([4-methyl-2-(4-trifluoromethylphenyl)thiazol-5-yl]imino)methyl}phenoxy)propionic acid ethyl ester A solution of intermediate 7 (2 g, 7.74 mmol) and intermediate 25 (1.94 g, 1 eq.) in EtOH (10 mL) stirred at 85° C. for 48 h. The reaction was cooled, evaporated to dryness and the residue chromatographed eluting with CH₂Cl₂ to afford the title compound as a solid (3.32 g, 87.5%).

[APCI MS] m/z: 491 (MH+)

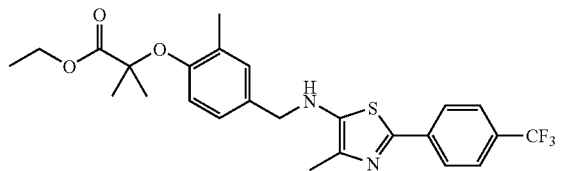

INTERMEDIATE 90

2-Methyl-2-(2-methyl-4-{([4-methyl-2-(4-trifluoromethylphenyl)thiazol-5-yl]amino)methyl}phenoxy)propionic acid ethyl ester The same method was employed as in the preparation of intermediate 88 starting from intermediate 89 (1 g, 2.04 mmol). The title compound was obtained as an oil (1 g, quantitative).

$^1$H NMR (300 MHz, CDCl₃) δ: 7.70 (d, 2H), 7.40 (d, 2H), 7.00 (bs, 1H), 6.90 (dd, 1H), 6.50 (d, 1H), 4.10 (q, 2H), 4.00 (s, 2H), 2.15 (s, 3H), 2.05 (s, 3H), 1.40 (s, 6H), 1.05 (t, 3H).

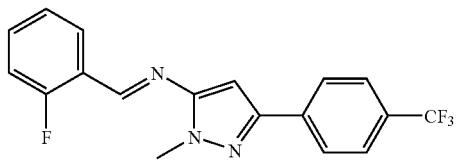

INTERMEDIATE 91

(2-Fluorobenzylidene)-[2-methyl-5-(4-trifluoromethylphenyl)-2H-pyrazol-3-yl]amine A solution of intermediate 18 (800 mg, 3.3 mmol) and 2-fluorobenzaldehyde (0.35 mL, 1 eq.) in EtOH (10 mL) stirred at 50° C. overnight. As the reaction cooled to room temperature a precipitate formed. The precipitate was recovered, washed with EtOH and dried under vacuum to afford the title compound as a white solid (870 mg, 82%).

$^1$H NMR (300 MHz, CDCl₃) δ: 9.10 (s, 1H), 8.35 (m, 1H), 8.05 (d, 2H), 7.80 (d, 2H), 7.65 (m, 1H), 7.40 (m, 1H), 7.25 (t, 1H), 6.75 (s, 1H), 4.15 (s, 3H).

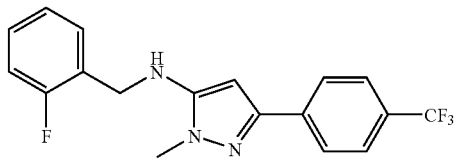

INTERMEDIATE 92

(2-Fluorobenzyl)-[2-methyl-5-(4-trifluoromethylphenyl)-2H-pyrazol-3-yl]amine

To a solution of intermediate 91 (870 mg, 2.7 mmol) in THF/EtOH (20 mL) was added sodium borohydride (excess) and the reaction stirred at room temperature for 1 h. The reaction was then heated to 50° C. for another 2 h. The reaction was cooled, evaporated to dryness, the residue taken up with water, acidified with 1N HCl and then neutalized with 1N NaOH. The mixture was then extracted with CH₂Cl₂. The organic layer was dried over Na₂SO₄, filtered and the solvent removed under vacuum to afford the title compound as a clear oil (850 mg, 95%).

$^1$H NMR (300 MHz, CDCl₃) δ: 7.80 (m, 1H), 7.60 (d, 2H), 7.35 (m, 1H), 7.25 (m, 1H), 7.15–7.00 (m, 2H), 5.80 (s, 1H), 4.35 (s, 2H), 3.70 (s, 3H).

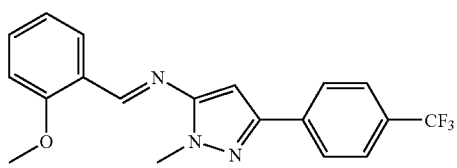

INTERMEDIATE 93

(2-Methoxybenzylidene)-[2-methyl-5-(4-trifluoromethylphenyl)2H-pyrazol-3-yl]amine A solution of intermediate 18 (800 mg, 3.3 mmol) and 2-methoxybenzaldehyde (450 mg, 1 eq.) in EtOH (10 mL) stirred at 50° C. overnight. As the reaction cooled to room temperature a precipitate formed. The precipitate was recovered, washed with EtOH and dried under vacuum to afford the title compound as a solid (1.19 g, quantitative). $^1$H NMR (300 MHz, CDCl₃) δ: 9.10 (s, 1H), 8.20 (d, 1H), 7.90 (d, 2H), 7.60 (d, 2H), 7.45 (t, 1H), 7.05 (t, 1H), 6.95 (d, 1H), 6.55 (s,1H), 4.00 (s, 3H), 3.90 (s, 3H).

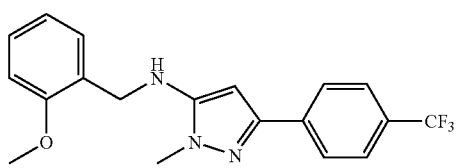

INTERMEDIATE 94

(2-Methoxybenzyl)-[2-methyl-5-(4-trifluoromethylphenyl)-2H-pyrazol-3-yl]amine

To a solution of intermediate 93 (1.19 g, 3.3 mmol) in THF/EtOH (20 mL) was added sodium borohydride (excess) and the reaction stirred at room temperature for 1 h. The reaction was then heated to 50° C. for another 2h. The reation was cooled, evaporated to dryness, the residue taken up with water, acidified with 1N HCl and then neutalized with 1N NaOH. The mixture was then extracted with CH₂Cl₂. The organic layer was dried over Na₂SO₄, filtered and the solvent removed under vacuum to afford the title compound as a clear oil (800 mg, 75%).

¹H NMR (300 MHz, CDCl₃) δ: 7.75 (d, 2H), 7.52 (d, 2H), 7.22 (m, 2H), 6.86 (m, 2H), 5.79 (s, 1H), 4.23 (bs, 1H), 3.80 (s, 3H), 3.60 (s, 3H).

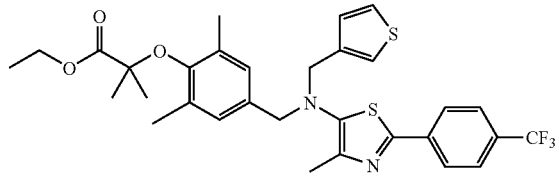

EXAMPLE 1

2-[2,6-Dimethyl-4-({[4-methyl-2-(4-trifluoromethyl-phenyl)-thiazol-5-yl]-thiophen-3-ylmethyl-amino}-methyl)-phenoxy]-2-methyl-propionic acid ethyl ester To a solution of intermediate 3 (1.84 g, 2 eq) in 3-Methyl-2-butanone (50 mL) was added at rt cesium carbonate (1.82 g, 2 eq.) and intermediate 9 (1 g, 2.8 mmol). The reaction mixture was stirred at 90° C. overnight; After evaporation, the residue was diluted in ethyl acetate (300 mL), washed with water (3*150 mL), drying over Na₂SO₄, filtered and evaporated off. The residue was purified by flash chromatography (DCM) to give the title compound (350 mg, 0.58 mmol) as a yellow oil in a 20% yield.

¹H NMR (300 MHz, CDCl₃) δ: 7.92 (d, 2H), 7.61 (d, 2H), 7.24 (m, 1H), 7.04 (d, 1H), 6.97 (d, 1H), 6.87 (s, 2H), 4.26 (q, 2H), 4.04 (s, 2H), 3.93 (s, 2H), 2.21 (s, 3H), 2.16 (s, 6H), 1.44 (s, 6H), 1.33 (t, 3H).

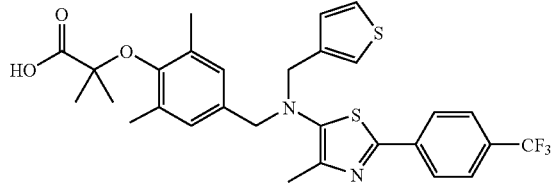

EXAMPLE 2

2-[2,6-Dimethyl-4-({[4-methyl-2-(4-trifluoromethyl-phenyl)-thiazol-5-yl]-thiophen-3-ylmethyl-amino}-methyl)-phenoxy]-2-methyl-propionic acid To a solution of example 1 (300 mg, 0.5 mmol) in EtOH was added a 1N NaOH solution and the mixture was stirred to reflux for 1 hour and then the solvent was evaporated off. The residue was acidified with a 1N HCl solution and the precipitate was purified by flash chromatography using DCW/MeOH (90/10), to give the title compound (75 mg, 0.13 mmol) as crystals.

MP: 90–100° C. [APCI MS] m/z: 575 (MH+) ¹H NMR (300 MHz, CDCl₃) δ: 7.90 (d, 2H), 7.60 (d, 2H), 7.24 (m, 1H), 7.05 (s, 1H), 6.99 (d, 1H), 6.89 (s, 2H), 4.04 (s, 2H), 3.93 (s, 2H), 2.22 (s, 3H), 2.16 (s, 6H), 1.39 (s, 6H).

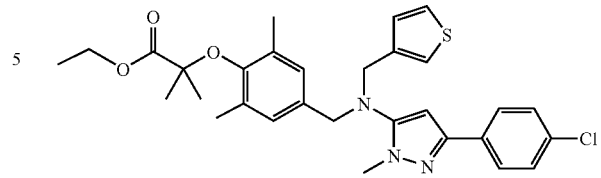

EXAMPLE 3

2-[4-({[5-(4-Chloro-phenyl)-2-methyl-2H-pyrazol-3-yl]-thiophen-3-ylmethyl-amino}-methyl)-2,6-dimethyl-phenoxy]-2-methyl-propionic acid ethyl ester The same method was employed as in the preparation of example 1 but starting from intermediate 12 (1 g, 3.4 mmol) and intermediate 3 (2.24 g, 2 eq) and gave the title compound as a colourless oil (420 mg, 0.76 mmol) in a 11% yield after purification by flash chromatography using DCM.

¹H NMR (300 MHz, CDCl₃) δ: 7.63 (d, 2H), 7.32 (d, 2H), 7.24 (m, 1H), 7.00 (s, 1H), 6.88 (d, 1H), 6.83 (s, 2H), 6.11 (s, 1H), 4.27 (q, 2H), 4.01 (s, 2H), 3.92 (s, 2H), 3.64 (s, 3H), 2.16 (s, 6H), 1.44 (s, 6H), 1.33 (t, 3H).

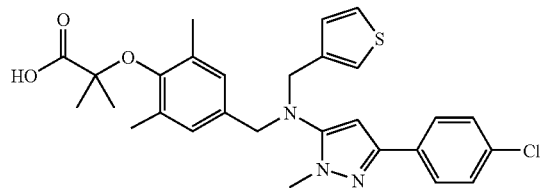

EXAMPLE 4

2-[4-({[5-(4-Chloro-phenyl)-2-methyl-2H-pyrazol-3-yl]-thiophen-3-ylmethyl-amino}-methyl)-2.6-dimethyl-phenoxy]-2-methyl-propionic acid The same method was employed as in the preparation of example 2 but starting from example 3 (400 mg, 0.74 mmol) to give the title compound as a white powder (260 mg, 0.50 mmol) in a 67% yield after purification by flash chromatography using DCM/MeOH (90/10).

[APCI MS] m/z: 524 (MH+) ¹H NMR (300 MHz, CDCl₃) δ: 7.63 (d, 2H), 7.32 (d, 2H), 7.25 (m, 1H), 7.02 (s, 1H), 6.89 (m, 3H), 6.12 (s, 1H), 4.03 (s, 2H), 3.94 (s, 2H), 3.66 (s, 3H), 2.20 (s, 6H), 1.49 (s, 6H).

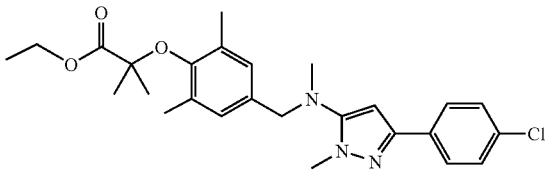

EXAMPLE 5

2-[4-({[5-(4-Chloro-phenyl)-2-methyl-2H-pyrazol-3-yl]-methyl-amino}-methyl)-2,6-dimethyl-phenoxy]-2-methyl-propionic acid ethyl ester The same method was employed as in the preparation of example 1 but starting from intermediate 13 (1 g, 4.5 mmol) and intermediate 3 (3 g, 1.5 eq) and gave the title compound as a yellow oil (750 mg, 1.6 mmol) in a 36% yield after purification by flash chromatography.

¹H NMR (300 MHz, CDCl₃) δ: 7.88 (d, 2H), 7.52 (d, 2H), 7.05 (s, 2H), 6.20 (s, 1H), 4.37 (q, 2H), 4.01 (s, 2H), 3.95 (s, 3H), 2.79 (s, 3H), 2.16 (s, 6H), 1.65 (s, 6H), 1.45 (t, 3H). non enregistrée

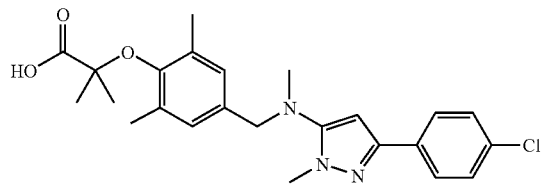

EXAMPLE 6

2-[4-({[5-(4-Chloro-phenyl)-2-methyl-2H-pyrazol-3-yl]-methyl-amino}-methyl)-2,6-dimethyl-phenoxy]-2-methyl-propionic acid The same method was employed as in the preparation of example 2 but starting from example 5 (750 mg, 1.6 mmol) to give the title compound as a white powder (370 mg, 0.80 mmol) in a 52% yield after crystallisation in CH₃CN.

MP: 158° C. [APCI MS] m/z: 442 (MH+) ¹H NMR (300 MHz, DMSO) δ: 7.57 (d, 2H), 7.23 (d, 2H), 6.80 (s, 2H), 6.20 (s, 2H), 3.72 (s, 2H), 3.55 (s, 2H), 2.37 (s, 3H), 1.98 (s, 6H), 1.16 (s, 6H).

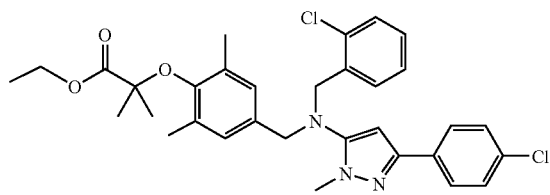

EXAMPLE 7

2-[4-({(2-Chloro-benzyl)-[5-(4-chloro-phenyl)-2-methyl-2H-pyrazol-3-yl]-amino}-methyl)-2,6-dimethyl-phenoxy]-2-methyl-propionic acid ethyl ester The same method was employed as in the preparation of example 1 but starting from intermediate 15 (1 g, 3 mmol) and intermediate 3 (2 g, 2 eq) and gave the title compound (1.1 g, 1.9 mmol) in a 63% yield after purification by flash chromatography using DCM.

[APCI MS] m/z: 581 (MH+) ¹H NMR (300 MHz, CDCl₃) δ: 7.63 (d, 2H), 7.33 (m, 3H), 7.15 (m, 2H), 6.83 (s, 2H), 6.21 (s, 1H), 4.26 (q, 2H), 4.14 (s, 2H), 3.98 (s, 3H), 3.53 (s, 3H), 2.14 (s, 6H), 1.43 (s, 6H), 1.33 (t, 3H).

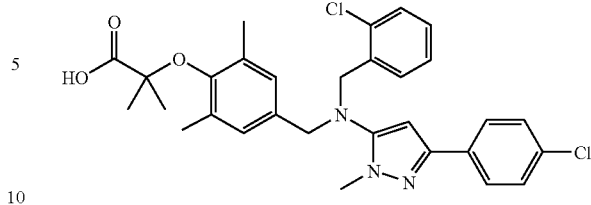

EXAMPLE 8

2-[4-({(2-Chloro-benzyl)-[5-(4-chloro-phenyl)-2-methyl-2H-pyrazol-3-yl]-amino}-methyl)-2,6-dimethyl-phenoxy]-2-methyl-propionic acid The same method was employed as in the preparation of example 2 but starting from example 7 (1 g, 1.72 mmol) to give the title compound as a yellow foam (180 mg, 0.33 mmol) in a 20% yield after purification by flash chromatography.

[APCI MS] m/z: 552 (MH+) ¹H NMR (300 MHz, CDCl₃) δ: 7.63 (d, 2H), 7.33 (m, 3H), 7.16 (m, 2H), 6.87 (s, 2H), 6.23 (s, 1H), 4.16 (s, 2H), 4.00 (s, 2H), 3.54 (s, 3H), 2.18 (s, 6H), 1.48 (s, 6H).

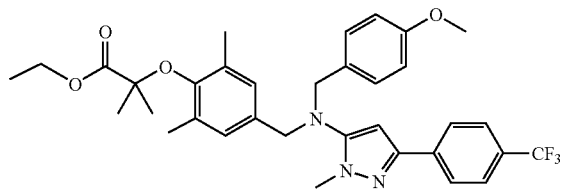

EXAMPLE 9

2-[4-({(4-Methoxy-benzyl)-[2-methyl-5-(4-trifluoromethyl-phenyl)-2H-pyrazol-3-yl]-amino}-methyl)-2,6-dimethyl-phenoxy]-2-methyl-propionic acid ethyl ester The same method was employed as in the preparation of example 1 but starting from intermediate 20 (1 g, 2.7 mmol) and intermediate 3 (1.82 g, 2 eq) and gave the title compound (380 mg, 0.62 mmol) in a 23% yield after purification by flash chromatography using DCM/MeOH (98/02).

¹H NMR (300 MHz, CDCl₃) δ: 7.82 (d, 2H), 7.60 (d, 2H), 7.10 (d, 2H), 6.82 (m, 4H), 6.19 (s, 1H), 4.27 (q, 2H), 3.77 (s, 3H), 3.65 (s, 3H), 2.15 (s, 6H), 1.44 (s, 9H), 1.33 (t, 3H).

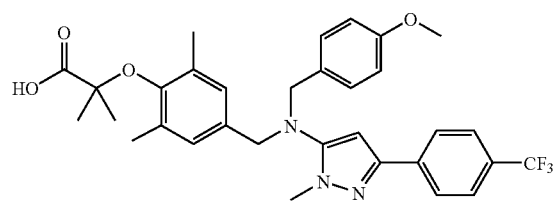

EXAMPLE 10

2-[4-({(4-Methoxy-benzyl)-[2-methyl-5-(4-trifluoromethyl-phenyl)-2H-pyrazol-3-yl]-amino}-methyl)-2,6-dimethyl-phenoxy]-2-methyl-propionic acid The same method was employed as in the preparation of example 2 but starting from example 9 (350 mg, 1.64 mmol) to give the title compound as a white foam (260 mg, 0.45 mmol) in a 27% yield after purification by flash chromatography.

[APCI MS] m/z: 582 (MH+) $^H$ NMR (300 MHz, CDCl$_3$) δ: 7.81 (d, 2H), 7.61 (d, 2H), 7.10 (d, 2H), 6.87 (s, 2H), 6.82 (d, 2H), 6.21 (s, 1H), 3.98 (s, 2H), 3.94 (s, 2H), 3.77 (s, 3H), 3.66 (s, 3H), 2.19 (s, 6H), 1.49 (s, 6H).

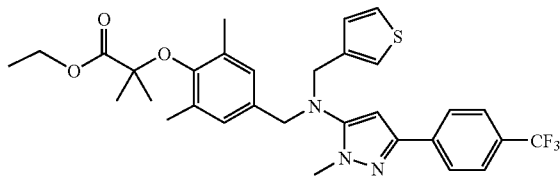

EXAMPLE 11

2-[2,6-Dimethyl-4-({[2-methyl-5-(4-trifluoromethyl-phenyl)-2H-pyrazol-3-yl]-thiophen-3-ylmethyl-amino}-methyl)-phenoxy]-2-methyl-propionic acid ethyl ester The same method was employed as in the preparation of example 1 but starting from intermediate 22 (1 g, 3 mmol) and intermediate 3 (2 g, 2 eq) and gave the title compound (850 mg, 1.45 mmol) in a 48% yield after purification by flash chromatography.

$^1$H NMR (300 MHz, CDCl$_3$) δ: 7.82 (d, 2H), 7.62 (d, 2H), 7.23 (m, 1H), 7.01 (d, 1H), 6.90 (d, 1H), 6.83 (s, 2H), 6.18 (s, 1H), 4.28 (q, 2H), 4.04 (s, 2H), 3.95 (s, 2H), 3.69 (s, 3H), 2.19 (s, 6H), 1.44 (s, 6H), 1.33 (t, 3H).

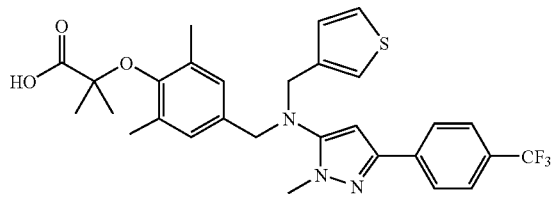

EXAMPLE 12

2-[2,6-Dimethyl-4-({[2-methyl-5-(4-trifluoromethyl-phenyl)-2H-pyrazol-3-yl]-thiophen-3-ylmethyl-amino}-methyl)-phenoxy]-2-methyl-propionic acid The same method was employed as in the preparation of example 2 but starting from example 11 (800 mg, 1.4 mmol) to give the title compound as a ochre powder (528 mg, 0.45 mmol) in a 69% yield.

[APCI MS] m/z: 558 (MH+) $^1$H NMR (300 MHz, CDCl$_3$) δ: 7.80 (d, 2H), 7.61 (d, 2H), 7.10 (d, 2H), 7.25 (m, 1H), 7.01 (d, 1H), 6.88 (d, 1H), 6.87 (s, 2H), 6.20 (s, 1H), 4.05 (s, 2H), 3.95 (s, 2H), 3.67 (s, 3H), 2.20 (s, 6H), 1.49 (s, 6H).

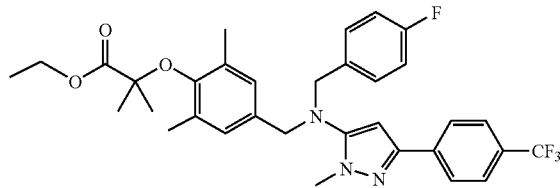

EXAMPLE 13

2-[4-({(4-Fluoro-benzyl)-[2-methyl-5-(4-trifluoromethyl-phenyl)-2H-pyrazol-3-yl]-amino}-methyl)-2,6-dimethyl-phenoxy]-2-methyl-propionic acid ethyl ester The same method was employed as in the preparation of example 1 but starting from intermediate 24 (1 g, 2.86 mmol) and intermediate 3 (1.88 g, 2 eq) and gave the title compound.

$^1$H NMR (300 MHz, CDCl$_3$) δ: 7.79 (d, 2H), 7.58 (d, 2H), 7.14 (m, 2H), 6.96 (m, 2H), 6.81 (s, 2H), 6.19 (s, 1H), 4.28 (q, 2H), 3.98 (s, 2H), 3.91 (s, 2H), 3.63 (s, 3H), 2.16 (s, 6H), 1.44 (s, 6H), 1.33 (t, 3H).

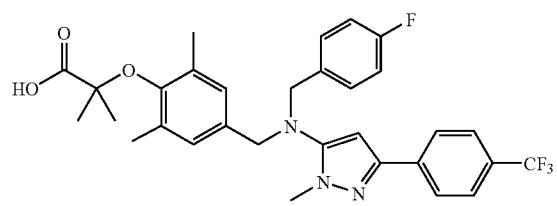

EXAMPLE 14

2-[4-({(4-Fluoro-benzyl)-[2-methyl-5-(4-trifluoromethyl-phenyl)-2H-pyrazol-3-yl]-amino}-methyl)-2,6-dimethyl-phenoxy]-2-methyl-propionic acid The same method was employed as in the preparation of example 2 but starting from example 13 to give the title compound as a white powder (400 mg, 0.7 mmol) in a 24% yield.

MP>90° C. [APCI MS] m/z: 570 (MH+) $^1$H NMR (300 MHz, DMSO) δ: 7.79 (d, 2H), 7.61 (d, 2H), 7.24 (m, 2H), 7.00 (m, 2H), 6.85 (s, 2H), 6.48 (s, 1H), 3.95 (s, 2H), 3.87 (s, 2H), 3.57 (s, 3H), 2.02 (s, 6H), 1.21 (s, 6H).

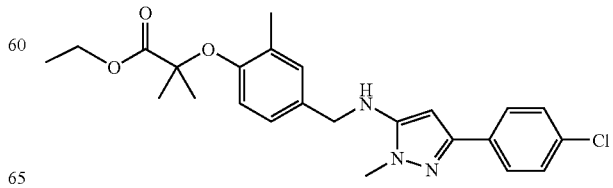

EXAMPLE 15

2-(4-{[5-(4-Chloro-phenyl)-2-methyl-2H-pyrazol-3-yl-amino]-methyl}-2-methyl-phenoxy)-2-methyl-propionic acid ethyl ester The same method was employed as in the preparation of intermediate 9 but starting from intermediate 26 (2.4 g, 5.5 mmol), to give the title compound as oil (1.85 g, 4.2 mmol) in a 76% yield.

$^1$H NMR (300 MHz, CDCl$_3$) δ: 7.65 (d, 2H), 7.32 (d, 2H), 7.02 (s, 1H), 6.85 (d, 1H), 6.58 (d, 1H), 6.16 (s, 1H), 4.63 (s, 2H), 4.21 (q, 4H), 3.36 (s, 3H), 2.18 (s, 3H), 1.56 (s, 6H), 1.22 (t, 3H).

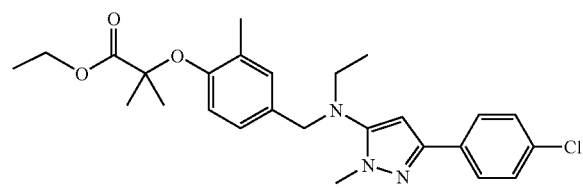

EXAMPLE 16

2-[4-({[5-(4-Chloro-phenyl)-2-methyl-2H-pyrazol-3-yl]-ethyl-amino}-methyl)-2-methyl-phenoxy]-2-methyl-propionic acid ethyl ester A solution of example 15 (1.8 g, 4 mmol) in MIK (50 mL) was treated with Cs$_2$CO$_3$ (5 g, excess) and Ethyl iodide (2 mL). The resulting mixture was stirred at 95° C. overnight under pressure. After cooling to rt the reaction mixture was filtered off and the filtrate was evaporated off. The residue was diluted with DCM, washed with water and drying over Na$_2$SO$_4$ and filtration evaporation to give the title compound (320 mg, 0.68 mmol) as oil in a 17% yield after purification by flash chromatography.

$^1$H NMR (300 MHz, CDCl$_3$) δ: 7.63 (d, 2H), 7.32 (d, 2H), 7.02 (s, 1H), 6.85 (d, 1H), 6.59 (d, 1H), 6.16 (s, 1H), 4.63 (s, 2H), 4.21 (q, 4H), 3.36 (s, 3H), 2.18 (s, 3H), 1.56 (s, 6H), 1.22 (t, 6H).

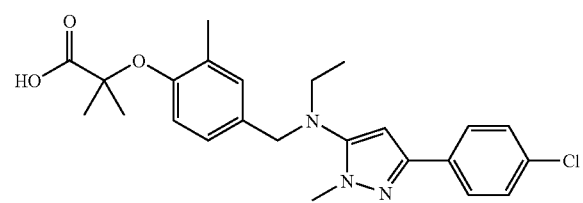

EXAMPLE 17

2-[4-({[5-(4-Chloro-phenyl)-2-methyl-2H-pyrazol-3-yl]-ethyl-amino}-methyl)-2-methyl-phenoxy]-2-methyl-propionic acid The same method was employed as in the preparation of example 2 but starting from example 16 to give the title compound as white crystals (130 mg, 0.29 mmol) in a 43% yield after purification by flash chromatography.

MP: 208° C. $^1$H NMR (300 MHz, DMSO) δ: 13.04 (s, 1H), 7.77 (d, 2H), 7.50 (d, 2H), 7.10 (s, 1H), 6.99 (d, 1H), 6.73 (s, 1H), 6.62 (s, 1H), 4.70 (s, 2H), 4.22 (m, 2H), 3.45 (s, 3H), 2.18 (s, 3H), 1.54 (s, 6H), 1.08 (m, 3H).

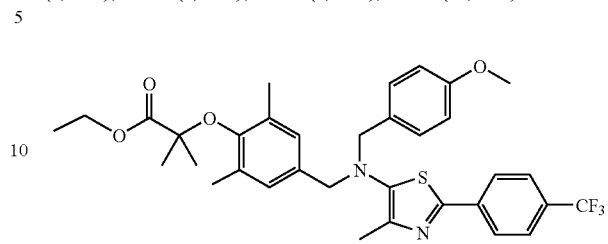

EXAMPLE 18

2-[4-({(4-Methoxy-phenyl)-[4-methyl-2-(4trifluoromethyl-phenyl)-thiazol-5-yl]-amino}-methyl)-2,6-dimethyl-phenoxy]-2-methyl-propionic acid ethyl ester The same method was employed as in the preparation of example 1 but starting from intermediate 28 (860 mg, 2.3 mmol) and intermediate 3 (1.5 g, 2 eq) and gave the title compound (800 mg, 1.28 mmol) as a yellow oil in a 55.5% yield.

$^1$H NMR (300 MHz, CDCl$_3$) δ: 7.93 (d, 2H), 7.62 (d, 2H), 7.17 (d, 2H), 6.86 (s, 2H), 6.79 (d, 2H), 4.27 (q, 2H), 3.96 (s, 2H), 3.92 (s, 2H), 3.76 (s, 3H), 2.18 (s, 3H), 2.15 (s, 6H), 1.43 (s,6H), 1.33 (t, 3H).

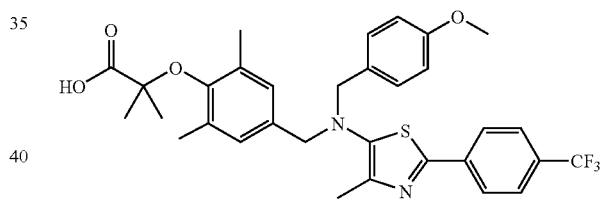

EXAMPLE 19

2-[4-({(4-Methoxy-phenyl)-[4-methyl-2-(4-trifluoromethyl-phenyl)-thiazol-5-yl]-amino}-methyl)-2,6-dimethyl-phenoxy]-2-methyl-propionic acid The same method was employed as in the preparation of example 2 but starting from example 18 to give the title compound as a yellow oil (530 mg, 0.89 mmol) in a 74% yield after purification by flash chromatography using DCM/MeOH (95/05).

[APCI MS] m/z: 599 (MH+)

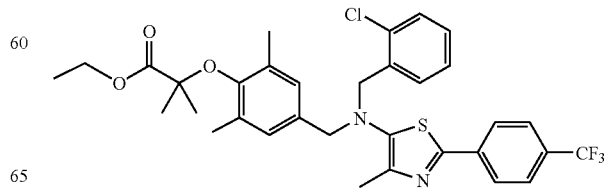

EXAMPLE 20

2-[4-({(2-Chloro-benzyl)-[4-methyl-2-(4-trifluorom-ethyl-phenyl)-thiazol-5-yl]-amino}-methyl)-2,6-dimethyl-phenoxy]-2-methyl-propionic acid ethyl ester The same method was employed as in the preparation of example 1 but starting from intermediate 30 (1 g, 2.6 mmol) and intermediate 3 (1.72 g, 2 eq) and gave the title compound (480 mg, 0.76 mmol) as a orange oil in a 29% yield after purification by flash chromatography using DCM/MeOH (98/02).

$^1$H NMR (300 MHz, CDCl$_3$) δ: 7.93 (d, 2H), 7.64 (d, 2H), 7.34 (d, 1H), 7.26 (m, 1H), 7.17 (m, 2H), 6.88 (s, 2H), 4.27 (q, 2H), 4.15 (s, 2H), 4.00 (s, 2H), 2.14 (s, 6H), 2.10 (s, 3H), 1.43 (s, 6H), 1.33 (t, 3H).

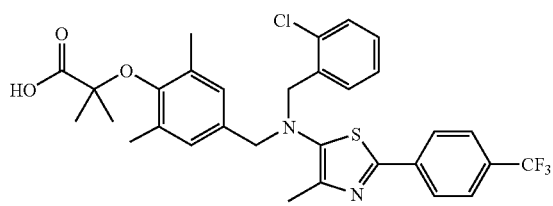

EXAMPLE 21

2-[4-({(2-Chloro-benzyl)-[4-methyl-2-(4-trifluorom-ethyl-phenyl)-thiazol-5-yl]-amino}-methyl)-2,6-dimethyl-phenoxy]-2-methyl-propionic acid The same method was employed as in the preparation of example 2 but starting from example 20 to give the title compound as a white powder (450 mg, 0.75 mmol) in a 98% yield.

[APCI MS] m/z: 603 (MH+) $^1$H NMR (300 MHz, CDCl$_3$) δ: 7.81 (d, 2H), 7.64 (d, 2H), 7.27 (m, 1H), 7.18 (m, 1H), 7.11 (m, 2H), 6.75 (s, 2H), 4.03 (s, 2H), 3.90 (s, 2H), 1.97 (s, 6H), 1.85 (s, 3H), 1.10 (s, 6H).

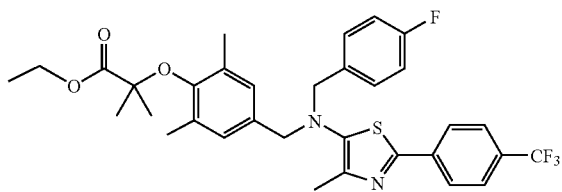

EXAMPLE 22

2-[4-({(4-Fluoro-benzyl)-[4-methyl-2-(4-trifluorom-ethyl-phenyl)-thiazol-5-yl]-amino}-methyl)-2,6-dimethyl-phenoxy]-2-methyl-propionic acid ethyl ester The same method was employed as in the preparation of example 1 but starting from intermediate 32 (1 g, 2.7 mmol) and intermediate 3 (1.8 g, 2 eq) and gave the title compound as a colourless oil directly used after purification by flash chromatography using DCM/MeOH (98/02).

$^1$H NMR (300 MHz, CDCl$_3$) δ: 7.90 (d, 2H), 7.63 (d, 2H), 7.19 (m, 2H), 6.95 (m, 2H), 6.86 (s, 2H), 4.25 (q, 2H), 3.98 (s, 2H), 3.92 (s, 2H), 2.16 (s, 9H), 1.44 (s, 6H), 1.33 (t, 3H).

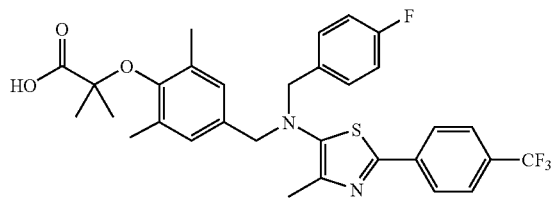

EXAMPLE 23

2-[4-({(4-Fluoro-benzyl)-[4-methyl-2-(4-trifluorom-ethyl-phenyl)-thiazol-5-yl]-amino}-methyl)-2,6-dimethyl-phenoxy]-2-methyl-propionic acid The same method was employed as in the preparation of example 2 but starting from example 22 to give the title compound as a yellow powder (540 mg, 0.92 mmol) in a 34% yield (2 steps).

[APCI MS] m/z: 587 (MH+) $^1$H NMR (300 MHz, DMSO) δ: 8.17 (d, 2H), 8.00 (d, 2H), 7.53 (m, 2H), 7.33 (m, 2H), 7.14 (s, 2H), 4.29 (s, 2H), 4.21 (s, 2H), 2.71 (s, 6H), 2.35 (s, 3H), 1.52 (s, H).

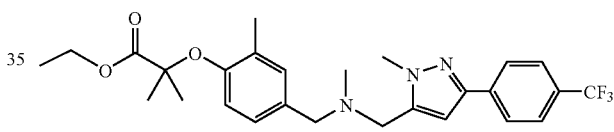

EXAMPLE 24

2-methyl-2-[4-(((1-methyl-3-(4-trifluoromethylphe-nyl))-pyrazol-5-yl)methyl-N-methyl-aminomethyl)phenoxy]propionic acid ethyl ester A mixture of intermediate 49 (0.2 g, 0.79 mmol), intermediate 70 (0.27 g, 1.05 equiv.) and K$_2$CO$_3$ (0.132 g, 1.2 equiv.) in acetone (30 ml) was heated under reflux during 1 hour and then poured into water. After extraction with CH$_2$Cl$_2$, the organic layer was dried over Na$_2$SO$_4$ and then concentrated. The residue was purified by chromatography on silicagel eluting with CH$_2$Cl$_2$/MeOH (98/2). The titled compound was obtained as a colorless oil (0.16 g, 41.06%)

$^1$H NMR (300 MHz, CDCl$_3$): δ 7.85 (d, 2H), 7.65 (d, 2H), 7.2 (d, 2H), 6.9 (d, 2H), 6.5 (s, 1H), 4.25 (q, 2H), 3.9 (s, 3H), 3.55 (s, 2H), 3.5 (s, 2H), 2.2 (s, 3H), 1.6 (s, 6H), 1.25 (t, 3H).

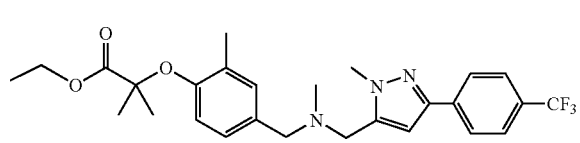

EXAMPLE 25

2-methyl-2-[2-methyl-4-(((1-methyl-3-(4-trifluoromethylphenyl))-pyrazol-5-yl)methyl-N-methyl-aminomethyl)phenoxy]propionic acid ethyl ester The same method was employed as in the preparation of example 24 starting from intermediate 50 and intermediate 70. The title compound was obtained as a colorless oil

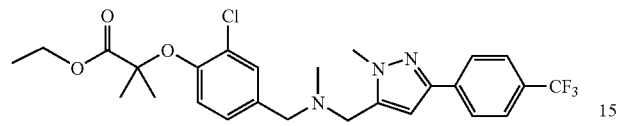

EXAMPLE 26

2-methyl-2-[2-chloro-4-(((1-methyl-3-(4-trifluoromethylphenyl))-pyrazol-5-yl)methyl-N-methyl-aminomethyl)phenoxy]propionic acid ethyl ester The same method was employed as in the preparation of example 24 starting from intermediate 51 (0.27 g, 0.94 mmol) and intermediate 70 intermediate (0.3 g, 1 equiv.). The title compound was obtained as an oil (0.4 g, 80.8%).

$^1$H NMR (300 MHz, CDCl$_3$): δ 7.9 (d, 2H), 7.65 (d, 2H), 7.35 (sd, 1H), 7.1 (dd, 1H), 6.9 (d, 1H), 6.55 (s, 1H), 4.25 (q, 2H), 3.9 (s, 3H), 3.55 (s, 2H), 3.5 (s, 2H), 2.2 (s, 3H), 1.6 (s, 6H), 1.25 (t, 3H).

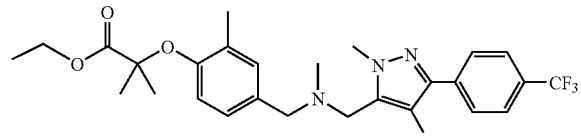

EXAMPLE 27

2-methyl-2-[2-methyl-4-((1,4-dimethyl-3-(4-trifluoromethylphenyl)-pyrazol-5-yl)methyl-N-methyl-aminomethyl)phenoxy]propionic acid ethyl ester The same method was employed as in the preparation of example 24 starting from intermediate 50. The title compound was obtained as a colorless oil

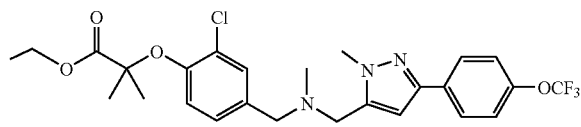

EXAMPLE 28

2-methyl-2-[2-chloro-4-((1-methyl-3-(4-trifluoromethoxyphenyl)-pyrazol-5-yl)methyl-N-methyl-aminomethyl)phenoxy]propionic acid ethyl ester The same method was employed as in the preparation of example 24 starting from intermediate 50 and. The title compound was obtained as a colorless oil (X g, X %).

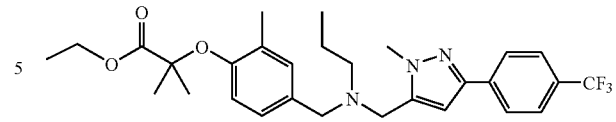

EXAMPLE 29

2-methyl-2-[2-methyl-4-((1-methyl-3-(4-trifluoromethylphenyl)-pyrazol-5-yl)methyl-N-propyl-aminomethyl)phenoxy]propionic acid ethyl ester The same method was employed as in the preparation of example 24 starting from intermediate 52 (0.24 g, 0.82 mmol) and intermediate 70 (0.26 g, 0.82 mmol). The title compound was obtained as an oil (0.41 g, 94.26%).

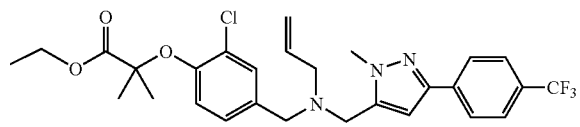

EXAMPLE 30

2-methyl-2-[2-chloro-4-((1-methyl-3-(4-trifluoromethylphenyl)-pyrazol-5-yl)methyl-N-(propen-2-yl)-aminomethyl)phenoxy]propionic acid ethyl ester The same method was employed as in the preparation of example 24 starting from intermediate 45 (0.3 g, 0.96 mmol) and intermediate 70 (0.31 g, 0.96 mmol). The title compound was obtained as an oil (0.36 g, 68.02%).

$^1$H NMR (300 MHz, CDCl$_3$): δ 7.9 (d, 2H), 7.65 (d, 2H), 7.35 (sd, 1H), 7.05 (dd, 1H), 6.85 (d, 1H), 6.5 (s, 1H), 5.8 (m, 1H), 5.2 (m, 2H), 4.25 (q, 2H), 3.9 (s, 3H), 3.6 (s, 2H), 3.45 (s, 2H), 3.1 (m, 2H), 1.6 (s, 6H), 1.25 (t, 3H).

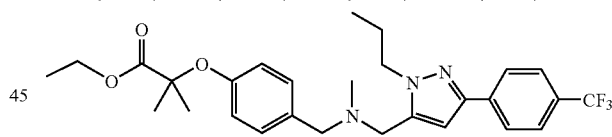

EXAMPLE 31

2-methyl-2-[4-((1-propyl-3-(4-trifluoromethylphenyl)-pyrazol-5-yl)methyl-N-methyl-aminomethyl)phenoxy]propionic acid ethyl ester The same method was employed as in the preparation of example 24 starting from intermediate 49 and intermediate 71. The title compound was obtained as an oil

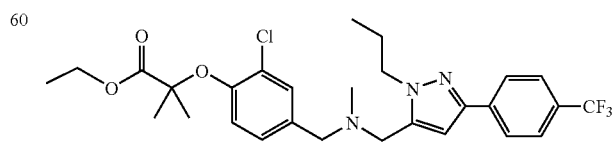

EXAMPLE 32

2-methyl-2-[2-chloro-4-((1-propyl-3-(4-trifluoromethylphenyl)-pyrazol-5-yl)methyl-N-methyl-aminomethyl)phenoxy]propionic acid ethyl ester The same method was employed as in the preparation of example 24 starting from intermediate 51 and intermediate 71. The title compound was obtained as an oil

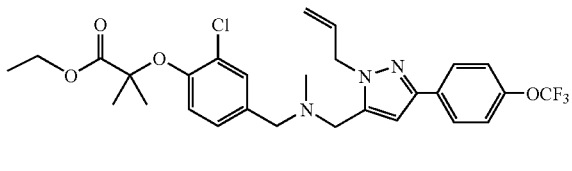

EXAMPLE 33

2-methyl-2-[2-chloro-4-((1-(propen-2-yl)-3-(4-trifluoromethoxyphenyl-pyrazol-5-yl)methyl-N-methyl-aminomethyl)phenoxy]propionic acid ethyl ester The same method was employed as in the preparation of example 24 starting from intermediate 51 (0.3 g, 1.05 mmol) and intermediate 72 (0.38 g, 1.05 mmol). The title compound was obtained as an oil (0.42 g, 70.68%).

$^1$H NMR (300 MHz, CDCl$_3$): δ 7.85 (d, 2H), 7.35 (sd, 1H), 7.25 (d, 2H), 7.05 (dd, 1H), 6.85 (d, 1H), 6.45 (s, 1H), 6 (m, 1H), 5.05 (m, 2H), 4.9 (m, 2H), 4.25 (q, 2H), 3.45 (s, 2H), 3.35 (s, 2H), 2.2 (s, 3H), 1.55 (s, 6H), 1.3 (t, 3H).

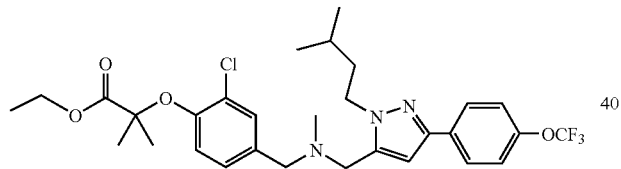

EXAMPLE 34

2-methyl-2-[2-chloro-4-((1-(3-methyl-butyl)-3-(4-trifluoromethoxyphenyl)-pyrazol-5-yl)methyl-N-methyl-aminomethyl)phenoxy]propionic acid ethyl ester The same method was employed as in the preparation of example 24 starting from intermediate 51 (0.24 g, 0.84 mmol) and intermediate 73 (0.33 g, 0.84 mmol). The title compound was obtained as an oil (0.43 g, 85.89%).

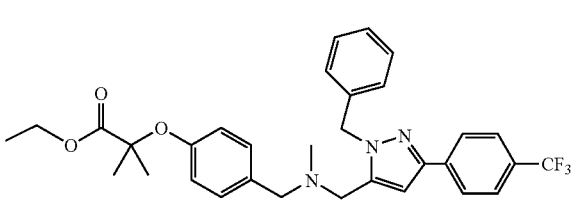

EXAMPLE 35

2-methyl-2-[4-((1-benzyl-3-(4-trifluoromethylphenyl)-pyrazol-5-yl)methyl-N-methyl-aminomethyl)phenoxy]propionic acid ethyl ester The same method was employed as in the preparation of example 24 starting from intermediate 49 and intermediate 74 The title compound was obtained as an oil.

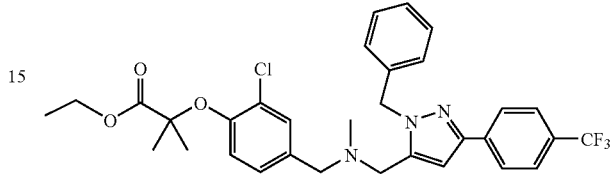

EXAMPLE 36

2-methyl-2-[2-chloro-4-((1-benzyl-3-(4-trifluoromethylphenyl)-pyrazol-5-yl)methyl-N-methyl-aminomethyl)phenoxy]propionic acid ethyl ester The same method was employed as in the preparation of example 24 starting from intermediate 51 and intermediate 74. The title compound was obtained as an oil

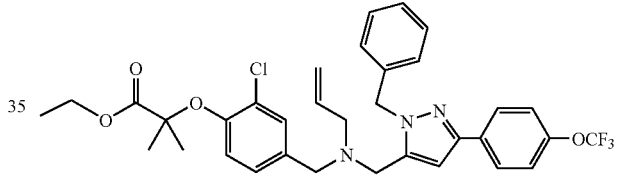

EXAMPLE 37

2-methyl-2-[2-chloro-4-((1-benzyl-3-(4-trifluoromethoxyphenyl)-pyrazol-5-yl)methyl-N-(propen-2-yl)aminomethyl)phenoxy]propionic acid ethyl ester The same method was employed as in the preparation of example 24 starting from intermediate 45 (0.2 g, 0.64 mmol) and intermediate 75 (0.27 g, 0.64 mmol). The title compound was obtained as an oil (0.31 g, 75.26%).

$^1$H NMR (300 MHz, CDCl$_3$): δ 7.85 (d, 2H), 7.25 (m, 6H), 7.05 (m, 3H), 6.8 (d, 1H), 6.5 (s, 1H), 5.75 (m, 1H), 5.4 (s, 2H), 5.25 (m, 2H); 4.25 (q, 2H), 3.5 (s, 2H), 3.45 (s, 2H), 3 (m, 2H), 1.6 (s, 6H), 1.25 (t, 3H).

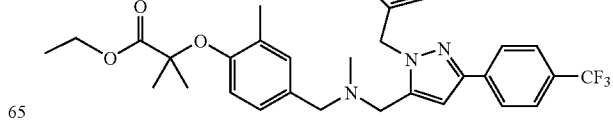

EXAMPLE 38

2-methyl-2-[2-methyl-4-((1-(4-methoxybenzyl)-3-(4-trifluoromethylphenyl)-pyrazol-5-yl)methyl-N-methyl-aminomethyl)phenoxy]propionic acid ethyl ester The same method was employed as in the preparation of example 24 starting from intermediate 50. The title compound was obtained as an oil

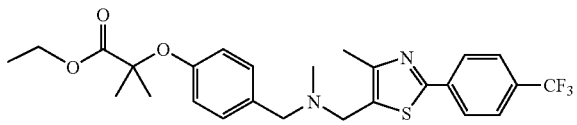

EXAMPLE 39

2-methyl-2-[4-{[(4-methyl-2-[4-trifluoromethylphenyl]-thiazol-5-ylmethyl)-N-methyl-amino]methyl}phenoxy]propionic acid ethyl ester The same method was employed as in the preparation of example 24 starting from intermediate 49 and intermediate 78 The title compound was obtained as an oil

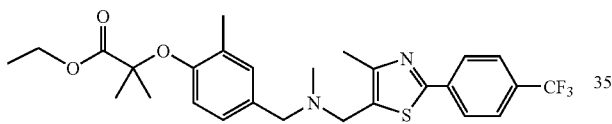

EXAMPLE 40

2-methyl-2-[2-methyl-4-{[(4-methyl-2-[4-trifluoromethylphenyl]-thiazol-5-ylmethyl)-N-methyl-amino]methyl}phenoxy]propionic acid ethyl ester The same method was employed as in the preparation of example 24 starting from intermediate 50 and intermediate 78. The title compound was obtained as an oil

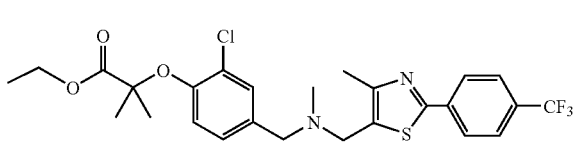

EXAMPLE 41

2-methyl-2-[2-chloro-4-{[(4-methyl-2-[4-trifluoromethylphenyl]-thiazol-5-ylmethyl)-N-methyl-amino]methyl}phenoxy]propionic acid ethyl ester The same method was employed as in the preparation of example 24 starting from intermediate 51 and intermediate 78. The title compound was obtained as an oil

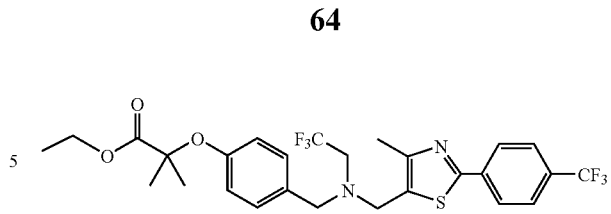

EXAMPLE 42

2-methyl-2-[4-{[(4-methyl-2-[4-trifluoromethylphenyl]-thiazol-5-ylmethyl)-N-(2,2,2-trifluoroethyl)amino]methyl}phenoxy]propionic acid ethyl ester The same method was employed as in the preparation of example 24 starting from intermediate 41 (0.31 g, 0.97 mmol) and intermediate 78 (0.32 g, 0.97 mmol). The title compound was obtained as an oil (0.39 g, 69.92%).
$^1$H NMR (300 MHz, CDCl$_3$): δ 8.05 (d, 2H), 7.65 (d, 2H), 7.25 (d, 2H), 6.8 (d, 2H), 4.25 (q, 2H), 3.95 (s, 2H), 3.8 (s, 2H), 3.15 (q, 2H), 2.4 (s, 3H), 1.6 (s, 6H), 1.25 (t, 3H).

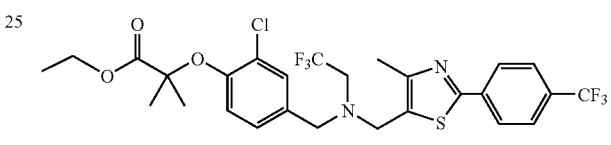

EXAMPLE 43

2-methyl-2-[2-chloro-4-{[(4-methyl-2-[4-trifluoromethylphenyl]-thiazol-5-ylmethyl)-N-(2.22-trifluoroethyl)amino]methyl}phenoxy]propionic acid ethyl ester The same method was employed as in the preparation of example 24 starting from intermediate 42 (0.3 g, 0.85 mmol) and intermediate 78 (0.285 g, 0.85 mmol). The title compound was obtained as an oil (0.48 g, 92.95%).
$^1$H NMR (300 MHz, CDCl$_3$): δ 8.05 (d, 2H), 7.75 (d, 2H), 7.4 (sd, 1H), 7.15 (dd, 1H), 6.9 (d, 1H), 4.25 (q, 2H), 4 (s, 2H), 3.85 (s, 2H), 3.2 (q, 2H), 2.45 (s, 3H), 1.6 (s, 6H), 1.3 (t, 3H).

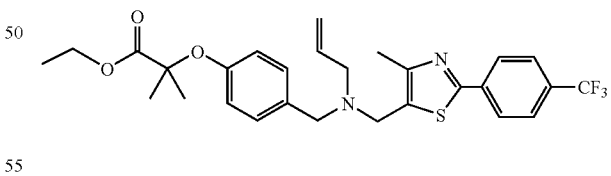

EXAMPLE 44

2-methyl-2-[4-{[(4-methyl-2-[4-trifluoromethylphenyl]-thiazol-5-ylmethyl)-N-(propen-2-yl)amino]methyl}phenoxy]propionic acid ethyl ester The same method was employed as in the preparation of example 24 starting from intermediate 43 (0.35 g, 1.26 mmol) and intermediate 78 (0.42 g, 1.26 mmol). The title compound was obtained as an ecru solid (0.6 g, 89.26%).
Mp: 68° C.

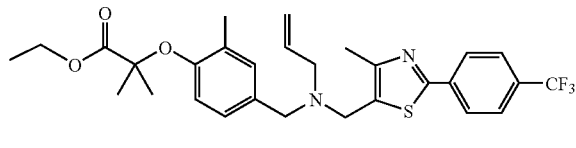

EXAMPLE 45

2-methyl-2-[2-methyl-4-{[(4-methyl-2-[4-trifluoromethylphenyl]-thiazol-5-ylmethyl)-N-(propen-2-yl)amino]methyl}phenoxy]propionic acid ethyl ester The same method was employed as in the preparation of example 24 starting from intermediate 44 (0.3 g, 1.03 mmol) and intermediate 78 (0.35 g, 1.03 mmol). The title compound was obtained as an oil (0.4 g, 71.06%).

$^1$H NMR (300 MHz, CDCl$_3$): δ 8 (d, 2H), 7.7 (d, 2H), 7.15 (sd, 1H), 7.05 (dd, 1H), 6.7 (d, 1H), 5.9 (m, 1H), 5.25 (m, 2H), 4.25 (q, 2H), 3.7 (s, 2H), 3.55 (s, 2H), 3.1 (m, 2H), 2.4 (s, 3H), 2.25 (s, 3H), 1.55 (s, 6H), 1.25 (t, 3H).

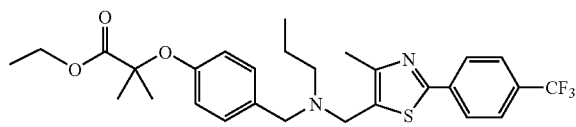

EXAMPLE 46

2-methyl-2-[4-{[(4-methyl-2-[4-trifluoromethylphenyl]-thiazol-5-ylmethyl)-N-(propen-2-yl)amino]methyl}phenoxy]propionic acid ethyl ester The same method was employed as in the preparation of example 24 The title compound was obtained as an oil

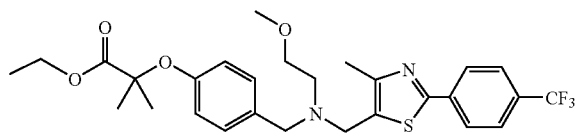

EXAMPLE 47

2-methyl-2-[4-{[(4-methyl-2-[4-trifluoromethylphenyl]-thiazol-5-ylmethyl)-N-(2-methoxyethyl)amino]methyl}phenoxy]propionic acid ethyl ester The same method was employed as in the preparation of example 24 starting from intermediate 46 (0.3 g, 1.02 mmol) and intermediate 78 (0.34 g, 1.02 mmol). The title compound was obtained as an oil (0.56 g, 99%).

$^1$H NMR (300 MHz, CDCl$_3$): δ 8 (d, 2H), 7.65 (d, 2H), 7.2 (d, 2H), 6.75 (d, 2H), 4.2 (q, 2H), 3.75 (s, 2H), 3.6 (s, 2H), 3.45 (t, 2H), 3.3 (s, 3H), 2.7 (t, 2H), 2.35 (s, 3H), 1.6 (s, 6H), 1.2 (t, 3H).

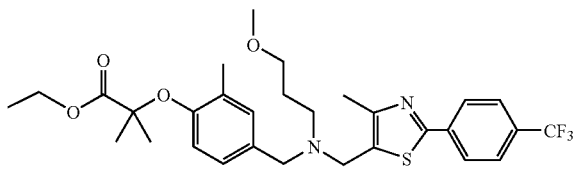

EXAMPLE 48

2-methyl-2-[2-methyl-4-{[(4-methyl-2-[4-trifluoromethylphenyl]-thiazol-5-ylmethyl)-N-(3-methoxypropyl)amino]methyl}phenoxy]propionic acid ethyl ester The same method was employed as in the preparation of example 24 starting from intermediate 47 (0.3 g, 0.93 mmol) and intermediate 78 (0.312 g, 0.93 mmol). The title compound was obtained as an oil (0.53 g, 98.72%).

$^1$H NMR (300 MHz, CDCl$_3$): δ 8.05 (d, 2H), 7.7 (d, 2H), 7.1 (sd, 1H), 7.05 (dd, 1H), 6.65 (d, 1H), 4.25 (q, 2H), 3.7 (s, 2H), 3.55 (s, 2H), 3.4 (t, 2H), 3.3 (s, 3H), 2,6 (m, 2H), 2.4 (s, 3H), 2.25 (s, 3H), 1.8 (m, 2H), 1.6 (s, 6H), 1.25 (t, 3H).

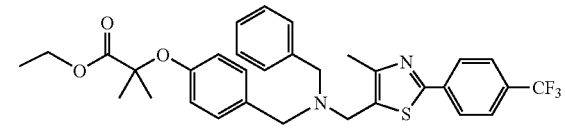

EXAMPLE 49

2-methyl-2-[4-{[(4-methyl-2-[4-trifluoromethylphenyl]-thiazol-5-ylmethyl)-N-(benzyl)-amino]methyl}phenoxy]propionic acid ethyl ester The same method was employed as in the preparation of example 24 The title compound was obtained as an oil

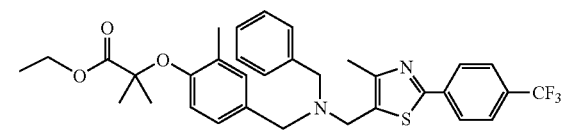

EXAMPLE 50

2-methyl-2-[2-methyl-4-{[(4-methyl-2-[4-trifluoromethylphenyl]-thiazol-5-ylmethyl-N-(benzyl)-amino]methyl}phenoxy]propionic acid ethyl ester The same method was employed as in the preparation of example 24 The title compound was obtained as an oil

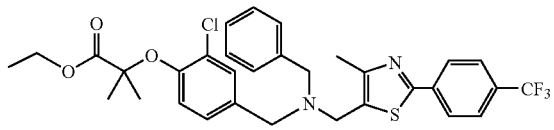

EXAMPLE 51

2-methyl-2-[2-chloro-4-{[(4-methyl-2-[4trifluoromethylphenyl]-thiazol-5-ylmethyl)-N-(benzyl)-amino]methyl}phenoxy]propionic acid ethyl ester The same method was employed as in the preparation of example 24 starting from intermediate 53 (0.3 g, 0.83 mmol) and intermediate 78 (0.28 g, 0.83 mmol). The title compound was obtained as an oil (0.35 g, 68.41%).

$^1$H NMR (300 MHz, CDCl$_3$): δ 8.05 (d, 2H), 7.7 (d, 2H), 7.4 (m, 6H), 7.15 (dd, 1H), 6.9 (d, 1H), 4.25 (q, 2H), 3.65 (s, 2H), 3.6 (s, 2H), 3.55 (s, 2H), 2.4 (s, 3H), 1.6 (s, 6H), 1.25 (t, 3H).

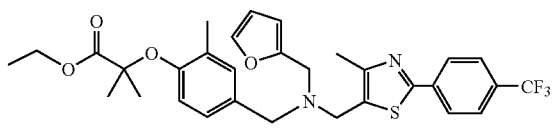

EXAMPLE 52

2-methyl-2-[2-methyl-4-{[(4-methyl-2-[4-trifluoromethylphenyl]-thiazol-5-ylmethyl)-N-(furan-2-ylmethyl)-amino]methyl}phenoxy]propionic acid ethyl ester The same method was employed as in the preparation of example 24 starting from intermediate 53 (0.3 g, 0.91 mmol) and intermediate 78 (0.304 g, 0.91 mmol). The title compound was obtained as an oil (0.49 g, 92.26%).

$^1$H NMR (300 MHz, CDCl$_3$): δ 8.05 (d, 2H), 7.7 (d, 2H), 7.45 (sd, 1H), 7.15 (sd, 1H), 7.05 (dd, 1H), 6.65 (d, 1H), 6.35 (sd, 1H), 6.2 (sd, 1H), 4.25 (q, 2H), 3.75 (s, 2H), 3.7 (s, 2H), 3.6 (s, 2H), 2.4 (s, 3H), 2.25 (s, 3H), 1.6 (s , 6H), 1.25 (t, 3H).

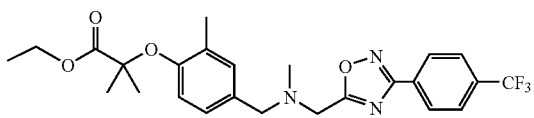

EXAMPLE 53

2-methyl-2-[2-methyl-4-((3-(4-trifluoromethyl-phenyl)-[1,2,4]-oxadiazol-5-yl)methyl-N-methyl-aminomethyl)phenoxy]propionic acid ethyl ester The same method was employed as in the preparation of example 24 starting from intermediate 50. The title compound was obtained as an oil

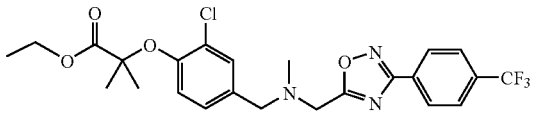

EXAMPLE 54

2-methyl-2-[2-chloro-4-((3-(4-trifluoromethyl-phenyl)-[1,2,4]-oxadiazol-5-yl)methyl-N-methyl-aminomethyl)phenoxy]propionic acid ethyl ester The same method was employed as in the preparation of example 24 starting from intermediate 51 (0.32 g, 1.12 mmol) The title compound was obtained as an oil (0.38 g, 66.28%).

$^1$H NMR (300 MHz, CDCl$_3$): δ 8.25 (d, 2H), 7.8 (d, 2H), 7.45 (sd, 1H), 7.15 (dd, 1H), 6.85 (d, 1H), 4.25 (q, 2H), 3.95 (s, 2H), 3.65 (s, 2H), 2.45 (s, 3H), 1.65 (s, 6H), 1.3 (t, 3H).

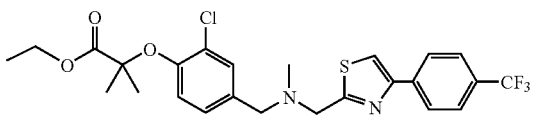

EXAMPLE 55

2-methyl-2-[2-chloro-4-((4-(4-trifluoromethyl-phenyl)-thiazol-2-yl)methyl-N-methyl-aminomethyl)phenoxy]propionic acid ethyl ester The same method was employed as in the preparation of example 24 starting from intermediate 51 (0.3 g, 1.05 mmol) The title compound was obtained as an oil (0.3 g, 54.22%).

$^1$H NMR (300 MHz, CDCl$_3$): δ 8 (d, 2H), 7.65 (d, 2H), 7.55 (s, 1H), 7.4 (sd, 1H), 7.1 (dd, 1H), 6.85 (d, 1H), 4.25 (q, 2H), 3.85 (s, 2H), 3.55 (s, 2H), 2.35 (s, 3H), 1.55 (s, 6H), 1.25 (t, 3H).

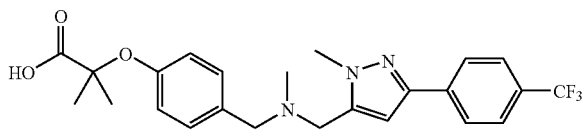

EXAMPLE 56

2-methyl-2-[4-(((1-methyl-3-(4-trifluoromethylphenyl))-pyrazol-5-yl)methyl-N-methyl-aminomethyl)phenoxy]propionic acid A mixture of example 24 (0.16 g, 0.33 mmol ) and NaOH 1N (0.65 mL, 2 equiv.) in EtOH (20 mL) was heated at 60° C. overnight and then cooled. A solution of HCl 1N (0.65 mL) was added and the solution was concentrated to dryness. The residue was taken up in a mixture of CH$_2$Cl$_2$/MeOH (9/1), the salts were filtered off, and the filtrate concentrated to dryness, to afford a solid. After crystallisation from diisopropyloxyde, the title compound was obtained as yellow crystals (0.065 g, 43.1%)

Mp: 216° C. $^1$H NMR (300 MHz, CDCl$_3$): δ 10.5 (s, 1H), 7.7 (d, 2H), 7.55 (d, 2H), 7.3 (d, 2H), 6.95 (s, 1H), 6.7 (d, 2H), 4.25 and 4.05 (m, 4H), 3.7 (s, 3H), 2.3 (s, 3H), 1.3 (s, 6H).

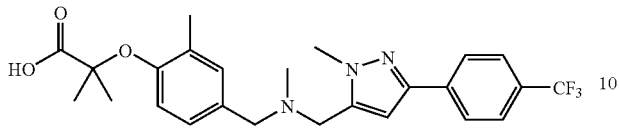

EXAMPLE 57

2-methyl-2-[2-methyl-4-(((1-methyl-3-(4-trifluoromethylphenyl))-pyrazol-5-yl)methyl-N-methyl-aminomethyl)phenoxy]propionic acid The same method was employed as in the preparation of example 56 starting from example 25. The title compound was obtained as a white solid

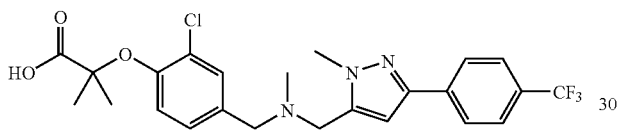

EXAMPLE 58

2-methyl-2-[2-chloro-4-(((1-methyl-3-(4-trifluoromethylphenyl)-pyrazol-5-yl)methyl-N-methyl-aminomethyl)phenoxy]propionic acid The same method was employed as in the preparation of example 56 starting from example 26 (0.4 g, 0.76 mmol). The title compound was obtained as a white solid
Mp: 157° C.

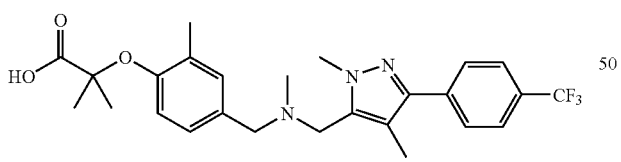

EXAMPLE 59

2-methyl-2-[2-methyl-4-(((1,4-dimethyl-3-(4-trifluoromethylphenyl))-pyrazol-5-yl)methyl-N-methyl-aminomethyl)phenoxy]propionic acid The same method was employed as in the preparation of example 56 starting from example 27 The title compound was obtained as a white solid

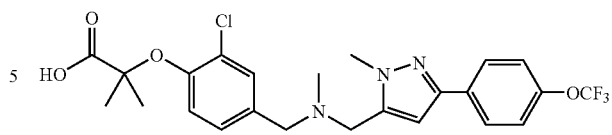

EXAMPLE 60

2-methyl-2-[2-chloro-4-(((1-methyl-3-(4-trifluoromethoxyphenyl))-pyrazol-5-yl)methyl-N-methyl-aminomethyl)phenoxy]propionic acid The same method was employed as in the preparation of example 56 starting from example 28. The title compound was obtained as a white solid

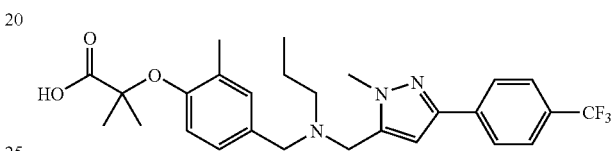

EXAMPLE 61

2-methyl-2-[2-methyl-4-(((1-methyl-3-(4-trifluoromethylphenyl))-pyrazol-5-yl)methyl-N-propyl-aminomethyl)phenoxy]propionic acid The same method was employed as in the preparation of example 56 starting from example 29 (0.41 g, 0.77 mmol). The title compound was obtained as a white solid (0.13 g, 33.47%).
Mp: 184° C.

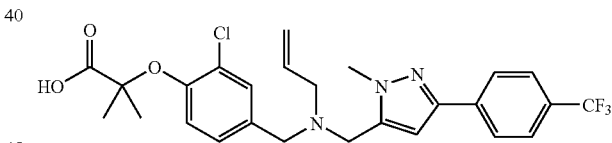

EXAMPLE 62

2-methyl-2-[2-chloro-4-(((1-methyl-3-(4-trifluoromethylphenyl))-pyrazol-5-yl)methyl-N-(propen-2-yl)-aminomethyl)phenoxy]propionic acid The same method was employed as in the preparation of example 56 starting from example 30 (0.36 g, 0.65 mmol). The title compound was obtained as a white solid (0.24 g, 70.25%).
Mp: 162° C.

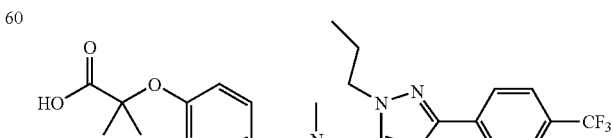

EXAMPLE 63

2-methyl-2-[4-(((1-propyl-3-(4-trifluoromethylphenyl))-pyrazol-5-yl)methyl-N-methyl-aminomethyl)phenoxy]propionic acid The same method was employed as in the preparation of example 56 starting from example 31. The title compound was obtained as a white solid

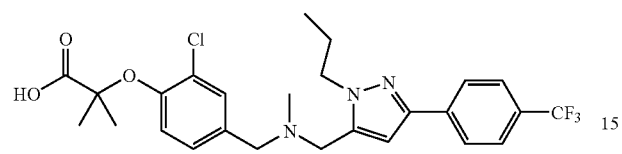

EXAMPLE 64

2-methyl-2-[2-chloro-4-(((1-propyl-3-(4-trifluoromethylphenyl))-pyrazol-5-yl)methyl-N-methyl-aminomethyl)phenoxy]propionic acid The same method was employed as in the preparation of example 56 starting from example 31. The title compound was obtained as a white solid

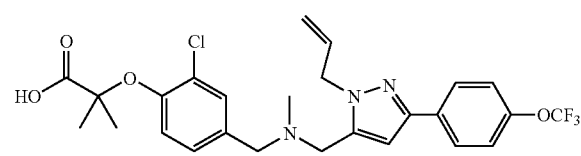

EXAMPLE 65

2-methyl-2-[2-chloro-4-(((1-(propen-2yl)-3-(4-trifluoromethoxyphenyl))-pyrazol-5-yl)methyl-N-methyl-aminomethyl)phenoxy]propionic acid The same method was employed as in the preparation of example 56 starting from example 33 (0.42 g, 0.74 mmol). The title compound was obtained as a white solid (0.31 g, 77.65%).
Mp: 173° C.

EXAMPLE 66

2-methyl-2-[2-chloro-4-(((1-(methyl-3-butyl)-3-(4-trifluoromethoxyphenyl))-pyrazol-5-yl)methyl-N-methyl-aminomethyl)phenoxy]propionic acid The same method was employed as in the preparation of example 56 starting from example 34 (0.43 g, 7.22 mmol).

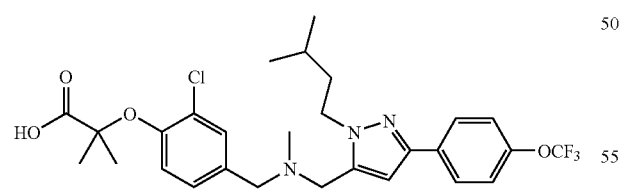

The title compound was obtained as a white solid (0.16 g, 39.05%).
Mp: 90° C.

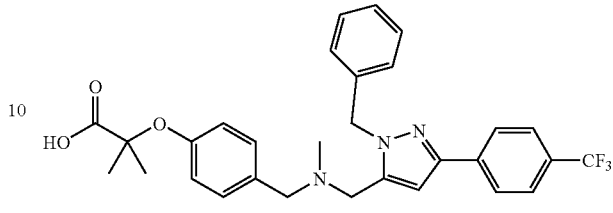

EXAMPLE 67

2-methyl-2-[4-(((1-benzyl-3-(4-trifluoromethylphenyl))-pyrazol-5-yl)methyl-N-methyl-aminomethyl)phenoxy]propionic acid The same method was employed as in the preparation of example 56 starting from example 35. The title compound was obtained as a white solid

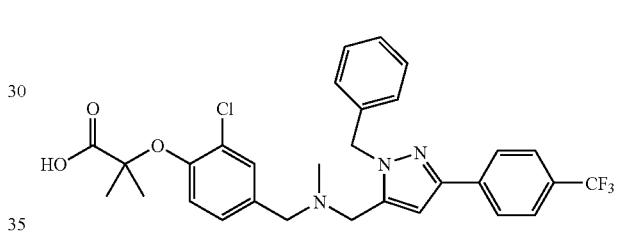

EXAMPLE 68

2-methyl-2-[2-chloro-4-(((1-benzyl-3-(4-trifluoromethylphenyl))-pyrazol-5-yl)methyl-N-methyl-aminomethyl)phenoxy]propionic acid The same method was employed as in the preparation of example 56 starting from example 36. The title compound was obtained as a white solid

EXAMPLE 69

2-methyl-2-[2-chloro-4-(((1-benzyl-3-(4-trifluoromethylphenyl))-pyrazol-5-yl)methyl-N-(propen-2-yl)-aminomethyl)phenoxy]propionic acid

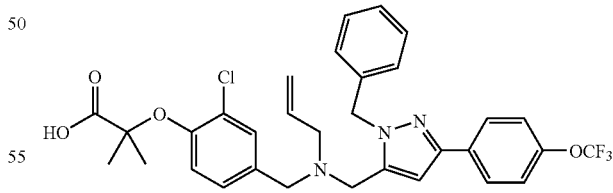

The same method was employed as in the preparation of example 56 starting from example 37 (0.31 g, 0.48 mmol).

The title compound was obtained as a white solid (0.26 g, 87.71%).

Mp: 130° C.

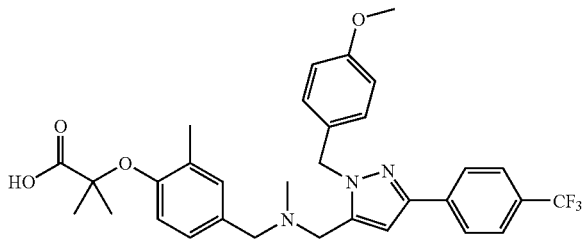

EXAMPLE 70

2-methyl-2-[2-methyl-4-(((1-(4-methoxybenzyl)-3-(4-trifluoromethylphenyl))-pyrazol-5-yl)methyl-N-methyl-aminomethyl)phenoxy]propionic acid The same method was employed as in the preparation of example 56 starting from example 38. The title compound was obtained as a white solid

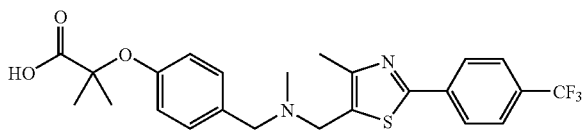

EXAMPLE 71

2-methyl-2-[4-{[(4-methyl-2-[4-trifluoromethylphenyl]-thiazol-5-ylmethyl)-N-methyl-amino]methyl}phenoxy]propionic acid The same method was employed as in the preparation of example 56 starting from example 39. The title compound was obtained as a white solid.

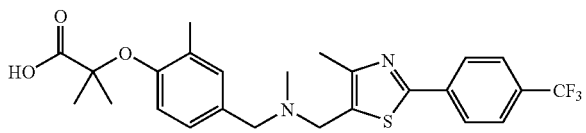

EXAMPLE 72

2-methyl-2-[2-methyl-4-{[(4-methyl-2-[4-trifluoromethylphenyl]-thiazol-5-ylmethyl)-N-methyl-amino]methyl}phenoxy]propionic acid The same method was employed as in the preparation of example 56 starting from example 40. The title compound was obtained as a white solid.

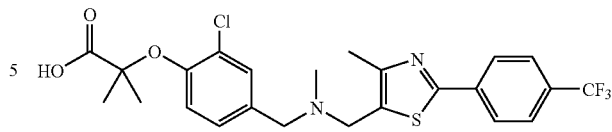

EXAMPLE 73

2-methyl-2-[2-chloro-4-{[(4methyl-2-[4-trifluoromethylphenyl]-thiazol-5-ylmethyl)-N-methyl-amino]methyl}phenoxy]propionic acid The same method was employed as in the preparation of example 56 starting from example 41. The title compound was obtained as a white solid.

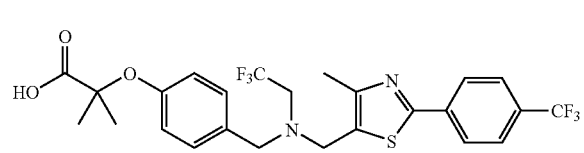

EXAMPLE 74

2-methyl-2-[4-{[(4methyl-2-[4-trifluoromethylphenyl]-thiazol-5-ylmethyl)-N-(2,2,2-trifluoroethyl)-amino]methyl}phenoxy]propionic acid The same method was employed as in the preparation of example 56 starting from example 42 (0.39 g, 0.68 mmol). The title compound was obtained as ecru crystals (251 mg, 67.66%).

Mp: 130–132° C.

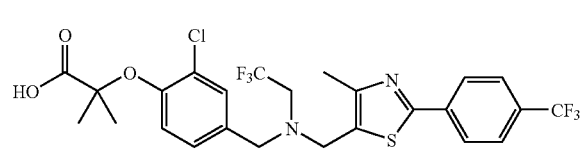

EXAMPLE 75

2-methyl-2-[2-methyl-4-{[(4-methyl-2-[4-trifluoromethylphenyl]-thiazol-5-ylmethyl)-N-(2,2,2-trifluoroethyl)-amino]methyl}phenoxy]propionic acid The same method was employed as in the preparation of example 56 starting from example 43 (0.48 g, 0.79 mmol). The title compound was obtained ecru crystals (0.296 g, 64.64%).

Mp: 118–120° C.

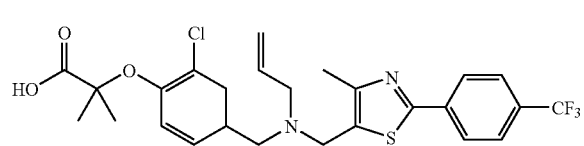

EXAMPLE 76

2-methyl-2-[4-{[(4-methyl-2-[4-trifluoromethylphenyl]-thiazol-5-ylmethyl)-N-(propen-2-yl)-amino]methyl}phenoxy]propionic acid The same method was employed as in the preparation of example 56 starting from example 44 (0.6 g, 1.13 mmol). The title compound was obtained as ecru crystals (0.55 g, 90.22%).
Mp: 110° C.

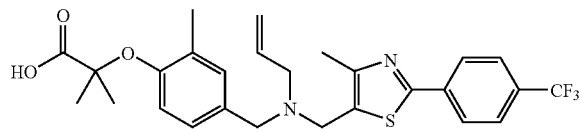

EXAMPLE 77

2-methyl-2-[2-methyl-4-{[(4-methyl-2-[4-trifluoromethylphenyl]-thiazol-5-ylmethyl)-N-(propen-2-yl)-amino]methyl}phenoxy]propionic acid The same method was employed as in the preparation of example 56 starting from example 45 0.4 g, 0.73 mmol). The title compound was obtained as light yellow crystals (0.275 g, 72.47%).
Mp: 119° C.

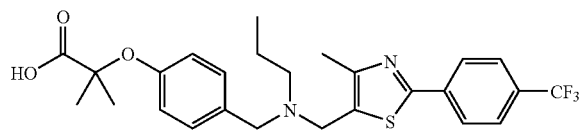

EXAMPLE 78

2-methyl-2-[4-{[(4-methyl-2-[4-trifluoromethylphenyl]-thiazol-5-ylmethyl)-N-(propyl)-amino]methyl}phenoxy]propionic acid The same method was employed as in the preparation of example 56 starting from example 46. The title compound was obtained as light yellow crystals

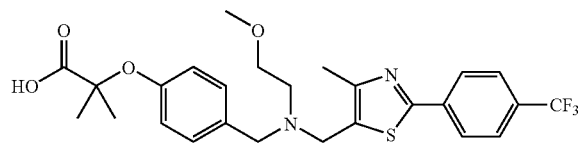

EXAMPLE 79

2-methyl-2-[4-{[(4methyl-2-[4-trifluoromethylphenyl]-thiazol-5-ylmethyl)-N-(2-methoxyethyl)-amino]methyl}phenoxy]propionic acid The same method was employed as in the preparation of example 56 starting from example 47 (0.56 g, 1.02 mmol).

The title compound was obtained as white crystals (0.46 g, 86.55%).
Mp: 160° C.

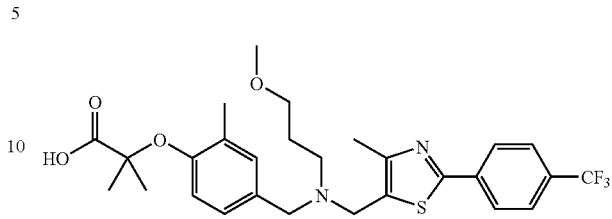

EXAMPLE 80

2-methyl-2-[2-methyl-4-{[(4-methyl-2-[4-trifluoromethylphenyl]-thiazol-5-ylmethyl)-N-(3-methoxypropyl)-amino]methyl}phenoxy]propionic acid The same method was employed as in the preparation of example 56 starting from example 48 (0.53 g, 0.92 mmol). The title compound was obtained as white to crystals (0.403 g, 79.91%).
Mp: 106° C.

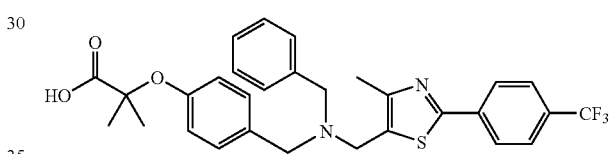

EXAMPLE 81

2-methyl-2-[4-{[(4methyl-2-[4-trifluoromethylphenyl]-thiazol-5-ylmethyl)-N-(benzyl)-amino]methyl}phenoxy]propionic acid The same method was employed as in the preparation of example 56 starting from example 49. The title compound was obtained as light yellow crystals

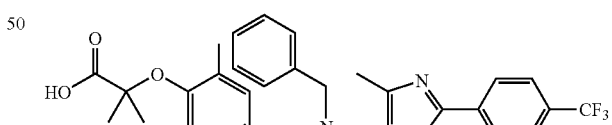

EXAMPLE 82

2-methyl-2-[2-methyl-4-{[(4-methyl-2-[4-trifluoromethylphenyl]-thiazol-5-ylmethyl)-N-(benzyl)-amino]methyl}phenoxy]propionic acid The same method was employed as in the preparation of example 56 starting from example 50. The title compound was obtained as light yellow crystals.

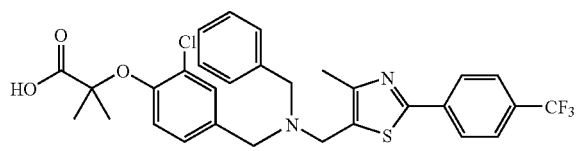

EXAMPLE 83

2-methyl-2-[2chloro-4-{[(4-methyl-2-[4-trifluoromethylphenyl]-thiazol-5-ylmethyl)-N-(benzyl)-amino]methyl}phenoxy]propionic acid The same method was employed as in the preparation of example 56 starting from example 51 (0.35 g, 0.57 mmol). The title compound was obtained as white crystals (0.261 g, 78.12%).
Mp: 111° C.

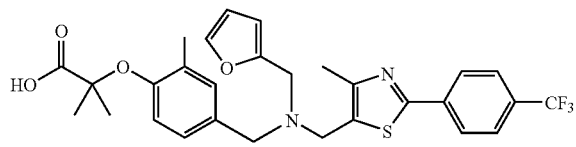

EXAMPLE 84

2-methyl-2-[2-methyl-4-{[(4-methyl-2-[4trifluoromethylphenyl]-thiazol-5-ylmethyl)-N-(furan-2-ylmethyl)-amino]methyl}phenoxy]propionic acid The same method was employed as in the preparation of example 56 starting from example 52 (0.49 g, 0.84 mmol). The title compound was obtained as light yellow crystals (0.206 g, 44.15%)).
Mp: 90° C.

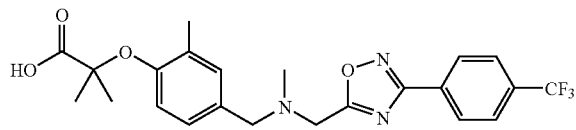

EXAMPLE 85

2-methyl-2-[2-methyl-4-((3-(4-trifluoromethyl-phenyl)-[1,2,4]-oxadiazol-5-yl)methyl-N-methyl-aminomethyl)phenoxy]propionic acid The same method was employed as in the preparation of example 56 starting from example 53. The title compound was obtained as light yellow crystals.

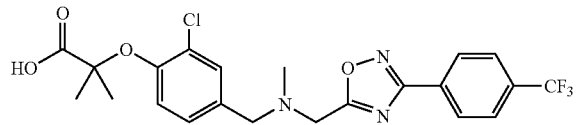

EXAMPLE 86

2-methyl-2-[2-chloro-4-((3-(4-trifluoromethyl-phenyl)-[1,2,4]-oxadiazol-5-yl)methyl-N-methyl-aminomethyl)phenoxy]propionic acid The same method was employed as in the preparation of example 56 starting from example 54 (0.38 g, 0.74 mmol). The title compound was obtained as light yellow crystals (0.3 g, 83.52%).
Mp: 156–158° C.

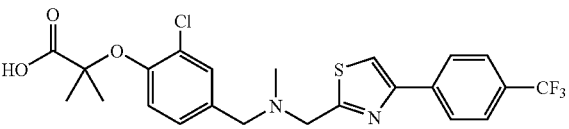

EXAMPLE 87

2-methyl-2-[2chloro-4-((4-(4-trifluoromethyl-phenyl)-thiazol-2-yl)methyl-N-methyl-aminomethyl)phenoxy]propionic acid The same method was employed as in the preparation of example 56 starting from example 55 (0.3 g, 0.57 mmol). The title compound was obtained as light yellow crystals (0.16 g, 56.33%).
Mp: 90° C.

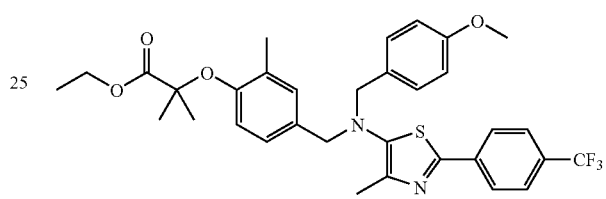

EXAMPLE 88 trifluoromethylphenyl)thiazol-5-yl]amino)methyl}-2-methylphenoxy)propionic acid ethyl ester To a solution of intermediate 28 (1.91 g, 5.05 mmol) in 3-methylbutan-2-one (20 mL) was added intermediate 39 (1.27 g, 0.8 eq.) and $Cs_2CO_3$ (2.14 g, 1.3 eq.) and the reaction was stirred to reflux overnight. After cooling, the reaction was evaporated to dryness then taken up with $CH_2Cl_2$ and washed with water. The organic layer was dried over $Na_2SO_4$, filtered and the solvent evaporated off. The residue was chromatographed eluting with $CH_2Cl_2$/cyclohexane (90/10) to afford the title compound as an oil (900 mg, 29%).
[APCI MS] m/z: 613 (MH+)

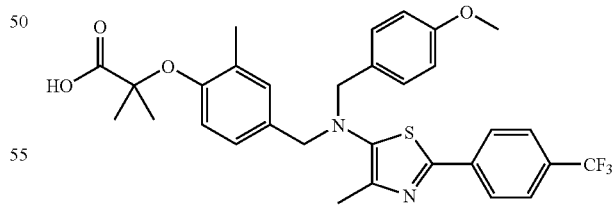

EXAMPLE 89

2-Methyl-2-(4-{([4-methoxybenzyl]-[4-methyl-2-(4-trifluoromethylphenyl)thiazol-5-yl]amino)methyl}-2-methylphenoxy)propionic acid To a solution of example 88 (900 mg, 1.47 mmol) in EtOH (20 mL) was added 1N NaOH (4.4 mL, 3 eq.) and the reaction was stirred at 80° C. for 2 h. When all of the starting material had disappeared, the reaction cooled, evaporated to dryness, taken up with 1N HCl, extracted with CH₂Cl₂ and the organic phase washed with water. The organic layer was then dried over Na₂SO₄, filtered and the solvent removed in vacuo. The residue was chromatographed eluting with CH₂Cl₂ (100%) then CH₂Cl₂/MeOH (95/5) to afford the title compound as a pale brown oil (140 mg, 16%).

[APCI MS] m/z: 585 (MH+) ¹H NMR (300 MHz, CDCl₃) δ: 7.85 (d, 2H), 7.55 (d, 2H), 7.10 (d, 2H), 7.00 (d, 1H), 6.90 (dd, 1H), 6.75 (d, 2H), 6.65 (d, 1H), 3.90 (s, 2H), 3.85 (s, 2H), 3.70 (s, 3H), 2.15, (s, 3H), 2.10 (s, 3H), 1.50 (s, 6H).

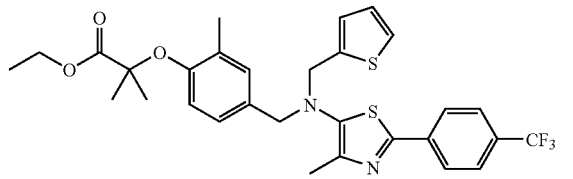

EXAMPLE 90

2-Methyl-2-(2-methyl-4-{([4-methyl-2-(4-trifluoromethylphenyl)thiazol-5-yl]thiophen-2-ylmethylamino)methyl}phenoxy)propionic acid ethyl ester To a solution of intermediate 80 (1.74 g, 4.9 mmol) in 3-methylbutan-2-one (20 mL) was added intermediate 39 (1.24 g, 0.8 eq.) and Cs₂CO₃ (2.08 g, 1.3 eq.) and the reaction was stirred at 105° C. overnight. After cooling, the reaction was evaporated to dryness then taken up with CH₂Cl₂ and washed with water. The organic layer was dried over Na₂SO₄, filtered and the solvent evaporated off. The residue was chromatographed eluting with CH₂Cl₂ to afford the title compound as an orange oil (780 mg, 27%).

¹H NMR (300 MHz, CDCl₃) δ: 7.75 (d, 2H), 7.45 (d, 2H), 7.04 (m, 1H), 6.90 (d, 1H), 6.80 (m, 1H), 6.70 (m, 1H), 6.65 (m, 1H), 6.35 (d, 1H), 4.05 (s, 2H), 4.00 (q, 2H), 3.80 (s, 2H), 2.05 (s, 3H), 2.00 (s, 3H), 1.20 (s, 6H), 1.00 (t, 3H).

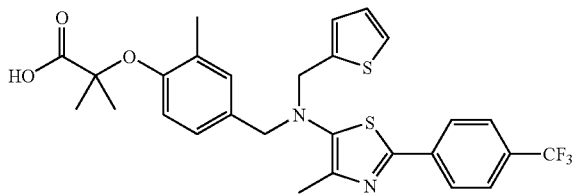

EXAMPLE 91

2-Methyl-2-(2-methyl-4-{([4-methyl-2-(4-trifluoromethylphenyl)thiazol-5-yl-]thiophen-2-ylmethylamino)methyl}phenoxy)propionic acid To a solution of example 90 (780 mg, 1.32 mmol) in EtOH (20 mL) was added 1N NaOH (4 mL, 3 eq.) and the reaction was stirred at 80° C. for 2h. When all of the starting material had disappeared, the reaction cooled, evaporated to dryness, taken up with 1N HCl, extracted with CH₂Cl₂ and the organic phase washed with water. The organic layer was then dried over Na₂SO₄, filtered and the solvent removed in vacuo. The residue was chromatographed eluting with CH₂Cl₂ (100%) then CH₂Cl₂/MeOH (90/10) to afford the title compound as a yellow solid (410 mg, 55.4%).

[APCI MS] m/z: 561 (MH+) Mp: 100° C. (becomes sticky)

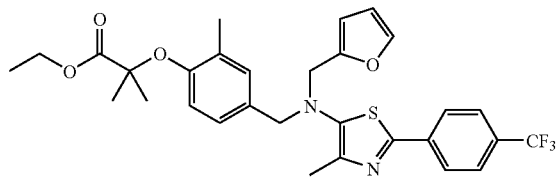

EXAMPLE 92

2-Methyl-2-(2-methyl-4-{([4-methyl-2-(4-trifluoromethylphenyl)thiazol-5-yl]furan-2-ylmethylamino)methyl}phenoxy)propionic acid ethyl ester To a solution of intermediate 82 (540 mg, 1.6 mmol) in 3-methylbutan-2-one (20 mL) was added intermediate 39 (1 g, 2 eq.) and Cs₂CO₃ (1.04 g, 2 eq.) and the reaction was stirred at 105° C. overnight. After cooling, the reaction was evaporated to dryness then taken up with EtOAc and washed with water. The organic layer was dried over Na₂SO₄, filtered and the solvent removed in vacuo. The residue was chromatographed eluting with cyclohexane/EtOAc (95/5) to afford the title compound as a yellow oil (120 mg, 13%).

[APCI MS] m/z: 573 (MH+) ¹H NMR (300 MHz, CDCl₃) δ: 7.85 (d, 2H), 7.55 (d, 2H), 7.30 (m, 1H), 7.00 (m, 1H), 6.90 (m, 1H), 6.50 (d, 1H), 6.20 (m, 1H), 6.05 (m, 1H), 4.15 (q, 2H), 4.00 (s, 2H), 3.95 (s, 2H), 2.20 (s, 3H), 2.15 (s, 3H), 1.50 (s, 6H), 1.10 (t, 3H).

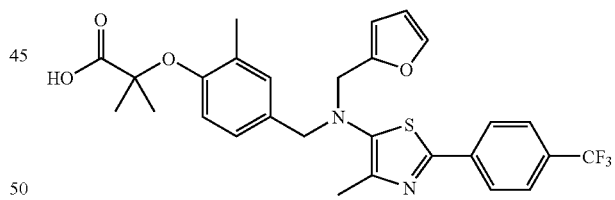

EXAMPLE 93

2-Methyl-2-(2-methyl-4-{([4-methyl-2-(4-trifluoromethylphenyl)thiazol-5-yl]furan-2-ylmethylamino)methyl}phenoxy)propionic acid To a solution of example 92 (120 mg, 0.21 mmol) in EtOH (20 mL) was added 1N NaOH (0.63 mL, 3 eq.) and the reaction was stirred at 70° C. for 2 h. Another 3 eq. of 1N NaOH was added and the reaction stirred for an additional 2 h at 70° C. When all of the starting material had disappeared, the reaction cooled, evaporated to dryness, taken up with 1N HCl, the precipitate collected and washed with water. The precipitate dried under vacuum to afford the title compound as a yellow solid (110 mg, 96%).

[APCI MS] m/z: 545 (MH+) Mp: 80° C. (becomes sticky)

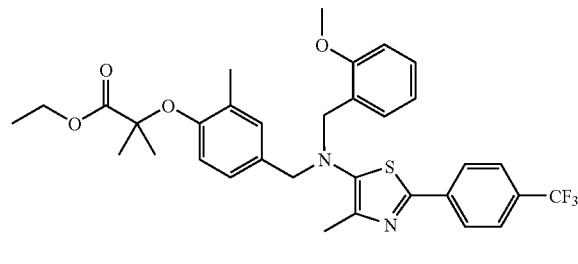

EXAMPLE 94

2-Methyl-2-(2-methyl-4-{([4-methyl-2-(4-trifluoromethylphenyl)thiazol-5-yl][2-methoxybenzyl]amino)methyl}phenoxy)propionic acid ethyl ester To a solution of intermediate 84 (784 mg, 2.1 mmol) in 3-methylbutan-2-one (20 mL) was added intermediate 39 (662 mg, 1 eq.) and $Cs_2CO_3$ (1.03 g, 1.5 eq.) and the reaction was stirred at 105° C. for 48 h. After cooling, the reaction was evaporated to dryness, the residue then taken up with $CH_2Cl_2$ and washed with water. The organic layer was dried over $Na_2SO_4$, filtered and the solvent removed in vacuo. The residue was chromatographed eluting with $CH_2Cl_2$/cyclohexane (90/10) to afford the title compound as an impure oil (520 mg, 40%).

[APCI MS] m/z: 613 (MH+)

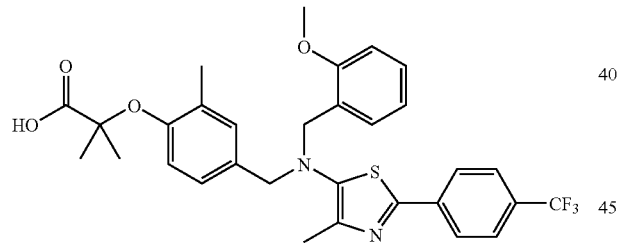

EXAMPLE 95

2-Methyl-2-(2-methyl-4-{([4-methyl-2-(4-trifluoromethylphenyl)thiazol-5-yl][2-methoxybenzyl]amino)methyl}phenoxy)propionic acid To a solution of example 94 (520 mg, 0.85 mmol) in EtOH (20 mL) was added 1N NaOH (2.5 mL, 3 eq.) and the reaction was stirred at 80° C. for 1 h. When all of the starting material had disappeared, the reaction cooled, evaporated to dryness, taken up with 1 N HCl and extracted with $CH_2Cl_2$. The organic phase was dried over $Na_2SO_4$, filtered and the solvent removed in vacuo. The residue was chromatographed eluting with $CH_2Cl_2$ (100%) then $CH_2Cl_2$/MeOH (95/5) to afford the title compound as a yellow oil (80 mg, 16%).

[APCI MS] m/z: 585 (MH+) $^1$H NMR (300 MHz, $CDCl_3$) δ: 7.85 (d, 2H), 7.55 (d, 2H), 7.20 (m, 2H), 7.05 (bs, 1H), 6.95 (dd, 1H), 6.85 (d, 1H), 6.77 (d, 1H), 6.65 (d, 1H), 4.05 (s, 2H), 3.95 (s, 2H), 3.70 (s, 3H), 2.15 (s, 3H), 2.10 (s, 3H), 1.50 (s, 6H).

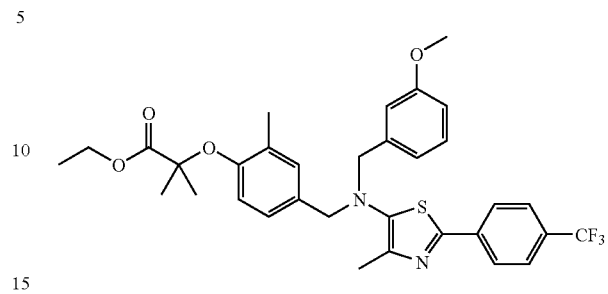

EXAMPLE 96

2-Methyl-2-(2-methyl-4-{([4-methyl-2-(4-trifluoromethylphenyl)thiazol-5-yl][3-methoxybenzyl]amino)methyl}phenoxy)propionic acid ethyl ester To a solution of intermediate 86 (1.08 g, 2.84 mmol) in 3-methylbutan-2-one (20 mL) was added intermediate 39 (895 mg, 1 eq.) and $Cs_2CO_3$ (1.39 g, 1.5 eq.) and the reaction was stirred at 105° C. overnight. After cooling, the reaction was evaporated to dryness and the residue was chromatographed eluting with $CH_2Cl_2$ to afford the title compound as an impure yellow oil (450 mg, 26%).

[APCI MS] m/z: 613 (MH+)

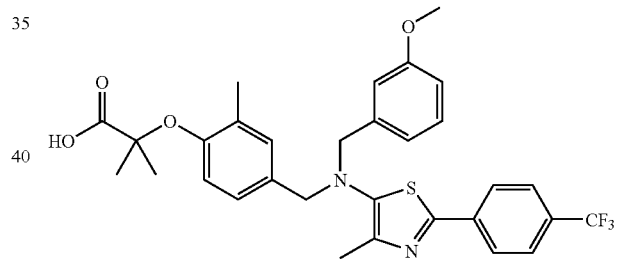

EXAMPLE 97

2-Methyl-2-(2-methyl-4-{([4-methyl-2-(4-trifluoromethylphenyl)thiazol-5-yl][3-methoxybenzyl]amino)methyl}phenoxy)propionic acid To a solution of example 96 (450 mg, 0.29 mmol) in EtOH (20 mL) was added 1N NaOH (0.9 mL, 3 eq.) and the reaction was stirred at 85° C. for 1 h. When all of the starting material had disappeared, the reaction cooled, evaporated to dryness, taken up with 1N HCl, extracted with $CH_2Cl_2$ and washed with water. The organic phase was dried over $Na_2SO_4$, filtered and the solvent removed in vacuo. The residue was chromatographed eluting with $CH_2Cl_2$ (100%) to afford the title compound as a yellow solid (60 mg, 34%).

[APCI MS] m/z: 585 (MH+) $^1$H NMR (300 MHz, $CDCl_3$) δ: 7.85 (d, 2H), 7.55 (d, 2H), 7.10 (t, 1H), 7.00 (bs, 1H), 6.90 (dd, 1H), 6.80 (m, 2H), 6.72 (dd, 1H), 6.70 (d, 1H), 3.95 (s, 2H), 3.90 (s, 2H), 3.70 (s, 3H), 2.17 (s, 3H), 2.15 (s, 3H), 1.50 (s, 6H).

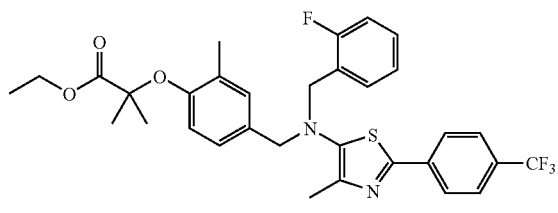

EXAMPLE 98

2-Methyl-2-(2-methyl-4-{([4-methyl-2-(4-trifluoromethylphenyl)thiazol-5-yl][2-fluorobenzyl]amino)methyl}phenoxy)propionic acid ethyl ester To a solution of intermediate 88 (1 g, 27.3 mmol) in 3-methylbutan-2-one (20 mL) was added intermediate 39 (1.2 g, 1.4 eq.) and finely divided $K_2CO_3$ (630 mg, 1.2 eq.) and the reaction was stirred at 80° C. overnight. After cooling, the reaction was evaporated to dryness, the residue taken up in water and extracted with $CH_2Cl_2$. The organic layer was dried over $Na_2SO_4$, filtered and the solvent removed in vacuo. The residue was chromatographed eluting with $CH_2Cl_2$ to afford the title compound as an oil (400 mg, 24%).

$^1$H NMR (300 MHz, $CDCl_3$) δ: 7.85 (d, 2H), 7.55 (d, 2H), 7.15 (m, 2H), 7.00–6.85 (m, 4H), 6.50 (d, 1H), 4.10 (q, 2H), 4.0 (s, 2H), 3.90 (s, 2H), 2.10 (s, 3H), 2.05 (s, 3H), 1.50 (s, 6H), 1.15 (t, 3H).

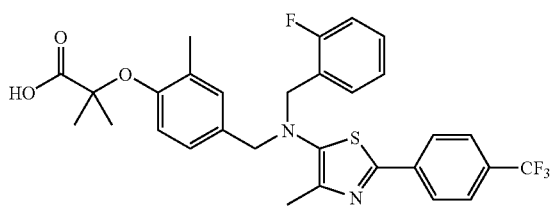

EXAMPLE 99

2-Methyl-2-(2-methyl-4-{([4-methyl-2-(4-trifluoromethylphenyl)thiazol-5-yl][2-fluorobenzyl]amino)methyl}phenoxy)propionic acid To a solution of example 98 (400 mg, 0.68 mmol) in EtOH (20 mL) was added 1N NaOH (20 mL, 30 eq.) and the reaction was stirred at 85° C. for 2 h. When all of the starting material had disappeared, the reaction cooled, evaporated to dryness, taken up with water, neutralized with 1N HCL to pH 6 and extracted with $CH_2Cl_2$. The organic layer was dried over $Na_2SO_4$, filtered and the solvent removed in vacuo. The residue was chromatographed eluting with $CH_2Cl_2$ (100%) then $CH_2Cl_2$/MeOH (98/2) to afford the title compound as an oil (120 mg, 32%).

$^1$H NMR (300 MHz, $CDCl_3$) δ: 7.85 (d, 1H), 7.55 (d, 2H), 7.15 (m, 2H), 7.05–6.90 (m, 4H), 6.65 (d, 1H), 4.05 (s, 2H), 3.95 (s, 2H), 2.15 (s, 3H), 2.05 (s, 3H), 1.50 (s, 6H).

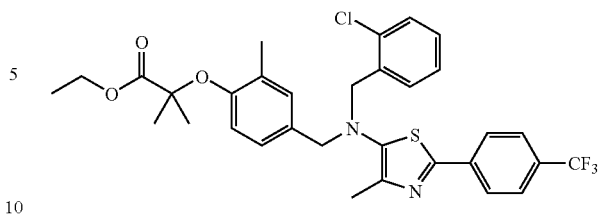

EXAMPLE 100

2-Methyl-2-(2-methyl-4-{([4-methyl-2-(4-trifluoromethylphenyl)thiazol-5-yl][2-chlorobenzyl]amino)methyl}phenoxy)propionic acid ethyl ester The same method was employed as in the preparation of intermediate 98 starting from intermediate 30 (1 g, 2.6 mmol) and intermediate 39 (840 mg, 1 eq.). The title compound was obtained as a dark yellow oil (460 mg, 29%).

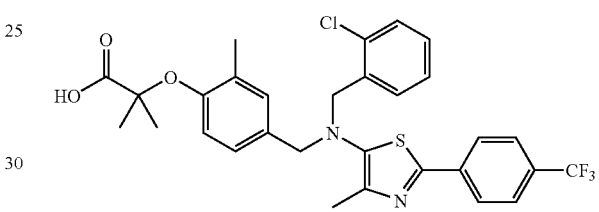

EXAMPLE 101

2-Methyl-2-(2-methyl-4-{([4-methyl-2-(4-trifluoromethylphenyl)thiazol-5-yl][2-chlorobenzyl]amino)methyl}phenoxy)propionic acid The same method was employed as in the preparation of example 99 starting from example 100 (0.46 g, 0.75 mmol). The title compound was obtained as an oil (100 mg, 22%).

$^1$H NMR (300 MHz, $CDCl_3$) δ: 7.85 (d, 2H), 7.55 (d, 2H), 7.25 (m, 2H), 7.10 (m, 2H), 7.00 (bs, 1H), 6.95 (dd, 1H), 6.65 (d, 1H), 4.10 (s, 2H), 3.95 (s, 2H), 2.10 (s, 3H), 1.95 (s, 3H), 1.50 (s, 6H).

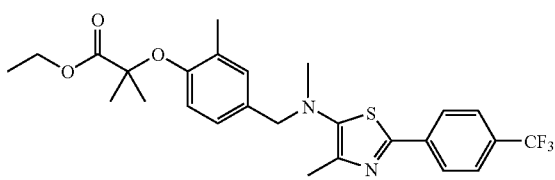

EXAMPLE 102

2-Methyl-2-(2-methyl-4-{([4-methyl-2-(4-trifluoromethylphenyl)thiazol-5-yl][methyl]amino)methyl}phenoxy)propionic acid ethyl ester To intermediate 90 (1 g, 2 mmol) in THF (20 mL) was added NaH (170 mg, 2 eq.) and the mixture stirred for 30 min. To the mixture was then added MeI (0.14 mL, 1.1 eq.)

and the reaction was stirred at 50° C. for 18 h. The reaction was cooled, evaporated to dryness, the residue taken up with CH$_2$Cl$_2$ and washed with water. The organic phase was dried over Na$_2$SO$_4$, filtered and the solvent removed under vacuum. The residue was then chromatographed eluting CH$_2$Cl$_2$ (100%) then CH$_2$Cl$_2$/MeOH (98/2) to afford the title compound as an oil (50 mg, 5%).

$^1$H NMR (300 MHz, CDCl$_3$) δ: 8.05 (d, 2H), 7.75 (d, 2H), 7.20 (bs, 1H), 7.10 (dd, 1H), 6.70 (d, 1H), 4.35 (q, 2H), 4.00 (s, 2H), 2.80 (s, 3H), 2.45 (s, 3H), 2.35 (s, 3H), 1.70 (s, 6H), 1.35 (t, 3H).

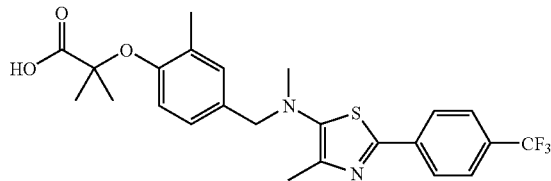

EXAMPLE 103

2-Methyl-2-(2-methyl-4-{([4-methyl-2(4-trifluoromethylphenyl)thiazol-5-yl][methyl]amino)methyl}phenoxy)propionic acid To a solution of example 102 (50 mg, 0.5 mmol) in EtOH (20 mL) was added excess of a 1N NaOH solution and the mixture was stirred at 60° C. for 2 h. The reaction was cooled, evaporated to dryness, the residue taken up with water, neutralized with 1N HCl to pH 7 and then extracted with CH$_2$Cl$_2$. The organic layer was dried over Na$_2$SO$_4$, filtered and the solvent removed under vacuum. The residue was then chromatographed eluting with CH$_2$Cl$_2$ (100%) then CH$_2$Cl$_2$/MeOH (98/2) and finally CH$_2$Cl$_2$/MeOH (95/5) to afford the title compound as an oil (10 mg, 20%).

$^1$H NMR (300 MHz, CDCl$_3$) δ: 7.90 (d, 2H), 7.55 (d, 2H), 7.05 (bs, 1H), 6.95 (dd, 1H), 6.70 (d, 1H), 3.85 (s, 2H), 2,60 (s, 3H), 2.25 (s, 3H), 2.15 (s, 3H), 1.55 (s, 6H).

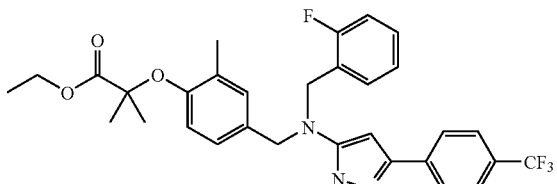

EXAMPLE 104

2-Methyl-2-(2-methyl-4-{([2-methyl-5-(4-trifluoromethylphenyl)-2H-pyrazol-3-yl][2-fluorobenzyl]amino)methyl}phenoxy)propionic acid ethyl ester To a solution of intermediate 92 (850 mg, 2.6 mmol) in 3-methylbutan-2-one (20 mL) was added intermediate 39 (1.25 g, 1.5 eq.) and K$_2$CO$_3$ (550 mg, 1.5 eq.) and the reaction was stirred at 100° C. for 72 h. After cooling, the reaction was evaporated to dryness, taken up with water and extracted with CH$_2$Cl$_2$. The organic layer was dried over Na$_2$SO$_4$, filtered and the solvent removed in vacuo. The residue was chromatographed eluting eluting with CH$_2$Cl$_2$ (100%) then CH$_2$Cl$_2$/MeOH (98/2) and finally CH$_2$Cl$_2$/MeOH (95/5) to afford the title compound as an oil (280 mg, 21%).

$^1$H NMR (300 MHz, CDCl$_3$) δ: 7.85 (d, 2H), 7.65 (d, 2H), 7.25 (m, 2H), 7.10–6.95 (m, 4H), 6.60 (m, 1H), 6.25 (s, 1H), 4.25 (q, 2H), 4.15 (s, 2H), 4.00 (s, 2H), 3.65 (s, 3H), 2.20 (s, 3H), 1.60 (s, 6H), 1.25 (t, 3H).

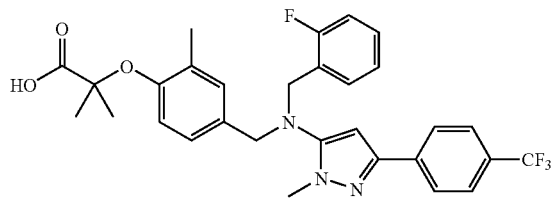

EXAMPLE 105

2-Methyl-2-(2-methyl-4-{([2-methyl-5-(4-trifluoromethylphenyl)-2H-pyrazol-3-yl][2-fluorobenzyl]amino)methyl}phenoxy)propionic acid To a solution of example 104 (320 mg, 0.5 mmol) in EtOH (20 mL) was added excess of a 1N NaOH solution and the mixture was stirred at 50° C. for 2 h. The reaction was cooled, evaporated to dryness, the residue taken up with water, neutralized with 1N HCl to pH 7 and then extracted with CH$_2$Cl$_2$. The organic layer was dried over Na$_2$SO$_4$, filtered and the solvent removed under vacuum to afford the title compound as an oil (150 mg, 50%).

$^1$H NMR (300 MHz, CDCl$_3$) δ: 7.70 (d, 2H), 7.50 (d, 2H), 7.15 (m, 2H), 7.00–6.80 (m, 4H), 6.65 (d, 1H), 6.15 (s, 1H), 4.00 (s, 2H), 3.90 (s, 2H), 3.50 (s, 3H), 2.10 (s, 3H), 1.50 (s, 6H).

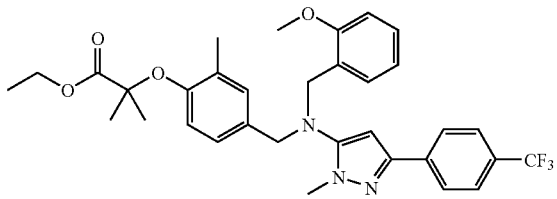

EXAMPLE 106

2-Methyl-2-(2-methyl-4-{([2-methyl-5-(4-trifluoromethylphenyl)-2H-pyrazol-3-yl][2-methoxybenzyl]amino)methyl}phenoxy)propionic acid ethyl ester To a solution of intermediate 94 (900 mg, 2.5 mmol) in 3-methylbutan-2-one (20 mL) was added intermediate 39 (1.18 g, 1.5 eq.) and K$_2$CO$_3$ (520 mg, 1.5 eq.) and the reaction was stirred at 100° C. for 72 h. After cooling, the reaction was evaporated to dryness, taken up with water and extracted with CH$_2$Cl$_2$. The organic layer was dried over Na$_2$SO$_4$, filtered and the solvent removed in vacuo. The residue was chromatographed eluting eluting with CH$_2$Cl$_2$ (100%) then CH$_2$Cl$_2$/MeOH (98/2) and finally CH$_2$Cl$_2$/MeOH (95/5) to afford the title compound as an oil (280 mg, 20%).

$^1$H NMR (300 MHz, CDCl$_3$) δ: 7.85 (d, 2H), 7.65 (d, 2H), 7.30 (m, 2H), 7.15 (bs, 1H), 7.05–6.85 (m, 3H), 6.65 (d, 1H), 6.20 (s, 1H), 4.30 (q, 2H), 4.15 (s, 2H), 4.05 (s, 2H), 3.80 (s, 3H), 3.75 (s, 3H), 2.20 (s, 3H), 1.60 (s, 6H), 1.20 (t, 3H).

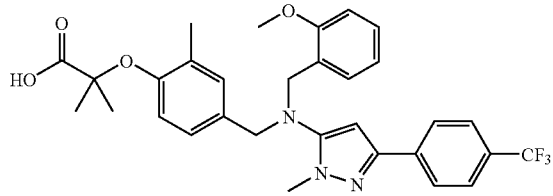

EXAMPLE 107

2-Methyl-2-(2-methyl-4-{([2-methyl-5-(4-trifluoromethylphenyl)-2H-pyrazol-3-yl][2-methoxybenzyl]amino)methyl}phenoxy)propionic acid To a solution of example 106 (280 mg, 0.49 mmol) in EtOH (20 mL) was added excess of a 1N NaOH solution and the mixture was stirred at 50° C. for 2 h. The reaction was cooled, evaporated to dryness, the residue taken up with water, neutralized with 1N HCl to pH 7 and then extracted with CH$_2$Cl$_2$. The organic layer was dried over Na$_2$SO$_4$, filtered and the solvent removed under vacuum. The residue was then chromatographed eluting with CH$_2$Cl$_2$ (100%), CH$_2$Cl$_2$/MeOH (99/1), CH$_2$Cl$_2$/MeOH (98/2) and finally CH$_2$Cl$_2$/MeOH (96/4) to afford the title compound as an oil (60 mg, 22%).

$^1$H NMR (300 MHz, CDCl$_3$) δ: 7.65 (d, 2H), 7.45 (d, 2H), 7.15 (m, 2H), 7.00 (bs, 1H), 6.90–6.80 (m, 2H), 6.75 (d, 1H), 6.65 (d, 1H), 6.10 (s, 1H), 4.05 (s, 2H), 3.95 (s, 2H), 3.65 (s, 3H), 3.60

The following intermediates and ligands were prepared for the binding and transfection assays described below:
(i) 2-{2-methyl-4-[({4-methyl-2-[4-(trifluoromethyl)phenyl]-1,3-thiazol-5-yl}methyl)sulfanyl]phenoxy}acetic acid.

This compound was used as a PPARdelta reference in the transfection assays described below and was prepared according to the method reported in WO200100603-A1

(ii) 2-methyl-2-[4-{[(4-methyl-2-[4-trifluoromethylphenyl]-thiazol-5-yl carbonyl)amino]methyl}-phenoxy]propionic acid.

This compound was used as a PPAR alpha reference in the transfection assay described below and was prepared according to method reported in WO200140207-A1

(iii) 5-{4-[2-(Methyl-pyridin-2-yl-amino)-ethoxy]-benzyl}-thiazolidine-2,4-dione This compound was used as a PPAR gamma reference in the transfection assay described below and was prepared according to method reported in *J. Med. Chem.* 1994, 37(23), 3977

Binding Assay:

Compounds were tested for their ability to bind to hPPAR gamma hPPARalpha or PPAR delta using a Scintillation Proximity Assay (SPA). The PPAR ligand binding domain (LBD) was expressed in *E. coli* as polyHis tagged fusion proteins and purified. The LBD was then labelled with biotin and immobilised on streptavidin-modified scintillation proximity beads. The beads were then incubated with a constant amount of the appropriate radioligand (3H-BRL 49653 for PPARgamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002) and labelled GW 2433 (see Brown, P. J et al. *Chem. Biol.*, 4, 909–918 (1997). For the structure and synthesis of this ligand) for PPAR delta) and variable concentrations of test compound, and after equilibration the radioactivity bound to the beads was measured by a scintillation counter. The amount of nonspecific binding, as assessed by control wells containing 50 µM of the corresponding unlabeled ligand, was subtracted from each data point. For each compound tested, plots of ligand concentration vs. CPM of radioligand bound were constructed and apparent KI values were estimated from nonlinear least squares fit of the data assuming simple competitive binding. The details of this assay have been reported elsewhere (see, Blanchard, S. G. et. al. Development of a Scintillation Proximity Assay for Peroxisome Proliferator-Activated Receptor gamma Ligand Binding Domain. *Anal. Biochem.*, 257, 112–119 (1998)).

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., An antidiabetic thiazolidinedione is a high affinity ligand for peroxisome proliferator-activated receptor gamma (PPARgamma), *J. Biol. Chem.*, 270, 12953–6 (1995). The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and beta-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and beta-galactosidase activity. Alkaline phosphatase activity was corrected for transfection efficiency using the beta-galactosidase activity as an internal standard (see, for example, Kliewer, S. A., et. al. Cell 83, 813–819 (1995)). Rosiglitazone (BRL 49653) was used as a positive control in the hPPAR gamma assay. The positive control in the hPPAR alpha assays was 2-methyl-2-[4-{[(4-methyl-2-[4-trifluoromethylphenyl]-thiazol-5-yl-carbonyl) amino]methyl}-phenoxy]propionic acid. The positive control for PPAR delta assays was 2-[2-methyl-4-[({4-methyl-2-{trifluoromethyl)phenyl]-1,3-thiazol-5-yl}methyl) sulfanyl]phenoxy}acetic acid.

What is claimed is:

1. A compound of formula (1) or a pharmaceutically acceptable salt, solvate, or hydrolysable ester thereof, (I)

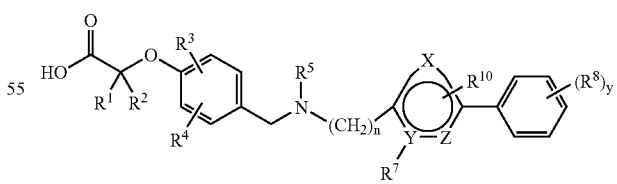

wherein:
R$^1$ and R$^2$ are independently H or C$_{1-3}$ alkyl;
R$^3$ and R$^4$ are independently H, C$_{1-3}$ alkyl, OCH$_3$, CF$_3$, allyl, or halogen;
n is 0 or 1
Y is N;
Z is N;
X is CH;

each $R^6$ is independently $C_{1-3}$ alkyl, $CF_3$, $OCH_3$, $OCF_3$, or halogen;

y is 0, 1, 2, 3, 4, or 5;

$R^7$ is H, $CF_3$, $C_{2-6}$ alkenyl; or $R^7$ is $C_{1-6}$ alkyl optionally substituted by phenyl wherein the phenyl is optionally substituted by —O—$C_{1-3}$ alkyl;

$R^{10}$ is H or $C_{1-3}$ alkyl;

$R^5$ represents H, $C_{1-6}$ alkyl, $C_{1-3}$ alkyl —O—$C_{1-3}$ alkyl, $C_{2-6}$ alkenyl, or $C_{1-6}$ alkoxy, each of which may be optionally substituted by one or more halogens; or $R^5$ is a group —$CH_2$-D wherein D is

wherein P represents O, N or S, and when P is N, the depicted bond can be attached to the nitrogen in the ring as well as any of the carbons in the ring;

or D is

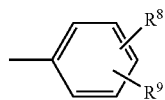

wherein $R^8$ and $R^9$ independently represent H, halogen, $C_{1-6}$ alkyl or —$OC_{1-6}$ alkyl.

2. A compound according to claim 1 wherein $R^1$ and $R^2$ are both H or both methyl.

3. A compound according to claim 2 wherein $R^1$ and $R^2$ are both methyl.

4. A compound according to claim 1 wherein $R^3$ and $R^4$ are independently H, $CH_3$ or Cl.

5. A compound according to claim 1 wherein $R^3$ and $R^4$ are ortho to the point of attachment of the depicted O atom.

6. A compound according to claim 5 wherein $R^3$ and $R^4$ are both methyl.

7. A compound according to claim 5 wherein $R^3$ is methyl or Cl and $R^4$ is H.

8. A compound according to claim 1 wherein $R^6$ is halogen —$OCF_3$ or —$CF_3$.

9. A compound according to claim 8 wherein $R^6$ is $CF_3$.

10. A compound according to claim 1 wherein y represents 1.

11. A compound according to claim 10 wherein the substituent $R^6$ is in the para position.

12. A compound according to claim 1 wherein $R^{10}$ is H or $CH_3$.

13. A compound according to claim 12 wherein $R^{10}$ is H.

14. A compound according to claim 1 wherein $R^7$ is H, $C_{1-6}$ alkyl, $C_{2-3}$ alkenyl, or —$CH_2$-phenyl wherein said phenyl is optionally substituted by —$OCH_3$.

15. A compound according to claim 1 wherein R5 is H, $C_{1-6}$ alkyl, —$CH_2$D, —$CH_2CF3$, or $C_{1-3}$ alkyl-O—$CH_3$.

16. A pharmaceutical composition comprising a compound according to claim 1.

17. A compound according to claim 1 selected from

2-[4-({[5-(4-Chloro-phenyl-2-methyl-2H-pyrazol-3-yl]-thiophen-3-ylmethyl-amino}-methyl)2,6-dimethyl-phenoxy]-2-methyl-propionic acid ethyl ester;

2-[4-({[5-(4-Chloro-phenyl)-2-methyl-2H-pyrazol-3-yl]-thiophen-3-ylmethyl-amino}-methyl)2,6-dimethyl-phenoxy]-2-methyl-propionic acid;

2-[4-({[5-(4-Chloro-phenyl)-2-methyl-2H-pyrazol-3-yl]-methyl-amino}-methyl)2,6-dimethyl-phenoxy]-2-methyl-propionic acid ethyl ester;

2-[4-({[5-(4-Chloro-phenyl)-2-methyl-2H-pyrazol-3-yl]-methyl-amino}-methyl)2,6-dimethyl-phenoxy]-2-methyl-propionic acid;

2-[4-({(2-Chloro-benzyl)-[5-(4-chloro-phenyl)-2-methyl-2H-pyrazol-3-yl]-amino}-methyl)2,6-dimethyl-phenoxy]-2-methyl-propionic acid ethyl ester;

2-[4-({(2-Chloro-benzyl)-[5-(4-chloro-phenyl)-2-methyl-2H-pyrazol-3-yl]-amino}-methyl)-2,6-dimethyl-phenoxy]-2-methyl-propionic acid;

2-[4-({(4-Methoxy-benzyl)-[2-methyl-5-(4-trifluoromethyl-phenyl)-2H-pyrazol-3-yl]-amino}-methyl)-2,6-dimethyl-phenoxy]-2-methyl-propionic acid ethyl ester;

2-[4-({(4-Methoxy-benzyl)-[2-methyl-5-(4-trifluoromethyl-phenyl)-2H-pyrazol-3-yl]-amino}-methyl)-2,6-dimethyl-phenoxy]-2-methyl-propionic acid;

2-[2,6-Dimethyl-4-({[2-methyl-5-(4-trifluoromethyl-phenyl)-2H-pyrazol-3-yl]-thiophen-3-ylmethyl-amino}-methyl)phenoxy]-2-methyl-propionic acid ethyl ester;

2-[2,6-Dimethyl-4-({[2-methyl-5-(4-trifluoromethyl-phenyl)-2H-pyrazol-3-yl]-thiophen-3-ylmethyl-amino}-methyl-phenoxy]-2-methyl-propionic acid;

2-[4-({(4-Fluoro-benzyl)-[2-methyl-5-(4-trifluoromethyl-phenyl)-2H-pyrazol-3-yl]-amino}-methyl)-2,6-dimethyl-phenoxy]-2-methyl-propionic acid ethyl ester;

2-[4-({(4-Fluoro-benzyl)-[2-methyl-5-(4-trifluoromethyl-phenyl)-2H-pyrazol-3-yl]-amino}-methyl)-2,6-dimethyl-phenoxy]-2-methyl-propionic acid;

2-(4-{[5-(4-Chloro-phenyl)-2-methyl-2H-pyrazol-3-yl-amino]-methyl}-2-methyl-phenoxy)-2-methyl-propionic acid ethyl ester;

2-[4-({[5-(4-Chloro-phenyl)-2-methyl-2H-pyrazol-3-yl]-ethyl-amino}-methyl)-2-methyl-phenoxy]-2-methyl-propionic acid ethyl ester;

2-[4-({[5-(4-Chloro-phenyl)-2-methyl-2H-pyrazol-3-yl]-ethyl-amino}-methyl)2 methyl-phenoxy]-2-methyl-propionic acid;

2-methyl-2-[4-(((1-methyl-3-(4-trifluoromethylphenyl))-pyrazol-5-yl)methyl-N-methyl-aminomethyl)phenoxy] propionic acid ethyl ester;

2-methyl-2-[2-methyl-4-(((1-methyl-3-(4-trifluoromethylphenyl))-pyrazol-5-yl)methyl-N-methyl-aminomethyl)phenoxy]propionic acid ethyl ester;

2-methyl-2-[2-chloro-4-(((1-methyl-3-(4-trifluoromethylphenyl))-pyrazol-5-yl)methyl-N-methyl-aminomethyl)phenoxy]propionic acid ethyl ester;

2-methyl-2-[2-methyl-4-((1,4-dimethyl-3-(4-trifluoromethylphenyl)-pyrazol-5-yl)methyl-N-methyl-aminomethyl)phenoxy]propionic acid ethyl ester;

2-methyl-2-[2-chloro-4-((1-methyl-3-(4-trifluoromethoxyphenyl)-pyrazol-5-yl)methyl-N-methyl-aminomethyl)phenoxy]propionic acid ethyl ester;

2-methyl-2-[2-methyl-4-((1-methyl-3-(4-trifluoromethylphenyl)-pyrazol-5-yl)methyl-N-propyl-aminomethyl)phenoxy]propionic acid ethyl ester;

2-methyl-2-[2-chloro-4-((1-methyl-3-(4-trifluoromethylphenyl)-pyrazol-5-yl)methyl-N-(propen-2-yl)-aminomethyl)phenoxy]propionic acid ethyl ester;

2-methyl-2-[4-((1-propyl-3-(4-trifluoromethylphenyl)-pyrazol-5-yl)methyl-N-methyl-aminomethyl)phenoxy]propionic acid ethyl ester;

2-methyl-2-[2-chloro-4-((1-propyl-3-(4-trifluoromethylphenyl)-pyrazol-5-yl)methyl-N-methyl-aminomethyl)phenoxy]propionic acid ethyl ester;

2-methyl-2-[2-chloro-4-((1-(propen-2-yl)-3-(4-trifluoromethoxyphenyl)-pyrazol-5-yl)methyl-N-methyl-aminomethyl)phenoxy]propionic acid ethyl ester;

2-methyl-2-[2-chloro-4-((1-(3-methyl-butyl)-3-(4-trifluoromethoxyphenyl)-pyrazol-5-yl)methyl-N-methyl-aminomethyl)phenoxy]propionic acid ethyl ester;

2-methyl-2-[4-((1-benzyl-3-(4-trifluoromethylphenyl)-pyrazol-5-yl)methyl-N-methyl-aminomethyl)phenoxy]propionic acid ethyl ester;

2-methyl-2-[2-chloro-4-((1-benzyl-3-(4-trifluoromethylphenyl)pyrazol-5-yl)methyl-N-methyl-aminomethyl)phenoxy]propionic acid ethyl ester;

2-methyl-2-[2-chloro-4-((1-benzyl-3-(4-trifluoromethoxyphenyl)-pyrazol-5-yl)methyl-N-(propen-2-yl)aminomethyl)phenoxy]propionic acid ethyl ester;

2-methyl-2-[2-methyl-4-((1-(4-methoxybenzyl)-3-(4-trifluoromethylphenyl)-pyrazol-5-yl)methyl-N-methyl-aminomethyl)phenoxy]propionic acid ethyl ester;

2-methyl-2-[4-(((1-methyl-3-(4-trifluoromethylphenyl))pyrazol-5-yl)methyl-N-methyl-aminomethyl)phenoxy]propionic acid;

2-methyl-2-[2-methyl-4-(((1-methyl-3-(4-trifluoromethylphenyl))-pyrazol-5-yl)methyl-N-methyl-aminomethyl)phenoxy]propionic acid;

2-methyl-2-[2-chloro-4-(((1-methyl-3-(4-trifluoromethylphenyl))-pyrazol-5-yl)methyl-N-methyl-aminomethyl)phenoxy]propionic acid;

2-methyl-2-[2-methyl-4-(((1,4-dimethyl-3-(4-trifluoromethylphenyl))-pyrazol-5-yl)methyl-N-methyl-aminomethyl)phenoxy]propionic acid;

2-methyl-2-[2-chloro-4-(((1-methyl-3-(4-trifluoromethoxyphenyl))-pyrazol-5-yl)methyl-N-methyl-aminomethyl)phenoxy]propionic acid;

2-methyl-2-[2-methyl-4-(((1-methyl-3-(4-trifluoromethylphenyl))-pyrazol-5-yl)methyl-N-propyl-aminomethyl)phenoxy]propionic acid;

2-methyl-2-[2-chloro-4-(((1-methyl-3-(4-trifluoromethylphenyl))-pyrazol-5-yl)methyl-N-(propen-2-yl)-aminomethyl)phenoxy]propionic acid;

2-methyl-2-[4-(((1-propyl-3-(4-trifluoromethylphenyl))-pyrazol-5-yl)methyl-N-methyl-aminomethyl)phenoxy]propionic acid;

2-methyl-2-[2-chloro-4-(((1-propyl-3-(4-trifluoromethylphenyl))-pyrazol-5-yl)methyl-N-methyl-aminomethyl)phenoxy]propionic acid;

2-methyl-2-[2-chloro-4-(((1-(propen-2-yl)-3-(4-trifluoromethoxyphenyl))-pyrazol-5-yl)methyl-N-methyl-aminomethyl)phenoxy]propionic acid;

2-methyl-2-[2-chloro-4-(((1-(methyl-3-butyl)-3-(4-trifluoromethoxyphenyl))-pyrazol-5-yl)methyl-N-methyl-aminomethyl)phenoxy]propionic acid;

2-methyl-2-[4-(((1-benzyl-3-(4-trifluoromethylphenyl))pyrazol-5-yl)methyl-N-methyl-aminomethyl)phenoxy]propionic acid;

2-methyl-2-[2-chloro-4-(((1-benzyl-3-(4-trifluoromethylphenyl))pyrazol-5-yl)methyl-N-methyl-aminomethyl)phenoxy]propionic acid;

2-methyl-2-[2-chloro-4-(((1-benzyl-3-(4-trifluoromethylphenyl))pyrazol-5-yl)methyl-N-(propen-2-yl)-aminomethyl)phenoxy]propionic acid;

2-methyl-2-[2-methyl-4-(((1-(4-methoxybenzyl)-3-(4-trifluoromethylphenyl))-pyrazol-5-yl)methyl-N-methyl-aminomethyl)phenoxy]propionic acid;

2-Methyl-2-(2-methyl-4-{([2-methyl-5-(4-trifluoromethylphenyl)-2H-pyrazol-3-yl][2-fluorobenzyl]amino)methyl}phenoxy)propionic acid ethyl ester;

2-Methyl-2-(2-methyl-4-{([2-methyl-5-(4-trifluoromethylphenyl)-2H-pyrazol-3-yl][2-fluorobenzyl]amino)methyl}phenoxy)propionic acid;

2-Methyl-2-(2-methyl-4-{([2-methyl-5-(4-trifluoromethylphenyl)-2H-pyrazol-3-yl][2-methoxybenzyl]amino)methyl}phenoxy)propionic acid ethyl ester; and 2-Methyl-2-(2-methyl-4-{([2-methyl-5-(4-trifluoromethylphenyl)-2H-pyrazol-3-yl][2-methoxybenzyl]amino)methyl}phenoxy)propionic acid.

* * * * *